US010799559B2

(12) United States Patent
Hinken et al.

(10) Patent No.: US 10,799,559 B2
(45) Date of Patent: Oct. 13, 2020

(54) NOPE FOR TREATMENT OF PATHOLOGICAL MUSCLE LOSS AND WEAKNESS

(71) Applicants: Five Prime Therapeutics, Inc., South San Francisco, CA (US); Glaxosmithkline Intellectual Property Development Limited, Brentford, Middlesex (GB)

(72) Inventors: Aaron Curtis Hinken, King of Prussia, PA (US); Amy W. Hsu, Moraga, CA (US); Janine Powers, Alameda, CA (US); Warren James Rocque, Collegeville, PA (US); Alan James Russell, King of Prussia, PA (US)

(73) Assignees: Five Prime Therapeutics, Inc., South San Francisco, CA (US); Glaxosmithkline Intellectual Property Development Limited, Brentford, Middlesex (GB)

(*) Notice: Subject to any disclaimer, the term of this patent is extended or adjusted under 35 U.S.C. 154(b) by 0 days.

(21) Appl. No.: 16/095,974

(22) PCT Filed: Apr. 24, 2017

(86) PCT No.: PCT/IB2017/052345
§ 371 (c)(1),
(2) Date: Oct. 24, 2018

(87) PCT Pub. No.: WO2017/187319
PCT Pub. Date: Nov. 2, 2017

(65) Prior Publication Data
US 2019/0125833 A1 May 2, 2019

Related U.S. Application Data

(60) Provisional application No. 62/326,914, filed on Apr. 25, 2016.

(51) Int. Cl.
*A61K 38/17* (2006.01)
*C07K 14/705* (2006.01)
*A61P 7/06* (2006.01)
*A61P 21/00* (2006.01)
*A61P 25/28* (2006.01)

(52) U.S. Cl.
CPC ............ *A61K 38/1774* (2013.01); *A61P 7/06* (2018.01); *A61P 21/00* (2018.01); *A61P 25/28* (2018.01); *C07K 14/70503* (2013.01); *C07K 2319/30* (2013.01)

(58) Field of Classification Search
None
See application file for complete search history.

(56) References Cited

U.S. PATENT DOCUMENTS

| 2002/0102551 A1 | 8/2002 | Salbaum | |
| 2004/0181033 A1* | 9/2004 | Han | C07K 14/00 530/324 |
| 2013/0209489 A1* | 8/2013 | Han | C07K 16/22 424/158.1 |

OTHER PUBLICATIONS

Fearon et al. ('Cancer Cachexia: Mediators, signaling, and metabolic pathways' Cell Metabolism v16 Aug. 2012 pp. 153-166). (Year: 2012).*
NORD website (retrieved from https://rarediseases.org/rare-diseases/congenital-muscular-dystrophy/ on Oct. 30, 2019, 22 pages) (Year: 2019).*
Panchenko et al. ('Prediction of functional sites by analysis of sequence and structure conservation' Protein Science v13 2004 pp. 884-892) (Year: 2004).*
Shamley et al. ('Changes in shoulder muscle size and activity following treatment for breast cancer' Breast Cancer Res Treat v106 2007 pp. 19-27) (Year: 2007).*
Weidle et al. ('Genetically engineered fusion proteins for treatment of cancer' Cancer Genomics & Proteomics v9 2012 pp. 357-372) (Year: 2012).*
Elkina, et al., The role of myostatin in muscle wasting: an overview, J. Cachexia Sarcopenia Muscle, 2011, pp. 143-151, vol. 2.
Han, et al., Myostatin/activin pathway antagonism: molecular basis and therapeutic potential, Int. Journal of Biochemistry & Cell Biology, 2013, pp. 2333-2347, vol. 45.
Han, et al., Targeting the myostatin signaling pathway to treat muscle wasting diseases, Current Opinion in Supportive and Palliative Care, 2011, pp. 334-341, vol. 5.
Lee, Se-Jin, Regulation of muscle mass by myostatin, Annu. Rev. Cell Dev. Biol., 2004, pp. 61-86, vol. 20.
McPherron, et al., Regulation of skeletal muscle mass in mice by a new TGF-beta superfamily member, Nature, May 1, 1997, pp. 83-90, vol. 387.
Salbaum, J. Michael, Genomic structure and chromosomal localization of the mouse gene Punc, Mammalian Genome, 1999, pp. 107-111, vol. 10, No. 1.
Salbaum, et al., Cloning and expression of nope, a new mouse gene of the immunoglobulin superfamily related to guidance receptors, Genomics, 2000, pp. 15-23, vol. 64, No. 1.
Schuelke, et al., Myostatin mutation associated with gross muscle hypertrophy in a child, New England Journal of Medicine, Jun. 24, 2004, pp. 2682-2688, vol. 350.
Tsuchida, Kunihiro, Targeting myostatin for therapies against muscle-wasting disorders, Current Opinion in Drug Discovery & Development, 2008, pp. 487-494, vol. 11 (4).
R&D Systems Catalog Rev. Oct. 12, 2015, Recombinant Mouse Nope Fc Chimera, Catalog No. 1394-NP, [online], [Retrieved by the EPO on Jun. 27, 2017 and reported in ISR mailed Aug. 21, 2017] Retrieved from the Internet: <URL: https://resources.rndsystems.com/pdfs/datasheets/1394-np.pdf>.

(Continued)

Primary Examiner — Ronald T Niebauer
(74) Attorney, Agent, or Firm — McNeill Baur PLLC

(57) ABSTRACT

Methods of treating muscle wasting and other disorders with NOPE extracellular domain (ECD) polypeptides and NOPE ECD fusion molecules are provided.

20 Claims, 6 Drawing Sheets

Specification includes a Sequence Listing.

(56) References Cited

OTHER PUBLICATIONS

International Search Report of International Application No. PCT/IB2017/052345, dated Aug. 21, 2017.

* cited by examiner

Figure 1

| Sample | Ligand | ka (1/Ms) | kd (1/s) | KD (nM) |
|---|---|---|---|---|
| Myostatin | hNOPE-FC | 2.0E+06 | 3.2E-04 | 0.2 |
| | mNOPE-FC | 6.7E+05 | 5.8E-04 | 0.9 |
| | ActR2b-FC | 3.9E+05 | 9.8E-04 | 2.5 |
| Pro Myostatin | hNOPE-FC | -- | -- | NB |
| | mNOPE-FC | -- | -- | NB |
| | ActR2b-FC | -- | -- | NB |

NOPE FOR TREATMENT OF PATHOLOGICAL MUSCLE LOSS AND WEAKNESS

CROSS-REFERENCE TO RELATED APPLICATIONS

This application is a national stage application under 35 U.S.C. 371 of International Application No. PCT/IB2017/052345, filed on Apr. 24, 2017, which claims the benefit of priority of US Provisional Application No. 62/326,914, filed Apr. 25,2016, each of which is incorporated by reference herein in its entirety for any purpose.

TECHNICAL FIELD

Methods of treating muscle wasting and other disorders with Neighbor of PuncE11 (NOPE), such as NOPE extracellular domain (ECD) polypeptides and NOPE ECD fusion molecules are provided.

BACKGROUND

Skeletal muscle loss and physical weakness are a common feature of many conditions of disuse, such as bed rest and aging, neuromuscular injury, such as ALS and spinal cord injury, and chronic disease including cancer, diabetes, and heart failure. Muscle loss decreases physical function, but also negatively impacts patient prognosis and increases mortality (Cohen et al. Nature Rev Drug Disc 2015. 14, 58-74). Therefore, there exists a need for effective therapies for the treatment or prophylaxis of diseases associated with decreases in any one or a combination of muscle mass, muscle strength, and muscle function.

The transforming growth factor-beta (TGF-beta) superfamily contains a variety of secreted growth factors that share common sequence elements and structural motifs. Myostatin, also known as Growth and Differentiation Factor (GDF-8), is a member of the TGF-β superfamily and is highly conserved across mammals. Myostatin has been characterized as a negative regulator of skeletal muscle mass (McPherron A C, Lawler A M, Lee S J. 1997. Nature 387(6628):83-90) with genetic inactivation or neutralization of myostatin associated with increased muscle mass during development and adulthood (Schuelke et al., N Engl J Med 2004, 350:2682-8 and Lee S J Annu Rev Cell Dev Biol. 2004; 20:61-86). In addition, circulating levels of myostatin are increased in many conditions of muscle wasting (Han H Q, Mitch W E. Curr Opin Support Palliat Care 2011 December; 5(4):334-41 and Elkina et al. J Cachexia Sarcopenia Muscle 2011; 2:143-151). Approaches to inhibit myostatin as a therapeutic strategy in disorders of muscle wasting and weakness have exhibited potential with pharmacological blockade showing prevention or reversal of muscle loss and prolongation of lifespan in various animal models of disease including cancer cachexia and renal failure (as reviewed Curr Opin Drug Discov Devel. 2008 July; 11(4):487-94. and Int J Biochem Cell Biol. 2013 October; 45(10):2333-47.). However no current therapies are approved and therefore a need remains.

NOPE is a protein that directly binds and neutralizes myostatin, as well as a closely-related family member GDF11, and provides a novel approach to increase skeletal muscle mass. This may offer an effective therapy for the treatment or prophylaxis of diseases associated with muscle wasting.

SUMMARY

In some embodiments, methods of reducing or delaying muscle wasting in a subject with muscle wasting or at risk of muscle wasting are provided, comprising administering to the subject an effective amount of a NOPE extracellular domain (ECD) polypeptide. In some embodiments, the subject has at least one condition selected from chronic obstructive pulmonary disease (COPD), chronic kidney disease, end stage renal disease, chronic heart failure, cancer, critical illness myopathy, critical illness polyneuropathy, stroke, spinal cord injury, spinal muscular atrophy, multiple sclerosis, progressive multifocal leukoencephalopathy, encephalomyelitis, central pontine myelolysis, adrenoleukodystrophy, Wallerian degeneration, Huntington's disease, Parkinson's disease, traumatic brain injury, Alexander's disease, Pelizaeus Merzbacher disease, globoid cell leucodystrophy, and sarcopenia.

In some embodiments, methods of treating muscle injury are provided, comprising administering to a subject with muscle injury an effective amount of a NOPE extracellular domain (ECD) polypeptide. In some embodiments, the muscle injury is selected from surgery-related muscle injury, traumatic muscle injury, work-related skeletal muscle injury, and overtraining-related muscle injury.

In some embodiments, methods of treating a muscle degenerative disorder are provided, comprising administering to a subject with a muscle degenerative disorder an effective amount of a NOPE extracellular domain (ECD) polypeptide. In some embodiments, the muscle degenerative disorder is selected from muscular dystrophy, myotonic dystrophy, polymyositis, and dermatomyositis. In some embodiments, the muscle degenerative disorder is muscular dystrophy. In some embodiments, the muscular dystrophy is selected from Duchenne muscular dystrophy, Becker muscular dystrophy, congenital muscular dystrophy (Fukuyama), Emery Dreifuss muscular dystrophy, limb girdle muscular dystrophy, and fascioscapulohumeral muscular dystrophy. In some embodiments, the muscle degenerative disorder is myotonic dystrophy. In some embodiments, the myotonic dystrophy is selected from myotonic dystrophy type I, myotonic dystrophy type II, and congenical myotonia.

In various embodiments, treating comprises at least one of delaying progression of muscle wasting, improving the subject's 6 minute walking distance (6 MWD), reducing physical decline, delaying occurrence of life-changing events, improving independence, reducing hospitalizations, and delaying the need for an assisted living arrangement. In some embodiments, the subject's 6 MWD is increased by at least 10 meters, or at least 20 meters, or at least 30 meters after 12 months of treatment. In some embodiments, the method comprises delaying the need for a wheelchair and/or delaying placement of a ventilator.

In some embodiments, methods of treating amyotrophic lateral sclerosis (ALS) are provided, comprising administering to a subject with ALS an effective amount of a NOPE extracellular domain (ECD) polypeptide. In some embodiments, treating ALS comprises at least one of delaying progression of ALS, reducing physical decline, improving forced vital capacity, slowing the decline in forced vital capacity, slowing the decline in the subject's score on the ALS functional rating scale (ALSFRS), improving the subject's score on the ALSFRS, delaying occurrence of life-changing events, and improving the subject's time of survival. In some embodiments, the method comprises delaying a tracheostomy and/or delaying placement of a percutaneous endoscopic gastrostomy (PEG).

In various embodiments, administration of the NOPE extracellular domain (ECD) polypeptide increases type I slow muscle mass and/or decreases fat mass.

In some embodiments, methods of increasing type I slow muscle mass are provided, comprising administering to a subject an effective amount of a NOPE extracellular domain (ECD) polypeptide.

In some embodiments, methods of decreasing fat mass are provided, comprising administering to a subject an effective amount of a NOPE extracellular domain (ECD) polypeptide.

In some embodiments, uses of a NOPE extracellular domain (ECD) polypeptide for reducing or delaying muscle wasting in a subject with muscle wasting or at risk of muscle wasting are provided. In some embodiments, the subject has at least one condition selected from chronic obstructive pulmonary disease (COPD), chronic kidney disease, end stage renal disease, chronic heart failure, cancer, critical illness myopathy, critical illness polyneuropathy, stroke, spinal cord injury, spinal muscular atrophy, multiple sclerosis, progressive multifocal leukoencephalopathy, encephalomyelitis, central pontine myelolysis, adrenoleukodystrophy, Wallerian degernation, Huntington's disease, Parkinson's disease, traumatic brain injury, Alexander's disease, Pelizaeus Merzbacher disease, globoid cell leucodystrophy, and sarcopenia.

In some embodiments, uses of a NOPE extracellular domain (ECD) polypeptide for treating muscle injury in a subject are provided. In some embodiments, the muscle injury is selected from surgery-related mulcle injury, traumatic muscle injury, work-related skeletal muscle injury, and overtraining-related muscle injury.

In some embodiments, uses of a NOPE extracellular domain (ECD) polypeptide for treating a muscle degenerative disorder in a subject are provided. In some embodiments, the muscle degenerative disorder is selected from muscular dystrophy, myotonic dystrophy, polymyositis, and dermatomyositis. In some embodiments, treating comprises at least one of delaying progression of muscular dystrophy, improving the subject's 6 minute walking distance (6 MWD), reducing physical decline, delaying occurrence of life-changing events, improving independence, reducing hospitalizations, and delaying the need for an assisted living arrangement.

In some embodiments, uses of a NOPE extracellular domain (ECD) polypeptide for treating amyotrophic lateral sclerosis (ALS) in a subject are provided. In some embodiments, treating ALS comprises at least one of delaying progression of ALS, reducing physical decline, improving forced vital capacity, slowing the decline in forced vital capacity, slowing the decline in the subject's score on the ALS functional rating scale (ALSFRS), improving the subject's score on the ALSFRS, delaying occurrence of life-changing events, and improving the subject's time of survival. In some embodiments, administration of the NOPE extracellular domain (ECD) polypeptide increases type I slow muscle mass and/or decreases fat mass.

In some embodiments, uses of a NOPE extracellular domain (ECD) polypeptide for increasing type I slow muscle mass in a subject are provided. In some embodiments, uses of a NOPE extracellular domain (ECD) polypeptide for decreasing fat mass in a subject are provided. In some embodiments, uses of a NOPE extracellular domain (ECD) polypeptide for treating anemia and/or thalassemia in a subject are provided.

In various embodiments, the NOPE extracellular domain (ECD) polypeptide is a NOPE ECD fusion molecule. In some embodiments, the NOPE ECD polypeptide or NOPE ECD fusion molecule is capable of binding myostatin with a $K_D$ of less than 100 nM. In some embodiments, the NOPE ECD polypeptide or NOPE ECD fusion molecule inhibits myostatin-mediated activation of SMAD2/3. In some embodiments, the NOPE ECD polypeptide or NOPE ECD fusion molecule comprises amino acids 25 to 620 of SEQ ID NO: 1. In some embodiments, the NOPE extracellular domain (ECD) polypeptide is a NOPE ECD fusion molecule. In some embodiments, the NOPE ECD fusion molecule comprises a NOPE ECD polypeptide and a fusion partner. In some embodiments, the fusion partner is an Fc. In some embodiments, the NOPE ECD fusion molecule comprises the sequence of SEQ ID NO: 19.

Any embodiment described herein or any combination thereof applies to any and all methods of the invention described herein.

BRIEF DESCRIPTION OF THE FIGURES

FIG. 1 shows an alignment of the human and mouse NOPE extracellular domains with signal sequence.

DETAILED DESCRIPTION

Figure 2:
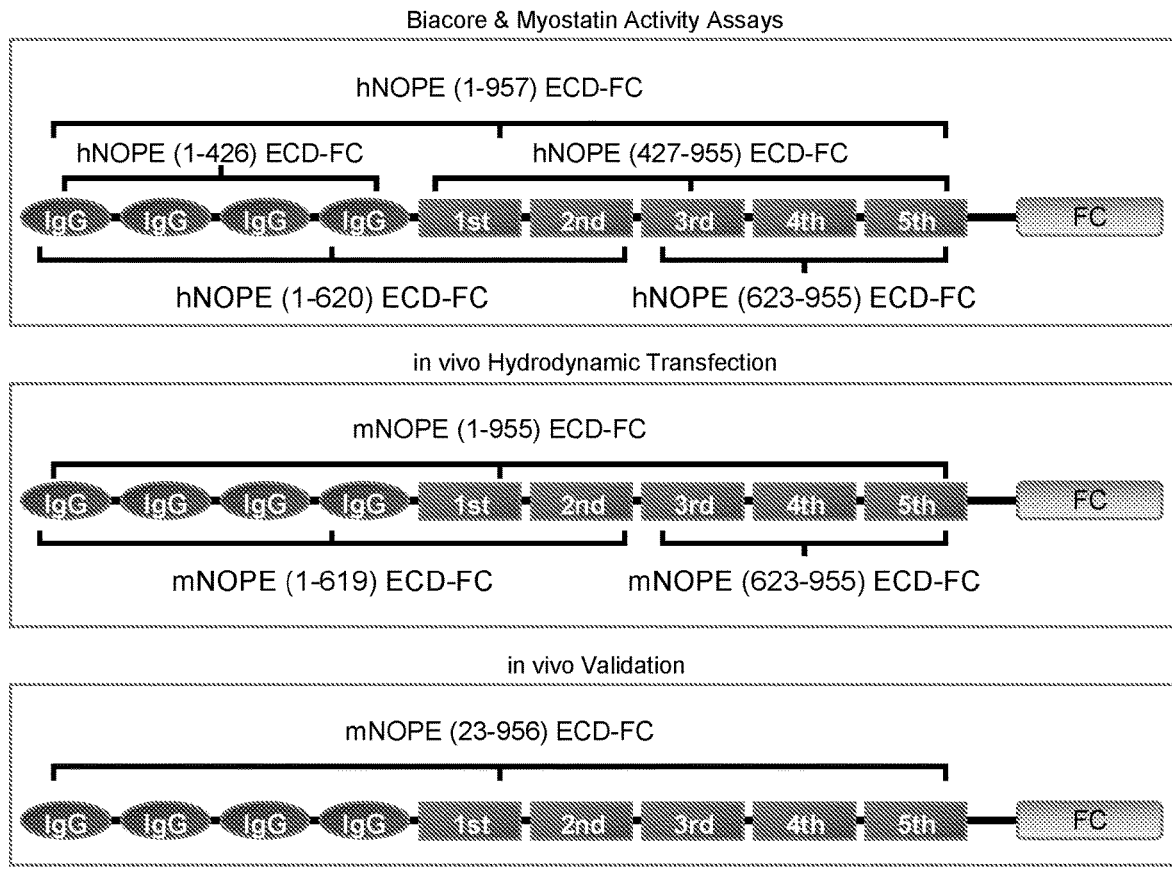
FIG. 2 shows the structures of the NOPE extracellular domain (ECD)-FC constructs used in the experiments described herein.

The present inventors have found that NOPE interacts with myostatin and other ligands and that NOPE extracellular domain (ECD)-FC constructs increase lean mass in mice when administered by either hydrodynamic tail vein transfection or as a purified protein. Administration of a NOPE, such as a NOPE ECD or variations of, may therefore be an effective treatment for conditions involving muscle injury and/or muscle wasting.

The section headings used herein are for organizational purposes only and are not to be construed as limiting the subject matter described.

Definitions

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular.

Exemplary techniques used in connection with recombinant DNA, oligonucleotide synthesis, tissue culture and transformation (e.g., electroporation, lipofection), enzymatic reactions, and purification techniques are known in the art. Many such techniques and procedures are described, e.g., in Sambrook et al. *Molecular Cloning: A Laboratory Manual* (3rd ed., Cold Spring Harbor Laboratory Press, Cold Spring Harbor, N.Y. (2001)), among other places. In addition, exemplary techniques for chemical syntheses, chemical analyses, pharmaceutical preparation, formulation, and delivery, and treatment of patients are also known in the art.

In this application, the use of "or" means "and/or" unless stated otherwise. In the context of a multiple dependent claim, the use of "or" refers back to more than one preceding independent or dependent claim in the alternative only. Unless otherwise indicated, the term "include" has the same meaning as "include, but are not limited to," the term "includes" has the same meaning as "includes, but is not limited to," and the term "including" has the same meaning as "including, but not limited to." Similarly, the term "such as" has the same meaning as the term "such as, but not limited to." Also, terms such as "element" or "component" encompass both elements and components comprising one unit and elements and components that comprise more than one subunit unless specifically stated otherwise.

As utilized in accordance with the present disclosure, the following terms, unless otherwise indicated, shall be understood to have the following meanings:

The terms "nucleic acid molecule" and "polynucleotide" may be used interchangeably, and refer to a polymer of nucleotides. Such polymers of nucleotides may contain natural and/or non-natural nucleotides, and include, but are not limited to, DNA, RNA, and PNA. "Nucleic acid sequence" refers to the linear sequence of nucleotides that comprise the nucleic acid molecule or polynucleotide.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and variant proteins are encompassed by the definition. The terms also include post-expression modifications of the polypeptide, for example, glycosylation, sialylation, acetylation, phosphorylation, and the like. Furthermore, for purposes of the present invention, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

A "native sequence" polypeptide comprises a polypeptide having the same amino acid sequence as a polypeptide found in nature. Thus, a native sequence polypeptide can have the amino acid sequence of naturally occurring polypeptide from any mammal. Such native sequence polypeptide can be isolated from nature or can be produced by recombinant or synthetic means. The term "native sequence" polypeptide specifically encompasses naturally occurring truncated or secreted forms of the polypeptide (e.g., an extracellular domain sequence), naturally occurring variant forms (e.g., alternatively spliced forms) and naturally occurring allelic variants of the polypeptide.

A polypeptide "variant" means a biologically active polypeptide having at least about 80% amino acid sequence identity with the native sequence polypeptide of SEQ ID NO: 17 after aligning the sequences and introducing gaps, if necessary, to achieve the maximum percent sequence identity, and not considering any conservative substitutions as part of the sequence identity. Such variants include, for instance, polypeptides wherein one or more amino acid residues are added, or deleted, at the N—or C-terminus of the polypeptide. In some embodiments, a variant will have at least about 80% amino acid sequence identity. In some embodiment, a variant will have at least about 90% amino acid sequence identity. In some embodiment, a variant will have at least about 95% amino acid sequence identity with the native sequence polypeptide. In some embodiment, a variant will have at least about 97% amino acid sequence identity with the native sequence polypeptide.

As used herein, "Percent (%) amino acid sequence identity" and "homology" with respect to a peptide, polypeptide sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms needed to achieve maximal alignment over the full length of the sequences being compared.

The terms "neighbor of punc E11" and "NOPE" include any native NOPE from any vertebrate source, including mammals such as primates (e.g. humans) and rodents (e.g., mice and rats), unless otherwise indicated. The term includes full-length, unprocessed NOPE as well as any form of NOPE that results from processing in the cell or any variant thereof that retains the ability to specifically bind myostatin with an affinity (Kd) of less than ≤1 µM, ≤100 nM, or ≤10 nM. The term also encompasses naturally occurring variants of NOPE, e.g., splice variants or allelic variants. In some embodiments, NOPE is a human NOPE with an amino acid sequence of SEQ ID NO: 1 (precursor, with signal peptide) or SEQ ID NO: 2 (mature, without signal peptide). A nonlimiting exemplary non-human NOPE is mouse NOPE with an amino acid sequence of SEQ ID NO: 3 (precursor, with signal peptide) or SEQ ID NO: 4 (mature, without signal peptide).

The term "NOPE extracellular domain" ("NOPE ECD") includes full-length NOPE ECDs, and NOPE ECD variants, and refers to an NOPE polypeptide that lacks the intracellular and transmembrane domains, with or without a signal peptide. In some embodiments, an NOPE ECD inhibits myostatin-mediated signaling. The term "full-length NOPE ECD", as used herein, refers to an NOPE ECD that extends to the last amino acid of the extracellular domain, and may or may not include an N-terminal signal peptide, and includes natural splice variants in the extracellular domain. In some embodiments, a full-length human NOPE ECD has the amino acid sequence of SEQ ID NO: 5 (with signal peptide) or SEQ ID NO: 6 (without signal peptide). In some embodiments, a full-length mouse NOPE ECD has the amino acid sequence of SEQ ID NO: 11 (with signal peptide) or SEQ ID NO: 12 (without signal peptide). As used herein, the term "NOPE ECD variants" refers to NOPE ECDs that contain amino acid additions, deletions, and substitutions and that remain capable of binding to myostatin. Such variants may be at least 80%, 85%, 90%, 92%, 95%, 97%, 98%, or 99% identical to the parent NOPE ECD. The % identity of two polypeptides can be measured by a similarity score determined by comparing the amino acid sequences of the two polypeptides using the Bestfit program with the default settings for determining similarity. Bestfit uses the local homology algorithm of Smith and Waterman, *Advances in Applied Mathematics* 2:482-489 (1981) to find the best segment of similarity between two sequences.

The term "NOPE ECD fusion molecule" refers to a molecule comprising an NOPE ECD, and one or more "fusion partners." In some embodiment, the NOPE ECD and the fusion partner are covalently linked ("fused"). If the fusion partner is also a polypeptide ("the fusion partner polypeptide"), the NOPE ECD and the fusion partner polypeptide may be part of a continuous amino acid sequence, and the fusion partner polypeptide may be linked to either the N-terminus or the C-terminus of the NOPE ECD. In such cases, the NOPE ECD and the fusion partner polypeptide may be translated as a single polypeptide from a coding sequence that encodes both the NOPE ECD and the fusion partner polypeptide (the "NOPE ECD fusion protein"). In some embodiments, the NOPE ECD and the fusion partner are covalently linked through other means, such as, for example, a chemical linkage other than a peptide bond. Many known methods of covalently linking polypeptides to other molecules (for example, fusion partners) may be used. In other embodiments, the NOPE ECD and the fusion partner may be fused through a "linker," which is comprised of at least one amino acid or chemical moiety.

In some embodiments, the NOPE ECD polypeptide and the fusion partner are noncovalently linked. In some such embodiments, they may be linked, for example, using binding pairs. Exemplary binding pairs include, but are not limited to, biotin and avidin or streptavidin, an antibody and its antigen, etc.

Exemplary fusion partners include, but are not limited to, an immunoglobulin Fc domain, albumin, and polyethylene glycol. The amino acid sequences of nonlimiting exemplary Fc domains are shown in SEQ ID NOs: 26 to 28.

In some embodiments, an NOPE ECD amino acid sequence is derived from that of a non-human mammal. In such embodiments, the NOPE ECD amino acid sequence may be derived from mammals including, but not limited to, rodents (including mice, rats, hamsters), rabbits, simians, felines, canines, equines, bovines, porcines, ovines, caprines, mammalian laboratory animals, mammalian farm animals, mammalian sport animals, and mammalian pets. NOPE ECD fusion molecules incorporating a non-human NOPE ECD are termed "non-human NOPE ECD fusion molecules." Similar to the human NOPE ECD fusion molecules, non-human fusion molecules may comprise a fusion partner, optional linker, and an NOPE ECD. Such non-human fusion molecules may also include a signal peptide. A "non-human NOPE ECD variant" refers to NOPE ECDs that contain amino acid additions, deletions, and substitutions and that remain capable of binding to myostatin from the animal from which the sequence was derived.

The terms "myostatin" and "MSTN" refer to mature myostatin, which, in some embodiments of human myostatin, has the sequence of SEQ ID NO: 20. A nonlimiting exemplary mouse myostatin sequence is shown in SEQ ID NO: 23. The term "pro-mysotatin" refers to the myostatin propeptide, with or without the signal sequence, which, in some embodiments of human pro-myostatin, has the sequence of SEQ ID NO: 21 (with signal sequence) or SEQ ID NO: 22 (without signal sequence). Nonlimiting exemplary mouse pro-myostatin has the sequence of SEQ ID NO: 24 (with signal sequence) or SEQ ID NO: 25 (without signal sequence).

The term "myostatin activity" or "biological activity" of myostatin, as used herein, includes any biological effect of myostatin. In some embodiments, myostatin activity includes the ability of myostatin to activate SMAD2/3. A nonlimiting exemplary assay for determining myostatin activation of SMAD2/3 is described in Example 4.

In an exemplary embodiment, a NOPE extracellular domain (ECD) reduces the amount of detectable binding of NOPE to myostatin by at least 50%. In some embodiments, a NOPE extracellular domain (ECD) polypeptide reduces the amount of detectable binding of NOPE to myostatin by at least 60%, at least 70%, at least 80%, or at least 90%.

The terms "inhibition" or "inhibit" refer to a decrease or cessation of any phenotypic characteristic or to the decrease or cessation in the incidence, degree, or likelihood of that characteristic. In some embodiments, by "reduce" or "inhibit" is meant the ability to cause a decrease of 20% or greater. In another embodiment, by "reduce" or "inhibit" is meant the ability to cause a decrease of 50% or greater. In yet another embodiment, by "reduce" or "inhibit" is meant the ability to cause an overall decrease of 75%, 85%, 90%, 95%, or greater.

In some embodiments, a NOPE extracellular domain (ECD) polypeptide is considered to "inhibit myostatin-mediated signaling" when it reduces SMAD2/3 activation with an IC50 of less than 10 nM using, e.g., the assay described in Example 4 herein. In some embodiments, A NOPE extracellular domain (ECD) polypeptide reduces SMAD2/3 activation with an IC50 of less than 5 nM, or less than 3 nM, or less than 2 nM, or less than 1 nM using e.g., the assay described in Example 4 herein.

The term "signal peptide" refers to a sequence of amino acid residues located at the N-terminus of a polypeptide that facilitates secretion of a polypeptide from a mammalian cell. A signal peptide may be cleaved upon export of the polypeptide from the mammalian cell, forming a mature protein. Signal peptides may be natural or synthetic, and they may be heterologous or homologous to the protein to which they are attached. Exemplary signal peptides include, but are not limited to, the signal peptides of NOPE and myostatin. Exemplary signal peptides also include signal peptides from heterologous proteins. A "signal sequence" refers to a polynucleotide sequence that encodes a signal peptide. In some embodiments, a NOPE ECD polypeptide or NOPE ECD fusion molecule lacks a signal peptide. In some embodiments, a NOPE ECD polypeptide or NOPE ECD fusion molecule includes at least one signal peptide, which may be a native NOPE signal peptide or a heterologous signal peptide.

The term "vector" is used to describe a polynucleotide that may be engineered to contain a cloned polynucleotide or polynucleotides that may be propagated in a host cell. A vector may include one or more of the following elements: an origin of replication, one or more regulatory sequences (such as, for example, promoters and/or enhancers) that regulate the expression of the polypeptide of interest, and/or one or more selectable marker genes (such as, for example, antibiotic resistance genes and genes that may be used in colorimetric assays, e.g., β-galactosidase). The term "expression vector" refers to a vector that is used to express a polypeptide of interest in a host cell.

A "host cell" refers to a cell that may be or has been a recipient of a vector or isolated polynucleotide. Host cells may be prokaryotic cells or eukaryotic cells. Exemplary eukaryotic cells include mammalian cells, such as primate or non-primate animal cells; fungal cells, such as yeast; plant cells; and insect cells. Nonlimiting exemplary mammalian cells include, but are not limited to, NSO cells, PER.C6® cells (Crucell), and 293 and CHO cells, and their derivatives, such as 293-6E and DG44 cells, respectively.

The term "isolated" as used herein refers to a molecule that has been separated from at least some of the components with which it is typically found in nature or has been separated from at least some of the components with which it is typically produced. For example, a polypeptide is referred to as "isolated" when it is separated from at least some of the components of the cell in which it was produced. Where a polypeptide is secreted by a cell after expression, physically separating the supernatant containing the polypeptide from the cell that produced it is considered to be "isolating" the polypeptide. Similarly, a polynucleotide is referred to as "isolated" when it is not part of the larger polynucleotide (such as, for example, genomic DNA or mitochondrial DNA, in the case of a DNA polynucleotide) in which it is typically found in nature, or is separated from at least some of the components of the cell in which it was produced, e.g., in the case of an RNA polynucleotide. Thus, a DNA polynucleotide that is contained in a vector inside a host cell may be referred to as "isolated" so long as that polynucleotide is not found in that vector in nature.

The terms "subject" and "patient" are used interchangeably herein to refer to a human. In some embodiments, methods of treating other mammals, including, but not limited to, rodents, simians, felines, canines, equines, bovines, porcines, ovines, caprines, mammalian laboratory animals, mammalian farm animals, mammalian sport animals, and mammalian pets, are also provided. In some instances, a "subject" or "patient" refers to a subject or patient in need of treatment for a disease or disorder.

The term "sample" or "patient sample" as used herein, refers to material that is obtained or derived from a subject of interest that contains a cellular and/or other molecular entity that is to be characterized and/or identified, for example based on physical, biochemical, chemical and/or physiological characteristics. For example, the phrase "disease sample" and variations thereof refers to any sample obtained from a subject of interest that would be expected or is known to contain the cellular and/or molecular entity that is to be characterized. By "tissue or cell sample" is meant a collection of similar cells obtained from a tissue of a subject or patient. The source of the tissue or cell sample may be solid tissue as from a fresh, frozen and/or preserved organ or tissue sample or biopsy or aspirate (including, for example, bronchoalveolar lavage fluid and induced sputum); blood or any blood constituents; bodily fluids such as sputum, cerebral spinal fluid, amniotic fluid, peritoneal fluid, or interstitial fluid; cells from any time in gestation or development of the subject. The tissue sample may also be primary or cultured cells or cell lines. Optionally, the tissue or cell sample is obtained from a disease tissue/organ. The tissue sample may contain compounds which are not naturally intermixed with the tissue in nature such as preservatives, anticoagulants, buffers, fixatives, nutrients, antibiotics, or the like.

A "reference sample", "reference cell", or "reference tissue", as used herein, refers to a sample, cell or tissue obtained from a source known, or believed, not to be afflicted with the disease or condition for which a method or composition of the invention is being used to identify. In one embodiment, a reference sample, reference cell or reference tissue is obtained from a healthy part of the body of the same subject or patient in whom a disease or condition is being identified using a composition or method of the invention. In one embodiment, a reference sample, reference cell or reference tissue is obtained from a healthy part of the body of at least one individual who is not the subject or patient in whom a disease or condition is being identified using a composition or method of the invention. In some embodiments, a reference sample, reference cell or reference tissue was previously obtained from a patient prior to developing a disease or condition or at an earlier stage of the disease or condition.

A condition "has previously been characterized as having [a characteristic]" when such characteristic of the condition has been shown in at least a subset of patients with the condition, or in one or more animal models of the condition. In some embodiments, such characteristic of the condition does not have to be determined in the patient to be treated with a NOPE extracellular domain (ECD) polypeptide. The presence of the characteristic in a specific patient who is to be treated using the present methods and/or compositions need not have been determined in order for the patient to be considered as having a condition that has previously been characterized as having the characteristic.

A "disorder" or "disease" is any condition that would benefit from treatment with a NOPE extracellular domain (ECD) polypeptide of the invention. This includes chronic and acute disorders or diseases including those pathological conditions which predispose the mammal to the disorder in question. Nonlimiting examples of disorders to be treated herein include cancers, autoimmune diseases, and neurodegenerative diseases.

"Muscle wasting" as used herein refers to a decrease in the mass of muscle, which, in some embodiments, accompanies a condition that directly causes muscle wasting and/or results in restricted movement, which can lead to muscle wasting. Nonlimiting examplary conditions that may be associated with muscle wasting include chronic obstructive pulmonary disease (COPD), chronic kidney disease, end stage renal disease, chronic heart failure, cancer, critical illness myopathy, critical illness polyneuropathy, stroke, spinal cord injury, spinal muscular atrophy, multiple sclerosis, progressive multifocal leukoencephalopathy, encephalomyelitis, central pontine myelolysis, adrenoleukodystrophy, Wallerian degeneration, Huntington's disease, Parkinson's disease, traumatic brain injury, Alexander's disease, Pelizaeus Merzbacher disease, globoid cell leucodystrophy, and sarcopenia.

"Muscle degenerative disorder" as used herein refers to a disorder that impairs the functioning of muscles either directly (e.g., a pathology affecting muscle) or indirectly (e.g., a pathology affecting nerves or neuromuscular junctions). Nonlimiting exemplary muscle degenerative disorders include muscular dystrophy, amyotrophic lateral sclerosis, myotonic dystrophy, polymyositis, and dermatomyositis.

"Treatment," as used herein, covers any administration or application of a therapeutic for a disease (also referred to herein as a "disorder" or a "condition") in a mammal, including a human, and includes inhibiting the disease or progression of the disease, inhibiting or slowing the disease or its progression, arresting its development, partially or fully relieving the disease, partially or fully relieving one or more symptoms of a disease, or restoring or repairing a lost, missing, or defective function; or stimulating an inefficient process.

The term "effective amount" or "therapeutically effective amount" refers to an amount of a drug effective to treat a disease or disorder in a subject. In some embodiments, an effective amount refers to an amount effective, at dosages and for periods of time necessary, to achieve the desired therapeutic or prophylactic result. A therapeutically effective amount of an NOPE extracellular domain (ECD) polypeptide of the invention may vary according to factors such as the disease state, age, sex, and weight of the individual, and the ability of the extracellular domain (ECD) polypeptide to elicit a desired response in the individual. A therapeutically effective amount encompasses an amount in which any toxic or detrimental effects of a NOPE extracellular domain (ECD) polypeptide are outweighed by the therapeutically beneficial effects.

A "prophylactically effective amount" refers to an amount effective, at dosages and for periods of time necessary, to achieve the desired prophylactic result. Typically, but not necessarily, since a prophylactic dose is used in subjects prior to or at an earlier stage of disease, the prophylactically effective amount would be less than the therapeutically effective amount.

A "pharmaceutically acceptable carrier" refers to a non-toxic solid, semisolid, or liquid filler, diluent, encapsulating material, formulation auxiliary, or carrier conventional in the art for use with a therapeutic agent that together comprise a "pharmaceutical composition" for administration to a subject. A pharmaceutically acceptable carrier is non-toxic to recipients at the dosages and concentrations employed and is compatible with other ingredients of the formulation. The pharmaceutically acceptable carrier is appropriate for the formulation employed. For example, if the therapeutic agent is to be administered orally, the carrier may be a gel capsule. If the therapeutic agent is to be administered subcutaneously, the carrier ideally is not irritable to the skin and does not cause injection site reaction.

An "article of manufacture" is any manufacture (e.g., a package or container) or kit comprising at least one reagent, e.g., a medicament for treatment of a disease or disorder, or a probe for specifically detecting a biomarker described herein. In some embodiments, the manufacture or kit is promoted, distributed, or sold as a unit for performing the methods described herein.

Therapeutic Compositions and Methods

Methods of Treating Diseases

NOPE extracellular domain (ECD) polypeptides (including NOPE ECD fusion molecules) are provided for use in methods of treating humans and other mammals. Methods of treating a disease comprising administering NOPE extracellular domain (ECD) polypeptides to humans and other mammals are provided.

Methods of Treating Muscle Wasting

The present inventors have found that NOPE ECD polypeptides and NOPE ECD fusion molecules increase muscle mass and enhance recovery following nerve crush injury in vivo. Further, the present inventors have demonstrated that NOPE binds myostatin in vitro, suggesting that NOPE ECD polypeptides and NOPE ECD fusion molecules may be acting as a myostatin ligand trap and inhibiting myostatin-mediated signaling in vivo.

In some embodiments, methods of treating muscle wasting are provided, comprising administering an effective amount of a NOPE extracellular domain (ECD) polypeptide to a subject with muscle wasting or at risk of muscle wasting. In some embodiments, methods of treating muscle wasting are provided, comprising administering an effective amount of a NOPE ECD polypeptide or NOPE ECD fusion molecule to a subject with muscle wasting or at risk of muscle wasting. In some embodiments, the subject has a condition that causes muscle wasting. In some embodiments, the subject has a condition that leads to inactivity, resulting in muscle wasting. Nonlimiting exemplary conditions associated with muscle wasting include, but are not limited to, chronic obstructive pulmonary disease (COPD), chronic kidney disease, end stage renal disease, chronic heart failure, cancer, critical illness myopathy, critical illness polyneuropathy, stroke, spinal cord injury, spinal muscular atrophy, multiple sclerosis, progressive multifocal leukoencephalopathy, encephalomyelitis, central pontine myelolysis, adrenoleukodystrophy, Wallerian degeneration, Huntington's disease, Parkinson's disease, traumatic brain injury, Alexander's disease, Pelizaeus Merzbacher disease, globoid cell leucodystrophy, and sarcopenia.

In some embodiments, methods of treating muscular injury are provided, comprising administering an effective amount of a NOPE extracellular domain (ECD) polypeptide to a subject with a muscle injury. In some embodiments, methods of treating muscular injury are provided, comprising administering an effective amount of a NOPE ECD polypeptide or NOPE ECD fusion molecule to a subject with a muscle injury. Many circumstances and events may lead to muscle injury, including, but not limited to, surgery-related muscle injury, traumatic muscle injury, work-related skeletal muscle injury, and overtraining-related muscle injury.

Non-limiting examples of surgery-related muscle injuries include muscle damage due to knee replacement, anterior cruciate ligament (ACL) repair, plastic surgery, hip replacement surgery, joint replacement surgery, tendon repair surgery, surgical repair of rotator cuff disease and injury, and amputation.

Non-limiting examples of traumatic muscle injuries include battlefield muscle injuries, auto accident-related muscle injuries, and sports-related muscle injuries. Traumatic injury to the muscle can include lacerations, blunt force contusions, shrapnel wounds, muscle pulls or tears, burns, acute strains, chronic strains, weight or force stress injuries, repetitive stress injuries, avulsion muscle injury, and compartment syndrome.

In some embodiments, the muscle injury is a traumatic muscle injury and the treatment method provides for administration of at least one high dose of a compound of the invention immediately after the traumatic injury (for example, within one day of the injury) followed by periodic administration of a low dose of a compound of the invention during the recovery period.

Non-limiting examples of work-related muscle injuries include injuries caused by highly repetitive motions, forceful motions, awkward postures, prolonged and forceful mechanical coupling between the body and an object, and vibration. Overtraining-related muscle injuries include unrepaired or under-repaired muscle damage coincident with a lack of recovery or lack of an increase of physical work capacity. In an additional embodiment, the muscle injury is exercise or sports-induced muscle damage resulting including exercise-induced delayed onset muscle soreness (DOMS).

In some embodiments, methods of treating a muscle degenerative disorder are provided, comprising administering an effective amount of a NOPE extracellular domain (ECD) polypeptide to a subject with a muscle degenerative disorder. In some embodiments, methods of treating a muscle degenerative disorder are provided, comprising administering an effective amount of a NOPE ECD polypeptide or NOPE ECD fusion molecule to a subject with a muscle degenerative disorder. In some embodiments, the subject with the muscle degenerative disorder has experienced muscle wasting. In some embodiments, the subject with the muscle degenerative disorder has been diagnosed with the disorder, but has not yet experienced significant or detectable muscle wasting. Nonlimiting exemplary muscle degenerative disorders include, but are not limited to, muscular dystrophy, myotonic dystrophy, polymyositis, and dermatomyositis. Nonlimiting exemplary muscular dystrophies include, but are not limited to, Duchenne muscular dystrophy, Becker muscular dystrophy, congenital muscular dystrophy (Fukuyama), Emery Dreifuss muscular dystrophy, limb girdle muscular dystrophy, and fascioscapulohumeral muscular dystrophy. Nonlimiting exemplary myotonic dystrophies include, but are not limited to, myotonic dystrophy type I, myotonic dystrophy type II, and congenical myotonia.

In some embodiments, treating muscle wasting, muscular injury, or a muscle degenerative disorder comprises at least one of: delaying progression of muscle wasting, improving the subject's 6 minute walking distance (6 MWD), reducing physical decline, delaying occurrence of life-changing events, improving independence, reducing hospitalizations, and delaying the need for an assisted living arrangement. In some embodiments, improving the subject's 6 minute walking distance (6 MWD) means that the subject's 6 MWD has increased by at least 10 meters, or at least 20 meters, or at least 30 meters after 12 months of treatment. In another embodiment, preservation of a subject's 6 MWD would indicate good efficacy in some disorders (e.g., Duchenne muscular dystrophy). Nonlimiting exemplary life-changing events include being placed on a ventilator and/or needing a wheelchair.

In some embodiments, methods of treating amyotrophic lateral sclerosis (ALS) are provided, comprising administering an effective amount of a NOPE extracellular domain (ECD) polypeptide to a subject with ALS. In some embodiments, methods of treating a muscle degenerative disorder are provided, comprising administering an effective amount of a NOPE ECD polypeptide or NOPE ECD fusion molecule to a subject with ALS. A method is considered to treat ALS, in some embodiments, when it results in at least one of: delaying progression of ALS, reducing physical decline, improving forced vital capacity, slowing the decline in forced vital capacity, slowing the decline in the subject's score on the ALS functional rating scale (ALSFRS), improving the subject's score on the ALSFRS, delaying occurrence of life-changing events, and improving the subject's time of survival. In some embodiments, a method is considered to treat ALS when it results in delaying a tracheostomy and/or delaying placement of a percutaneous endoscopic gastrostomy (PEG).

Routes of Administration and Carriers

In various embodiments, NOPE agonists may be administered subcutaneously or intravenously. In some embodiments, NOPE extracellular domain (ECD) polypeptide may be administered in vivo by various routes, including, but not limited to, oral, intra-arterial, parenteral, intranasal, intramuscular, intracardiac, intraventricular, intratracheal, buccal, rectal, intraperitoneal, by inhalation, intradermal, topical, transdermal, and intrathecal, or otherwise, e.g., by implantation. The subject compositions may be formulated into preparations in solid, semi-solid, liquid, or gaseous forms; including, but not limited to, tablets, capsules, powders, granules, ointments, solutions, suppositories, enemas, injections, inhalants, and aerosols. In some embodiments, a NOPE extracellular domain (ECD) polypeptide is delivered using gene therapy. As a nonlimiting example, a nucleic acid molecule encoding a NOPE extracellular domain (ECD) polypeptide may be coated onto gold microparticles and delivered intradermally by a particle bombardment device, or "gene gun," e.g., as described in the literature (see, e.g., Tang et al., *Nature* 356:152-154 (1992)).

In various embodiments, compositions comprising a NOPE extracellular domain (ECD) polypeptide (such as NOPE ECD fusion molecule) is provided in formulations with a wide variety of pharmaceutically acceptable carriers (see, e.g., Gennaro, *Remington: The Science and Practice of Pharmacy with Facts and Comparisons: Drugfacts Plus*, 20th ed. (2003); Ansel et al., *Pharmaceutical Dosage Forms and Drug Delivery Systems*, $7^{th}$ ed., Lippencott Williams and Wilkins (2004); Kibbe et al., *Handbook of Pharmaceutical Excipients*, $3^{rd}$ ed., Pharmaceutical Press (2000)). Various pharmaceutically acceptable carriers, which include vehicles, adjuvants, and diluents, are available. Moreover, various pharmaceutically acceptable auxiliary substances, such as pH adjusting and buffering agents, tonicity adjusting agents, stabilizers, wetting agents and the like, are also available. Nonlimiting exemplary carriers include saline, buffered saline, dextrose, water, glycerol, ethanol, and combinations thereof.

In various embodiments, compositions comprising a NOPE extracellular domain (ECD) polypeptide may be formulated for injection, including subcutaneous administration, by dissolving, suspending, or emulsifying them in an aqueous or nonaqueous solvent, such as vegetable or other oils, synthetic aliphatic acid glycerides, esters of higher aliphatic acids, or propylene glycol; and if desired, with conventional additives such as solubilizers, isotonic agents, suspending agents, emulsifying agents, stabilizers and preservatives. In various embodiments, the compositions may be formulated for inhalation, for example, using pressurized acceptable propellants such as dichlorodifluoromethane, propane, nitrogen, and the like. The compositions may also be formulated, in various embodiments, into sustained release microcapsules, such as with biodegradable or non-biodegradable polymers. A nonlimiting exemplary biodegradable formulation includes poly lactic acid-glycolic acid polymer. A nonlimiting exemplary non-biodegradable formulation includes a polyglycerin fatty acid ester. Certain methods of making such formulations are described, for example, in EP 1 125 584 A1.

Pharmaceutical dosage packs comprising one or more containers, each containing one or more doses of a NOPE extracellular domain (ECD) polypeptide, are also provided. In some embodiments, a unit dosage is provided wherein the unit dosage contains a predetermined amount of a composition comprising a NOPE extracellular domain (ECD) polypeptide, with or without one or more additional agents. In some embodiments, such a unit dosage is supplied in single-use prefilled syringe for injection. In various embodiments, the composition contained in the unit dosage may comprise saline, sucrose, or the like; a buffer, such as phosphate, or the like; and/or be formulated within a stable and effective pH range. Alternatively, in some embodiments, the composition may be provided as a lyophilized powder that may be reconstituted upon addition of an appropriate liquid, for example, sterile water. In some embodiments, the composition comprises one or more substances that inhibit protein aggregation, including, but not limited to, sucrose and arginine. In some embodiments, a composition of the invention comprises heparin and/or a proteoglycan.

Pharmaceutical compositions are administered in an amount effective for treatment or prophylaxis of the specific indication. The therapeutically effective amount is typically dependent on the weight of the subject being treated, his or her physical or health condition, the extensiveness of the condition to be treated, or the age of the subject being treated. In some embodiments, a NOPE extracellular domain (ECD) polypeptide may be administered in an amount in the range of about 50 µg/kg body weight to about 50 mg/kg body weight per dose. In some embodiments, a NOPE extracellular domain (ECD) polypeptide may be administered in an amount in the range of about 100 µg/kg body weight to about 50 mg/kg body weight per dose. In some embodiments, a NOPE extracellular domain (ECD) polypeptide may be administered in an amount in the range of about 100 µg/kg body weight to about 20 mg/kg body weight per dose. In some embodiments, a NOPE extracellular domain (ECD) polypeptide may be administered in an amount in the range of about 0.5 mg/kg body weight to about 20 mg/kg body weight per dose.

In some embodiments, a NOPE extracellular domain (ECD) polypeptide may be administered in an amount in the range of about 10 mg to about 1,000 mg per dose. In some embodiments, a NOPE extracellular domain (ECD) polypeptide may be administered in an amount in the range of about 20 mg to about 500 mg per dose. In some embodiments, a NOPE extracellular domain (ECD) polypeptide may be administered in an amount in the range of about 20 mg to about 300 mg per dose. In some embodiments, a NOPE extracellular domain (ECD) polypeptide may be administered in an amount in the range of about 20 mg to about 200 mg per dose.

The NOPE extracellular domain (ECD) polypeptide compositions may be administered as needed to subjects. In some embodiments, an effective dose of a NOPE extracellular domain (ECD) polypeptide is administered to a subject one or more times. In various embodiments, an effective dose of a NOPE extracellular domain (ECD) polypeptide is administered to the subject once a month, less than once a month, such as, for example, every two months, every three months, or every six months. In other embodiments, an effective dose of a NOPE extracellular domain (ECD) polypeptide is administered more than once a month, such as, for example, every two weeks, every week, twice per week, three times per week, daily, or multiple times per day. An effective dose of a NOPE extracellular domain (ECD) polypeptide is administered to the subject at least once. In some embodiments, the effective dose of a NOPE extracellular domain (ECD) polypeptide may be administered multiple times, including for periods of at least a month, at least six months, or at least a year. In some embodiments, a NOPE extracellular domain (ECD) polypeptide is administered to a subject as-needed to alleviate one or more symptoms of a condition.

Combination Therapy

A NOPE extracellular domain (ECD) polypeptide according to the invention, including any functional variants thereof, may be administered to a subject in need thereof in combination with other biologically active substances or other treatment procedures for the treatment of diseases. For example, NOPE extracellular domain (ECD) polypeptide may be administered alone or with other modes of treatment. They may be provided before, substantially contemporaneous with, or after other modes of treatment.

In some embodiments, a NOPE extracellular domain (ECD) polypeptide is administered to a subject before, during, or after another mode of treatment, such as exercise and/or physical therapy, or surgery.

For treatment of certain muscular dystrophies, such as Duchenne muscular dystrophy, a method of treatment with a NOPE extracellular domain (ECD) polypeptide may further comprise administering a corticosteroid. For treatment of certain myotonic dystrophies, a method of treatment with a NOPE extracellular domain (ECD) polypeptide may further comprise administering a therapeutic agent selected from phenytoin, procainamide, and quinine For treatment of amyotrophic lateral sclerosis (ALS), a method of treatment with a NOPE extracellular domain (ECD) polypeptide may further comprise administering riluzole.

NOPE Extracellular Domains (ECDs)

Nonlimiting exemplary NOPE ECDs include full-length NOPE ECDs, and NOPE ECD variants. NOPE ECDs bind to myostatin. In some embodiments, an NOPE ECD inhibits myostatin-mediated activation of SMAD2/3. NOPE ECDs may include or lack a signal peptide. Exemplary NOPE ECDs include, but are not limited to, human NOPE ECDs having amino acid sequences selected from SEQ ID NOs: 5 (with signal peptide) and 6 (without signal peptide), and SEQ ID NO: 8.

NOPE ECD variants include variants comprising one or more amino acid additions, deletions, and/or substitutions, and that remain capable of binding myostatin. In some embodiments, an NOPE ECD variant sequence is at least 80%, 85%, 90%, 92%, 95%, 97%, 98%, or 99% identical to the corresponding sequence of the parent NOPE ECD.

Fusion Partners and Conjugates

In some embodiments, a NOPE ECD of the present invention may be combined with a fusion partner polypeptide, resulting in a fusion protein. These fusion partner polypeptides may facilitate purification, and may show an increased half-life in vivo. Fusion partner polypeptides that have a disulfide-linked dimeric structure due to the IgG portion may also be more efficient in binding and neutralizing other molecules than the monomeric NOPE ECD fusion protein or the NOPE ECD alone. Other suitable fusion partners for NOPE ECDs include, for example, polymers, such as water soluble polymers, the constant domain of immunoglobulins; all or part of human serum albumin (HSA); fetuin A; fetuin B; a leucine zipper domain; a tetranectin trimerization domain; mannose binding protein (also known as mannose binding lectin), for example, mannose binding protein 1; and an Fc region, as described herein and further described in U.S. Pat. No. 6,686,179.

A fusion molecule may be prepared by attaching polyaminoacids or branch point amino acids to the NOPE ECD. For example, the polyaminoacid may be a carrier protein that serves to increase the circulation half-life of the NOPE ECD (in addition to the advantages achieved via a fusion molecule). For the therapeutic purpose of the present invention, such polyaminoacids should ideally be those that do not create neutralizing antigenic response, or other adverse responses. Such polyaminoacids may be chosen from serum album (such as HSA), fetuin A, fetuin B, leucine zipper nuclear factor erythroid derivative-2 (NFE2), neuroretinal leucine zipper, tetranectin, or other polyaminoacids, for example, lysines. As described herein, the location of attachment of the polyaminoacid may be at the N-terminus or C-terminus, or other places in between, and also may be connected by a chemical linker moiety to the selected molecule.

Polymers

Polymers, for example, water soluble polymers, may be useful in the present invention to reduce precipitation of the NOPE ECD to which the polymer is attached in an aqueous environment, such as typically found in a physiological environment. Polymers employed in the invention will be pharmaceutically acceptable for the preparation of a therapeutic product or composition.

Suitable, clinically acceptable, water soluble polymers include, but are not limited to, polyethylene glycol (PEG), polyethylene glycol propionaldehyde, copolymers of ethylene glycol/propylene glycol, monomethoxy-polyethylene glycol, carboxymethylcellulose, dextran, polyvinyl alcohol (PVA), polyvinyl pyrrolidone, poly-1,3-dioxolane, poly-1,3,6-trioxane, ethylene/maleic anhydride copolymer, poly (β-amino acids) (either homopolymers or random copolymers), poly(n-vinyl pyrrolidone) polyethylene glycol, polypropylene glycol homopolymers (PPG) and other polyakylene oxides, polypropylene oxide/ethylene oxide copolymers, polyoxyethylated polyols (POG) (e.g., glycerol) and other polyoxyethylated polyols, polyoxyethylated sorbitol, or polyoxyethylated glucose, colonic acids or other carbohydrate polymers, Ficoll, or dextran and mixtures thereof.

Polymers used herein, for example water soluble polymers, may be of any molecular weight and may be branched or unbranched. In some embodiments, the polymers have an average molecular weight of between 2 kDa and 100 kDa, between 5 kDa and 50 kDa, or between 12 kDa and 25 kDa. Generally, the higher the molecular weight or the more branches, the higher the polymer:protein ratio. Other sizes may also be used, depending on the desired therapeutic profile; for example, the duration of sustained release; the effects, if any, on biological activity; the ease in handling; the degree or lack of antigenicity; and other known effects of a polymer on a NOPE ECD of the invention.

In some embodiments, the present invention contemplates the chemically derivatized NOPE ECD to include mono- or poly- (e.g., 2-4) PEG moieties. Pegylation may be carried out by any of the pegylation reactions available. There are a number of PEG attachment methods available to those skilled in the art. See, for example, EP 0 401 384; Malik et al., *Exp. Hematol.*, 20:1028-1035 (1992); Francis, *Focus on Growth Factors*, 3(2):4-10 (1992); EP 0 154 316; EP 0 401 384; WO 92/16221; WO 95/34326; Chamow, *Bioconjugate Chem.*, 5:133-140 (1994); U.S. Pat. No. 5,252,714; and the other publications cited herein that relate to pegylation.

Markers

NOPE ECDs of the present invention may be fused to marker sequences, such as a peptide that facilitates purification of the fused polypeptide. The marker amino acid sequence may be a hexa-histidine peptide such as the tag provided in a pQE vector (Qiagen, Mississauga, Ontario, Canada), among others, many of which are commercially available. As described in Gentz et al., *Proc. Natl. Acad. Sci.* 86:821-824 (1989), for instance, hexa-histidine provides for convenient purification of the fusion protein. Another peptide tag useful for purification, the hemagglutinin (HA) tag, corresponds to an epitope derived from the influenza HA protein. (Wilson et al., *Cell* 37:767 (1984)). Any of these above fusions may be engineered using the NOPE ECD of the present invention.

Oligomerization Domain Fusion Partners

In various embodiments, oligomerization offers some functional advantages to a fusion protein, including, but not limited to, multivalency, increased binding strength, and the combined function of different domains. Accordingly, in some embodiments, a fusion partner comprises an oligomerization domain, for example, a dimerization domain. Exemplary oligomerization domains include, but are not limited to, coiled-coil domains, including alpha-helical coiled-coil domains; collagen domains; collagen-like domains; and certain immunoglobulin domains. Exemplary coiled-coil polypeptide fusion partners include, but are not limited to, the tetranectin coiled-coil domain; the coiled-coil domain of cartilage oligomeric matrix protein; angiopoietin coiled-coil domains; and leucine zipper domains. Exemplary collagen or collagen-like oligomerization domains include, but are not limited to, those found in collagens, mannose binding lectin, lung surfactant proteins A and D, adiponectin, ficolin, conglutinin, macrophage scavenger receptor, and emilin.

Antibody Fc Immunoglobulin Domain Fusion Partners

Many Fc domains that may be used as fusion partners are known in the art. In some embodiments, a fusion partner is an Fc immunoglobulin domain. An Fc fusion partner may be a wild-type Fc found in a naturally occurring antibody, or a variant thereof. Nonlimiting exemplary Fc fusion partners include Fcs comprising a hinge and the CH2 and CH3 constant domains of a human IgG, for example, human IgG1, IgG2, IgG3, or IgG4. In some embodiments, an Fc fusion partner comprises a C237S mutation, for example, in an IgG1 constant region. See, e.g., SEQ ID NO: 17. In some embodiments, an Fc fusion partner is a human IgG4 constant region. In some such embodiments, the human IgG4 constant region comprises an S241P mutation. See, e.g., Angal et al. *Mol. Immunol.* 30(1): 105-108 (1993). In some embodiments, an Fc fusion partner comprises a hinge, CH2, and CH3 domains of human IgG2 with a P331S mutation, as described in U.S. Pat. No. 6,900,292. Additional exemplary Fc fusion partners also include, but are not limited to, human IgA and IgM. Certain exemplary Fc domain fusion partners are shown in SEQ ID NOs: 26 to 28.

In some embodiments, effector function is not desirable. For example, in some embodiments, effector function may not be desirable in treatments of inflammatory conditions and/or autoimmune disorders. In some such embodiments, a human IgG4 or IgG2 heavy chain constant region is selected or engineered. In some embodiments, an IgG4 constant region comprises an S241P mutation.

Albumin Fusion Partners and Albumin-binding Molecule Fusion Partners

In some embodiments, a fusion partner is an albumin. Exemplary albumins include, but are not limited to, human serum album (HSA) and fragments of HSA that are capable of increasing the serum half-life or bioavailability of the polypeptide to which they are fused. In some embodiments, a fusion partner is an albumin-binding molecule, such as, for example, a peptide that binds albumin or a molecule that conjugates with a lipid or other molecule that binds albumin. In some embodiments, a fusion molecule comprising HSA is prepared as described, e.g., in U.S. Pat. No. 6,686,179.

Exemplary Attachment of Fusion Partners

The fusion partner may be attached, either covalently or non-covalently, to the N-terminus or the C-terminus of the NOPE ECD. The attachment may also occur at a location within the NOPE ECD other than the N-terminus or the C-terminus, for example, through an amino acid side chain (such as, for example, the side chain of cysteine, lysine, serine, or threonine).

In either covalent or non-covalent attachment embodiments, a linker may be included between the fusion partner and the NOPE ECD. Such linkers may be comprised of at least one amino acid or chemical moiety. Exemplary methods of covalently attaching a fusion partner to a NOPE ECD include, but are not limited to, translation of the fusion partner and the NOPE ECD as a single amino acid sequence and chemical attachment of the fusion partner to the NOPE ECD. When the fusion partner and NOPE ECD are translated as single amino acid sequence, additional amino acids may be included between the fusion partner and the NOPE ECD as a linker. In some embodiments, the linker is selected based on the polynucleotide sequence that encodes it, to facilitate cloning the fusion partner and/or NOPE ECD into a single expression construct (for example, a polynucleotide containing a particular restriction site may be placed between the polynucleotide encoding the fusion partner and the polynucleotide encoding the NOPE ECD, wherein the polynucleotide containing the restriction site encodes a short amino acid linker sequence). When the fusion partner and the NOPE ECD are covalently coupled by chemical means, linkers of various sizes may typically be included during the coupling reaction.

Exemplary methods of non-covalently attaching a fusion partner to a NOPE ECD include, but are not limited to, attachment through a binding pair. Exemplary binding pairs include, but are not limited to, biotin and avidin or streptavidin, an antibody and its antigen, etc.

Exemplary Properties of NOPE ECDs and NOPE ECD Fusion Molecules

In some embodiments, a NOPE ECD or a NOPE ECD fusion molecule binds to myostatin, and inhibits myostatin-mediated SMAD2/3 activation. In some embodiments, NOPE ECD fusion molecule binds to myostatin with a binding affinity ($K_D$) of less than 50 nM, less than 20 nM, less than 10 nM, less than 1 nM, or less than 0.1 nM. In some embodiments, a NOPE ECD fusion molecule blocks binding of myostatin to native NOPE.

Signal Peptides

In order for some secreted proteins to express and secrete in large quantities, a signal peptide from a heterologous protein may be desirable. Employing heterologous signal peptides may be advantageous in that a resulting mature polypeptide may remain unaltered as the signal peptide is removed in the ER during the secretion process. The addition of a heterologous signal peptide may be required to express and secrete some proteins.

Nonlimiting exemplary signal peptide sequences are described, e.g., in the online Signal Peptide Database maintained by the Department of Biochemistry, National University of Singapore. See Choo et al., *BMC Bioinformatics*, 6: 249 (2005); and PCT Publication No. WO 2006/081430.

Co-translational and Post-translational Modifications

In some embodiments, a polypeptide such as a NOPE ECD, is differentially modified during or after translation, for example by glycosylation, sialylation, acetylation, phosphorylation, amidation, derivatization by known protecting/blocking groups, proteolytic cleavage, or linkage to an antibody molecule or other cellular ligand. Any of numerous chemical modifications may be carried out by known techniques, including, but not limited to, specific chemical cleavage by cyanogen bromide, trypsin, chymotrypsin, papain, V8 protease; $NABH_4$, acetylation; formylation; oxidation; reduction; and/or metabolic synthesis in the presence of tunicamycin.

Additional post-translational modifications encompassed by the invention include, for example, N-linked or O-linked carbohydrate chains; processing of N-terminal or C-terminal ends; attachment of chemical moieties to the amino acid backbone; chemical modifications of N-linked or O-linked carbohydrate chains; and addition or deletion of an N-terminal methionine residue as a result of prokaryotic host cell expression.

Nucleic Acid Molecules Encoding NOPE extracellular domain (ECD) Polypeptide

In some embodiments, nucleic acid molecules comprising polynucleotides that encode NOPE ECDs or NOPE ECD fusion molecules are provided. Nucleic acid molecules comprising polynucleotides that encode NOPE ECD fusion molecules in which the NOPE ECD and the fusion partner are translated as a single polypeptide are also provided.

In some embodiments, a polynucleotide encoding a NOPE ECD comprises a nucleotide sequence that encodes a signal peptide, which, when translated, will be fused to the N-terminus of the NOPE ECD. As discussed above, the signal peptide may be the native NOPE signal peptide, or may be another heterologous signal peptide. In some embodiments, the nucleic acid molecule comprising the polynucleotide encoding the gene of interest is an expression vector that is suitable for expression in a selected host cell.

Nucleic acid molecules may be constructed using recombinant DNA techniques conventional in the art. In some embodiments, a nucleic acid molecule is an expression vector that is suitable for expression in a selected host cell.

Polypeptide Expression and Production Vectors

Vectors comprising polynucleotides that encode NOPE ECDs are provided. Vectors comprising polynucleotides that encode NOPE ECD fusion molecules are also provided. Such vectors include, but are not limited to, DNA vectors, phage vectors, viral vectors, retroviral vectors, etc.

In some embodiments, a vector is selected that is optimized for expression of polypeptides in CHO or CHO-derived cells, or in NSO cells. Exemplary such vectors are described, e.g., in Running Deer et al., *Biotechnol. Prog.* 20:880-889 (2004).

In some embodiments, a vector is chosen for in vivo expression of a NOPE extracellular domain (ECD) polypeptide in animals, including humans. In some such embodiments, expression of the polypeptide or polypeptides is under the control of a promoter or promoters that function in a tissue-specific manner. For example, liver-specific promoters are described, e.g., in PCT Publication No. WO 2006/076288.

Host Cells

In various embodiments, NOPE ECDs and/or fusion molecules comprising any of those may be expressed in prokaryotic cells, such as bacterial cells; or in eukaryotic cells, such as fungal cells, plant cells, insect cells, and mammalian cells. Such expression may be carried out, for example, according to procedures known in the art. Exemplary eukaryotic cells that may be used to express polypeptides include, but are not limited to, COS cells, including COS 7 cells; 293 cells, including 293-6E cells; CHO cells, including CHO-S and DG44 cells; PER.C6® cells (Crucell); and NSO cells. In some embodiments, a particular eukaryotic host cell is selected based on its ability to make desired post-translational modifications to NOPE ECDs, and/or fusion molecules. For example, in some embodiments, CHO cells produce polypeptides that have a higher level of sialylation than the same polypeptide produced in 293 cells.

Introduction of one or more nucleic acids into a desired host cell may be accomplished by any method, including but not limited to, calcium phosphate transfection, DEAE-dextran mediated transfection, cationic lipid-mediated transfection, electroporation, transduction, infection, etc. Nonlimiting exemplary methods are described, e.g., in Sambrook et al., *Molecular Cloning, A Laboratory Manual*, $3^{rd}$ ed. Cold Spring Harbor Laboratory Press (2001). Nucleic acids may be transiently or stably transfected in the desired host cells, according to any suitable method.

In some embodiments, one or more polypeptides may be produced in vivo in an animal that has been engineered or transfected with one or more nucleic acid molecules encoding the polypeptides, according to any suitable method.

Purification of Polypeptides

NOPE ECDs, and fusion molecules comprising any of those may be purified by any suitable method. Such methods include, but are not limited to, the use of affinity matrices or hydrophobic interaction chromatography. Suitable affinity ligands include any ligands that bind to NOPE (such as myostatin) or that bind to the fusion partner. Further, a Protein A, Protein G, Protein A/G, or an antibody affinity column may be used to bind to an Fc fusion partner to purify a fusion molecule.

In some embodiments, hydrophobic interactive chromatography, for example, a butyl or phenyl column, is also used for purifying some polypeptides. Many methods of purifying polypeptides are known in the art.

Articles of Manufacture

In some embodiments, an article of manufacture or a kit containing materials useful for the detection of a biomarker (e.g., NOPE or myostatin) or for the treatment, prevention and/or diagnosis of the disorders described above is provided. The article of manufacture comprises a container and a label or package insert on or associated with the container. Suitable containers include, for example, bottles, vials, syringes, etc. The containers may be formed from a variety of materials such as glass or plastic. In some embodiments, the container holds a composition which is by itself or combined with another composition effective for treating, preventing and/or diagnosing the condition and may have a sterile access port (for example the container may be an intravenous solution bag or a vial having a stopper pierceable by a hypodermic injection needle). The label or package insert indicates that the composition is used for treating the condition of choice. In some embodiments, the article of manufacture may comprise (a) a first container with a composition contained therein, wherein the composition comprises a NOPE extracellular domain (ECD) polypeptide of the invention; and (b) a second container with a composition contained therein, wherein the composition comprises an additional therapeutic agent. The article of manufacture may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In some embodiments, the molecules of the present invention can be packaged alone or in combination with other therapeutic compounds as a kit. In one embodiment, the therapeutic compound is an anti-cancer agent. In another embodiment, the therapeutic compound is an immunosuppressive agent. The kit can include optional components that aid in the administration of the unit dose to patients, such as vials for reconstituting powder forms, syringes for injection, customized IV delivery systems, inhalers, etc. Additionally, the unit dose kit can contain instructions for preparation and administration of the compositions. The kit may be manufactured as a single use unit dose for one patient, multiple uses for a particular patient (at a constant dose or in which the individual compounds may vary in potency as therapy progresses); or the kit may contain multiple doses suitable for administration to multiple patients ("bulk packaging").

The kit components may be assembled in cartons, blister packs, bottles, tubes, and the like.

EXAMPLES

The examples discussed below are intended to be purely exemplary of the invention and should not be considered to limit the invention in any way. The examples are not intended to represent that the experiments below are all or the only experiments performed. Efforts have been made to ensure accuracy with respect to numbers used (for example, amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Construction, Expression and Purification of Certain NOPE-ECD Fusion Proteins

Figure 1:
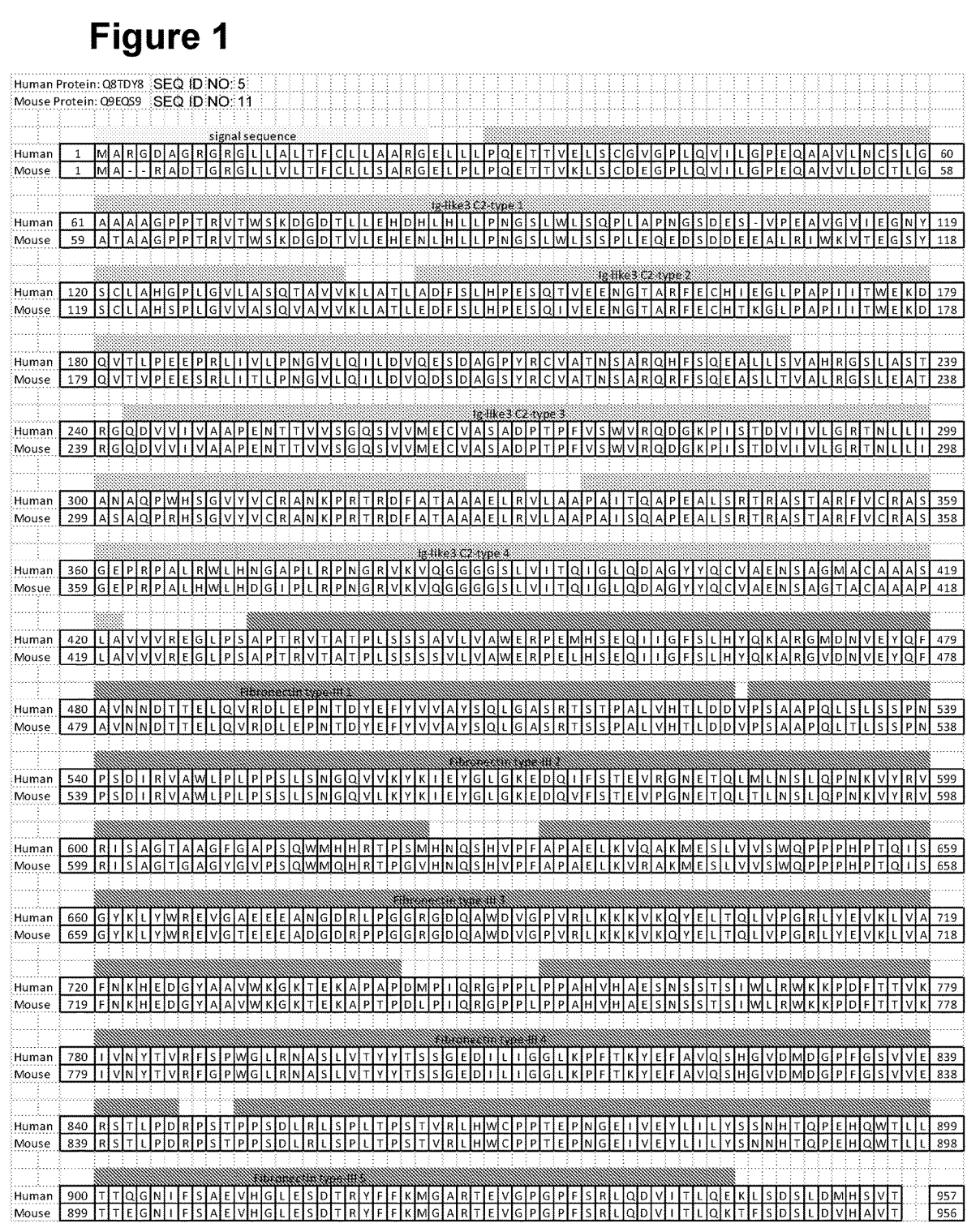

Constructs encoding human NOPE (Gene ID 57722) and mouse NOPE (Gene ID 56741) extracellular domain (ECD)-Fc fusion molecules were cloned into and expressed from vector pTT5 (Biotechnology Research Institute, Montreal, Canada). Truncated derivatives of the human or mouse NOPE ECD-Fc fusion molecule were constructed using PCR and conventional mutagenesis techniques. The primary protein sequence and domain structure of the human and mouse NOPE ECD-Fc moiety in the parental construct is shown in FIG. 1. Truncated NOPE ECD-Fc derivatives were created to define domains important for the function of NOPE. FIG. 2 lists the various NOPE-Fc Fusion proteins used in these examples with names and brief descriptions.

For in vivo confirmation experiments (e.g., Example 2), mNOPE (23-956) ECD-Fc containing a human CD33 signal sequence in place of the native signal sequence was cloned into a Bacmam vector for secreted expression in CHO or HEK cells via Bacmam technology. The secreted protein was purified using MabSelectSure Protein A affinity followed by Superdex-200 size exclusion chromatograpy. For in vitro binding experiments (Example 3), production of NOPE-ECD-Fc and its' derivatives was achieved by PEI mediated transient transfection of CHO-3E7 cells grown in CD DG44 (Invitrogen, Grand Island, N.Y.). The secreted proteins were purified over a HiTrap Protein A column (GE Healthcare, Pittsburg, Pa.).

Example 2

NOPE Increases Muscle Mass In Vivo

Figure 3:
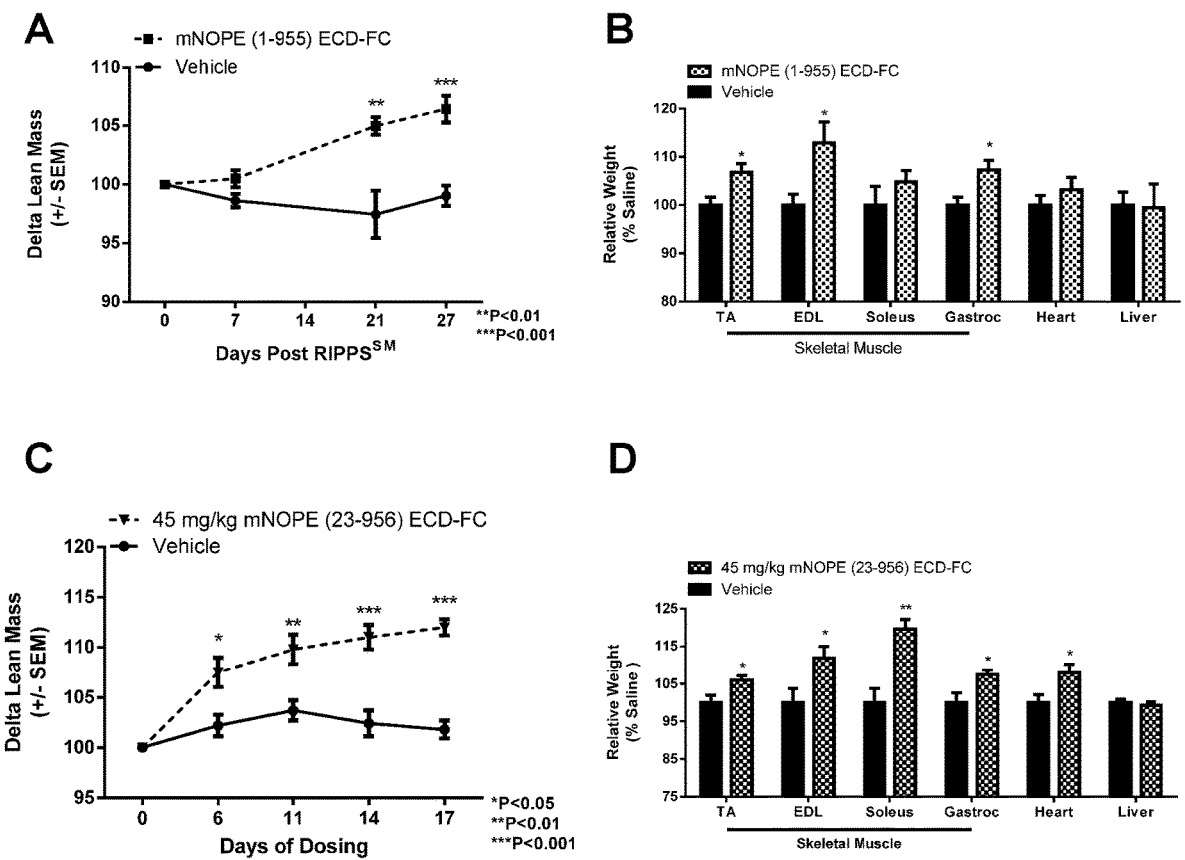
FIG. 3A-D show (A, B) the change in lean mass in mice administered NOPE ECD-FC by hydrodynamic tail vein transfection, (C, D) the change in lean mass in mice administered purified NOPE ECD-FC protein, as described in Example 2. TA=tibialis anterior muscle; EDL=extensor digitorum longus muscle; gastroc=gastrocnemius muscle.

Experiments were carried out to determine whether hydrodynamic tail vein injection of a DNA vector encoding mNOPE (1-955) ECD-FC has an impact on muscle growth in vivo. Female BalbC mice (Charles River Labs, Wilmington, Mass.) were randomly assigned into 2 treatment groups of 10 mice each. On day 0, mice were subject to lean mass analysis (EchoMRI®, Houston, Tex.) to establish baseline measurements. Once baseline measurements were recorded, mice were hydrodynamically transfected with mNOPE (1-955) ECD-FC or Vehicle control. On day 7, 21, 27, lean mass was measured. mNOPE (1-955) ECD-FC exposure demonstrated anabolic effects in lean mass within 7 days of dosing (FIG. 3A). The increase in lean mass persisted throughout the course of the study. After 27 days, lean mass organs were harvested and weighed to confirm that the increase in lean mass was muscle specific. The lean mass anabolism translated to a significant increase in skeletal muscle in animals exposed to mNOPE (1-955) ECD-FC, however, liver, a non-muscle lean organ, was not affected (FIG. 3B).

We confirmed these findings with purified protein. mNOPE (23-956) ECD-FC was constructed, transiently expressed and purified as described in Example 1. Female BalbC mice (Charles River Labs, Wilmington, Mass.) were randomly assigned into 2 treatment groups of 10 mice each. On day 0, mice were subject to lean mass analysis as outlined above to establish baseline measurements. Once baseline measurements were recorded, mice were administered vehicle or 45 mg/kg purified recombinant mNOPE (23-956) ECD-FC protein twice per week. On day 6, 11, 14, and 17, lean mass was measured. NOPE exposure demonstrated an anabolic effect in lean mass within 6 days of the first dose (FIG. 3C). The increase in lean mass persisted throughout the course of the study. After 17 days, organs were harvested and weighed. The lean mass anabolism translated to a significant increase in skeletal muscle and heart weight in animals exposed to mNOPE (23-956) ECD-FC, while liver remained unchanged (FIG. 3D). These results confirm our observations by hydrodynamic transfection that systemic exposure to NOPE leads to muscle anabolism in mice.

Example 3

NOPE Binds Myostatin In Vitro

Biacore® T100 surface plasmon resonance (SPR) technology (GE, NY, USA) was used to determine the affinity of human and mouse NOPE-FC for Myostatin and Pro-Myostatin (R&D Systems, Minneapolis, Minn.). Myostatin was selected to determine if one mechanism of promoting muscle growth in vivo was through acting as myostatin ligand trap in circulation. hNOPE (1-957) ECD-FCand mNOPE (1-955) ECD-FC were constructed, transiently expressed and purified as described in example 1.

Figure 4:
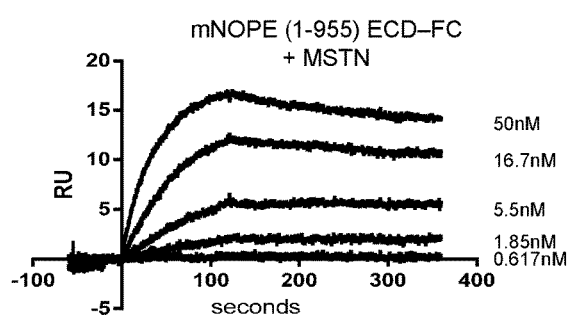
FIG. 4A-E show mouse NOPE ECD-FC binding to myostatin (A) but not to pro-myostatin (B); human NOPE ECD-FC binding to myostatin (C); and ActR2b-FC, a myostatin inhibitor, binding to myostatin (D). The association constant, dissociation constant, and affinity of each protein for myostatin is shown in (E), as described in Example 3.
Figure 4:
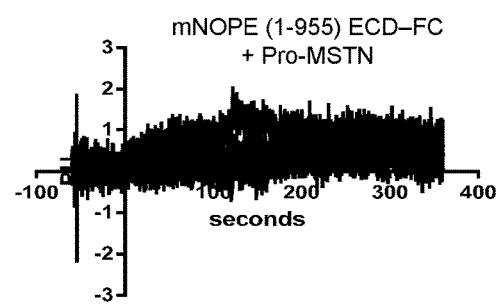
Figure 4:
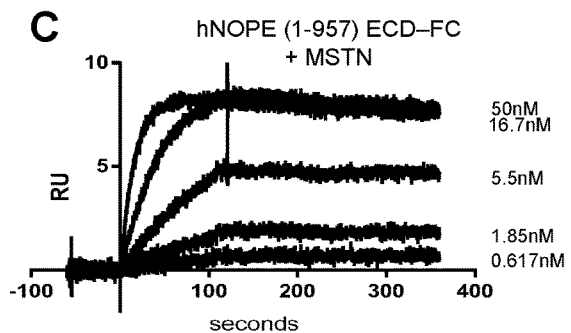
Figure 4:
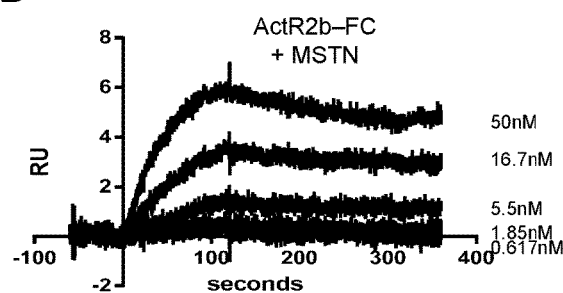

Briefly, an anti-human antibody (GE Lifesciences, NY, USA) was linked to a CM4 chip via amine coupling according to manufacturer's instructions. Both hNOPE (1-957) ECD-Fc and mNOPE (1-955) ECD-FC were captured on the chip by interaction with the anti-human antibody. A flowcell without NOPE ECD-FC served as the reference control. Myostatin and pro-myostatin were purchased from R&D Systems (MN, USA). A dose response of myostatin or pro-myostatin was injected then dissociation was monitored over time. The association constant, dissociation constant, and affinity of NOPE ECD-FC protein or Activin Receptor 2B-FC (R&D Systems, MN, USA), a positive control for myostatin binding, was calculated using the Biacore T100 Evaluation software package using the Langmuir 1:1 binding model. The affinity for human NOPE (1-957) ECD-FC and mouse NOPE (1-955) ECD-FC for MSTN are 0.2 nM and 0.8 nM, respectively while the affinity for the positive control, ActR2b-FC is 2.5 nM. NOPE ECD-FC and ActR2b-FC do not bind to pro-MSTN. As shown in FIG. 4, the NOPE proteins have similar affinities for myostatin and do not bind pro-myostatin.

Example 4

Structure-Function Studies Identify the Functional Domains of NOPE

Figure 5:
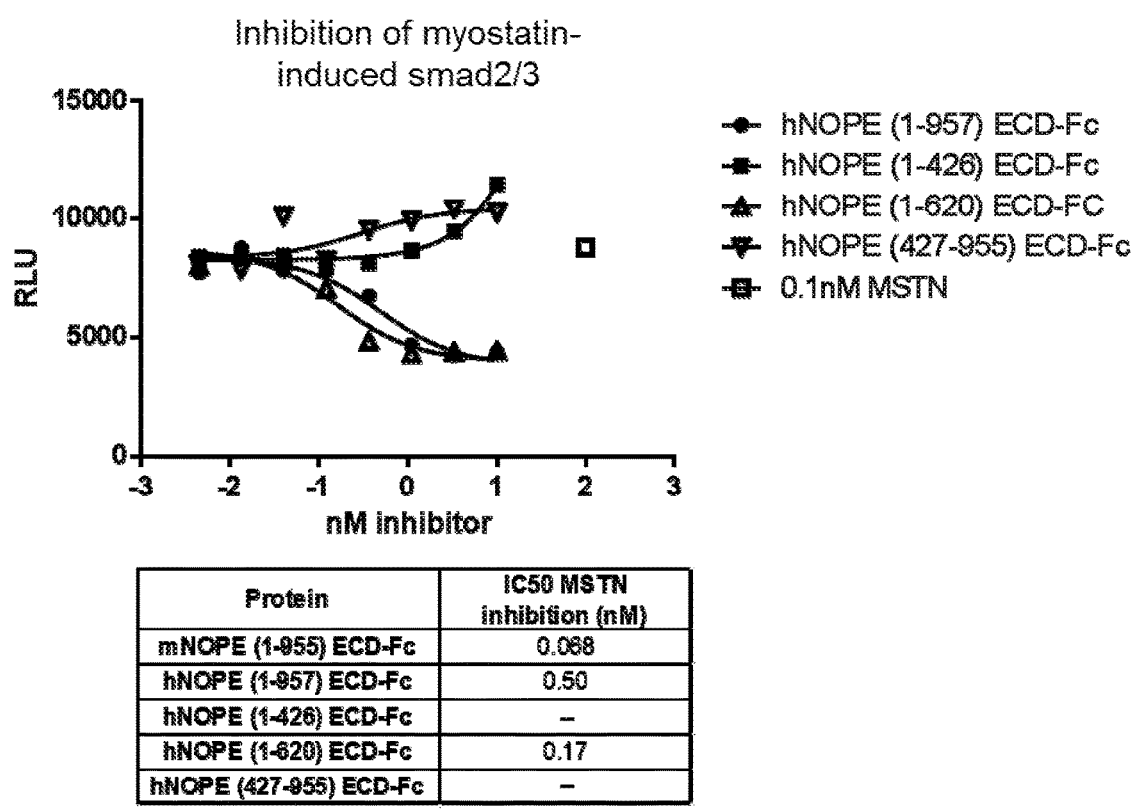
FIG. 5 shows inhibition of mysotatin by NOPE ECD-FC constructs, as described in Example 4.

To understand the functional implication of the interaction between NOPE and myostatin we employed a cell-based reporter assay to test the ability of NOPE to inhibit myostatin signaling. In addition, we created truncation mutants to determine the important functional domains of NOPE as described in Example 1. Cignal Lenti Smad 2/3 Luciferase (Qiagen) was transformed into HEK293 cells and used to test the ability of the NOPE proteins to inhibit myostatin dependent SMAD2/3 activation. A myostatin dose response curve was generated to determine the EC80 of SMAD2/3 activity. 0.1 nM of myostatin, EC80, was challenged with a dose response of mNOPE (1-955) ECD-FC, hNOPE (1-957) ECD-FC, hNOPE (1-427) ECD-FC, hNOPE (1-620) ECD-FC, and hNOPE (427-955) ECD-FC. As demonstrated in FIG. 5, the interaction with NOPE results in neutralization of myostatin activity. IC50 of hNOPE (1-957) ECD-FC & hNOPE (1-620) ECD-FC inhibition of myostatin are 0.5 and 0.17 nM, respectively. mNOPE (1-955) ECD-FC has an IC50 of 0.068 nM that is 7-fold greater than hNOPE (1-957) ECD-FC and 2.5-fold greater than hNOPE (1-620) ECD-FC. hNOPE (1-427) ECD-FC and hNOPE (427-955) ECD-FC did not inhibit myostatin induced Smad 2/3 activation (FIG. 5).

Figure 6:
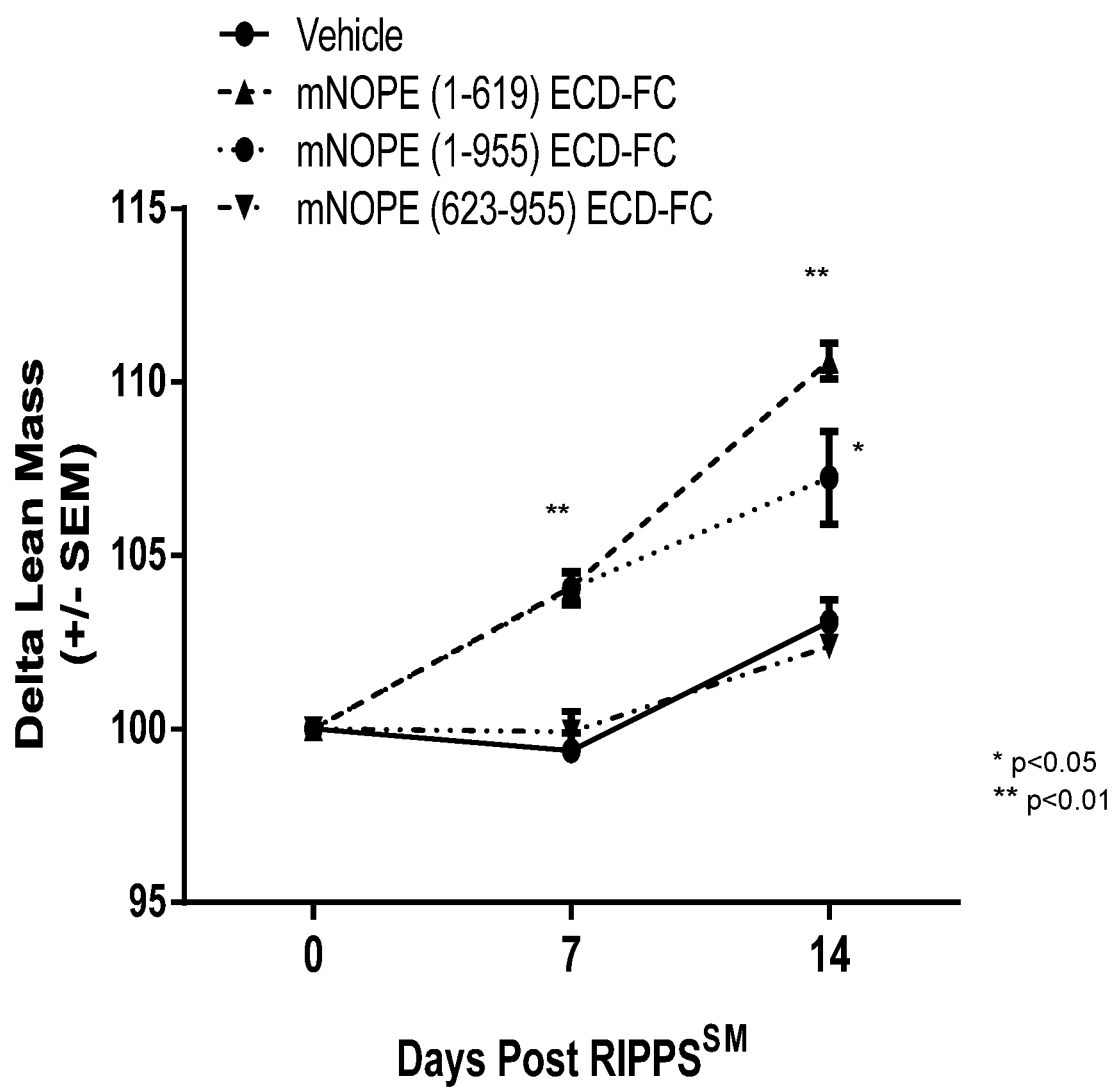
FIG. 6 shows the change in lean mass in mice administered certain NOPE ECD-FC constructs by hydrodynamic tail vein transfection, as described in Example 4.

Experiments were carried out to determine whether hydrodynamic tail vein injection the NOPE proteins has an impact on muscle growth in vivo. Female BalbC mice (Charles River Labs, Wilmington, Mass.) were randomly assigned into 4 treatment groups of 10 mice each (FIG. 6). On day 0, mice were subject to lean mass analysis as described in example 2 to establish baseline measurements. Once baseline measurements were recorded, mice were hydrodynamically transfected with mNOPE (1-955) ECD-FC, mNOPE (1-619) ECD-FC or mNOPE (623-955) ECD-FC or Vehicle control. On day 7 and 14 lean mass was measured. mNOPE (1-955) ECD-FC as well as mNOPE (1-619) ECD-FC exposure demonstrated anabolic effects in lean mass within 7 days exposure. The increase in lean mass persisted throughout the course of the study. After 14 days, lean mass organs were harvested and weighed to confirm that the increase in lean mass was muscle specific. Lean mass anabolism translates to a significant increase in skeletal muscle in animals exposed to mNOPE (1-955) ECD-FC and mNOPE (1-619) ECD-FC while liver was not affected. mNOPE (623-955) ECD-FC had no effect on lean mass or muscle weight.

TABLE OF SEQUENCES

| SEQ ID NO | Description | Sequence | | | |
|---|---|---|---|---|---|
| 1 | Human NOPE precursor (1-1250), with signal peptide | MARGDAGRGR | GLLALTFCLL | AARGELLLPQ | ETTVELSCGV |
| | | GPLQVILGPE | QAAVLNCSLG | AAAAGPPTRV | TWSKDGDTLL |
| | | EHDHLHLLPN | GSLWLSQPLA | PNGSDESVPE | AVGVIEGNYS |
| | | CLAHGPLGVL | ASQTAVVKLA | TLADFSLHPE | SQTVEENGTA |
| | | RFECHIEGLP | APIITWEKDQ | VTLPEEPRLI | VLPNGVLQIL |
| | | DVQESDAGPY | RCVATNSARQ | HFSQEALLSV | AHRGSLASTR |
| | | GQDVVIVAAP | ENTTVVSGQS | VVMECVASAD | PTPFVSWVRQ |
| | | DGKPISTDVI | VLGRTNLLIA | NAQPWHSGVY | VCRANKPRTR |

TABLE OF SEQUENCES-continued

| SEQ ID NO | Description | Sequence |
|---|---|---|
| | | DFATAAAELR VLAAPAITQA PEALSRTRAS TARFVCRASG EPRPALRWLH NGAPLRPNGR VKVQGGGGSL VITQIGLQDA GYYQCVAENS AGMACAAASL AVVVREGLPS APTRVTATPL SSSAVLVAWE RPEMHSEQII GFSLHYQKAR GMDNVEYQFA VNNDTTELQV RDLEPNTDYE FYVVAYSQLG ASRTSTPALV HTLDDVPSAA PQLSLSSPNP SDIRVAWLPL PPSLSNGQVV KYKIEYGLGK EDQIFSTEVR GNETQLMLNS LQPNKVYRVR ISAGTAAGFG APSQWMHHRT PSMHNQSHVP FAPAELKVQA KMESLVVSWQ PPPHPTQISG YKLYWREVGA EEEANGDRLP GGRGDQAWDV GPVRLKKKVK QYELTQLVPG RLYEVKLVAF NKHEDGYAAV WKGKTEKAPA PDMPIQRGPP LPPAHVHAES NSSTSIWLRW KKPDFTTVKI VNYTVRFSPW GLRNASLVTY YTSSGEDILI GGLKPFTKYE FAVQSHGVDM DGPFGSVVER STLPDRPSTP PSDLRLSPLT PSTVRLHWCP PTEPNGEIVE YLILYSSNHT QPEHQWTLLT TQGNIFSAEV HGLESDTRYF FKMGARTEVG PGPFSRLQDV ITLQEKLSDS LDMHSVTGII VGVCLGLLCL LACMCAGLRR SPHRESLPGL SSTATPGNPA LYSRARLGPP SPPAAHELES LVHPHPQDWS PPPSDVEDRA EVHSLMGGGV SEGRSHSKRK ISWAQPSGLS WAGSWAGCEL PQAGPRPALT RALLPPAGTG QTLLLQALVY DAIKGNGRKK SPPACRNQVE AEVIVHSDFS ASNGNPDLHL QDLEPEDPLP PEAPDLISGV GDPGQGAAWL DRELGGCELA APGPDRLTCL PEAASASCSY PDLQPGEVLE ETPGDSCQLK SPCPLGASPG LPRSPVSSSA |
| 2 | Human mature NOPE (25-1250), without signal peptide | ELLLPQ ETTVELSCGV GPLQVILGPE QAAVLNCSLG AAAAGPPTRV TWSKDGDTLL EHDHLHLLPN GSLWLSQPLA PNGSDESVPE AVGVIEGNYS CLAHGPLGVL ASQTAVVKLA TLADFSLHPE SQTVEENGTA RFECHIEGLP APIITWEKDQ VTLPEEPRLI VLPNGVLQIL DVQESDAGPY RCVATNSARQ HFSQEALLSV AHRGSLASTR GQDVVIVAAP ENTTVVSGQS VVMECVASAD PTPFVSWVRQ DGKPISTDVI VLGRTNLLIA NAQPWHSGVY VCRANKPRTR DFATAAAELR VLAAPAITQA PEALSRTRAS TARFVCRASG EPRPALRWLH NGAPLRPNGR VKVQGGGGSL VITQIGLQDA GYYQCVAENS AGMACAAASL AVVVREGLPS APTRVTATPL SSSAVLVAWE RPEMHSEQII GFSLHYQKAR GMDNVEYQFA VNNDTTELQV RDLEPNTDYE FYVVAYSQLG ASRTSTPALV HTLDDVPSAA PQLSLSSPNP SDIRVAWLPL PPSLSNGQVV KYKIEYGLGK EDQIFSTEVR GNETQLMLNS LQPNKVYRVR ISAGTAAGFG APSQWMHHRT PSMHNQSHVP FAPAELKVQA KMESLVVSWQ PPPHPTQISG YKLYWREVGA EEEANGDRLP GGRGDQAWDV GPVRLKKKVK QYELTQLVPG RLYEVKLVAF NKHEDGYAAV WKGKTEKAPA PDMPIQRGPP LPPAHVHAES NSSTSIWLRW KKPDFTTVKI VNYTVRFSPW GLRNASLVTY YTSSGEDILI GGLKPFTKYE FAVQSHGVDM DGPFGSVVER STLPDRPSTP PSDLRLSPLT PSTVRLHWCP PTEPNGEIVE YLILYSSNHT QPEHQWTLLT TQGNIFSAEV HGLESDTRYF FKMGARTEVG PGPFSRLQDV ITLQEKLSDS LDMHSVTGII VGVCLGLLCL LACMCAGLRR SPHRESLPGL SSTATPGNPA LYSRARLGPP SPPAAHELES LVHPHPQDWS PPPSDVEDRA EVHSLMGGGV SEGRSHSKRK ISWAQPSGLS WAGSWAGCEL PQAGPRPALT RALLPPAGTG QTLLLQALVY DAIKGNGRKK SPPACRNQVE AEVIVHSDFS ASNGNPDLHL QDLEPEDPLP PEAPDLISGV GDPGQGAAWL DRELGGCELA APGPDRLTCL PEAASASCSY PDLQPGEVLE ETPGDSCQLK SPCPLGASPG LPRSPVSSSA |
| 3 | Mouse NOPE precursor (1-1252), with signal peptide | MARADTGRGL LVLTFCLLSA RGELPLPQET TVKLSCDEGP LQVILGPEQA VVLDCTLGAT AAGPPTRVTW SKDGDTVLEH ENLHLLPNGS LWLSSPLEQE DSDDEEALRI WKVTEGSYSC LAHSPLGVVA SQVAVVKLAT LEDFSLHPES QIVEENGTAR FECHTKGLPA PIITWEKDQV TVPEESRLIT LPNGVLQILD VQDSDAGSYR CVATNSARQR FSQEASLTVA LRGSLEATRG QDVVIVAAPE NTTVVSGQSV VMECVASADP TPFVSWVRQD GKPISTDVIV LGRTNLLIAS AQPRHSGVYV CRANKPRTRD FATAAAELRV LAAPAISQAP EALSRTRAST ARFVCRASGE PRPALHWLED GIPLRPNGRV KVQGGGGSLV ITQIGLQDAG YYQCVAENSA GTACAAAPLA VVVREGLPSA PTRVTATPLS SSSVLVAWER PELHSEQIIG FSLHYQKARG VDNVEYQFAV NNDTTELQVR DLEPNTDYEF YVVAYSQLGA SRTSSPALVH TLDDVPSAAP QLTLSSPNPS DIRVAWLPLP SSLSNGQVLK YKIEYGLGKE DQVFSTEVPG NETQLTLNSL QPNKVYRVRI SAGTGAGYGV PSQWMQHRTP GVHNQSHVPF APAELKVRAK MESLVVSWQP PPHPTQISGY KLYWREVGTE EEADGDRPPG GRGDQAWDVG PVRLKKKVKQ YELTQLVPGR LYEVKLVAFN KHEDGYAAVV KGKTEKAPTP DLPIQRGPPL PPAHVHAESN SSTSIWLRWK KPDFTTVKIV NYTVRFGPWG LRNASLVTYY TSSGEDILIG GLKPFTKYEF AVQSHGVDMD GPFGSVVERS |

TABLE OF SEQUENCES-continued

| SEQ ID NO | Description | Sequence |
|---|---|---|
| | | TLPDRPSTPP SDLRLSPLTP STVRLHWCPP TEPNGEIVEY LILYSNNHTQ PEHQWTLLTT EGNIFSAEVH GLESDTRYFF HMGARTEVGP GPFSRLQDVI TLQKTFSDSL DVHAVTGIIV GVCLGLLCLL ACMCAGLRRS SHREALPGLS SSGTPGNPAL YTRARLGPPS VPAAHELESL VHPRPQDWSP PPSDVEDKAE VHSLMGGSVS DCRGESKRKI SWAQAGGPNW AGSWAGCELP QGSGPRPALT RALLPPAGTG QTLLLQALVY DAIKSNGRKK PSPACRNQVE AEVIVESDFG ASKGCPDLHL QDLEPEEPLT AETLPSTSGA VDLSQGADWL GRELGGCQPT TSGPERLTCL PEAASASCSC SDLQPSTAIE EAPGKSCQPK ALCPLTVSPS LPRAPVSSAQ VP |
| 4 | Mouse mature NOPE (23-1252), without signal peptide | ELPLPQET TVKLSCDEGP LQVILGPEQA VVLDCTLGAT AAGPPTRVTW SKDGDTVLEH ENLHLLPNGS LWLSSPLEQE DSDDEEALRI WKVTEGSYSC LAHSPLGVVA SQVAVVKLAT LEDFSLHPES QIVEENGTAR FECHTKGLPA PIITWEKDQV TVPEESRLIT LPNGVLQILD VQDSDAGSYR CVATNSARQR FSQEASLTVA LRGSLEATRG QDVVIVAAPE NTTVVSGQSV VMECVASADP TPFVSWVRQD GKPISTDVIV LGRTNLLIAS AQPRHSGVYV CRANKPRTRD FATAAAELRV LAAPAISQAP EALSRTRAST ARFVCRASGE PRPALHWLED GIPLRPNGRV KVQGGGGSLV ITQIGLQDAG YYQCVAENSA GTACAAAPLA VVVREGLPSA PTRVTATPLS SSSVLVAWER PELHSEQIIG FSLHYQKARG VDNVEYQFAV NNDTTELQVR DLEPNTDYEF YVVAYSQLGA SRTSSPALVH TLDDVPSAAP QLTLSSPNPS DIRVAWLPLP SSLSNGQVLK YKIEYGLGKE DQVFSTEVPG NETQLTLNSL QPNKVYRVRI SAGTGAGYGV PSQWMQHRTP GVHNQSHVPF APAELKVRAK MESLVVSWQP PPHPTQISGY KLYWREVGTE EEADGDRPPG GRGDQAWDVG PVRLKKKVKQ YELTQLVPGR LYEVKLVAFN KHEDGYAAVW KGKTEKAPTP DLPIQRGPPL PPAHVHAESN SSTSIWLRWK KPDFTTVKIV NYTVRFGPWG LRNASLVTYY TSSGEDILIG GLKPFTKYEF AVQSHGVDMD GPFGSVVERS TLPDRPSTPP SDLRLSPLTP STVRLHWCPP TEPNGEIVEY LILYSNNHTQ PEHQWTLLTT EGNIFSAEVH GLESDTRYFF HMGARTEVGP GPFSRLQDVI TLQKTFSDSL DVHAVTGIIV GVCLGLLCLL ACMCAGLRRS SHREALPGLS SSGTPGNPAL YTRARLGPPS VPAAHELESL VHPRPQDWSP PPSDVEDKAE VHSLMGGSVS DCRGHSKRKI SWAQAGGPNW AGSWAGCELP QGSGPRPALT RALLPPAGTG QTLLLQALVY DAIKSNGRKK PSPACRNQVE AEVIVHSDFG ASKGCPDLHL QDLEPEEPLT AETLPSTSGA VDLSQGADWL GRELGGCQPT TSGPERLTCL PEAASASCSC SDLQPSTAIE EAPGKSCQPK ALCPLTVSPS LPRAPVSSAQ VP |
| 5 | Human NOPE extracellular domain (ECD) (1-957), with signal peptide | MARGDAGRGR GLLALTFCLL AARGELLLPQ ETTVELSCGV GPLQVILGPE QAAVLNCSLG AAAAGPPTRV TWSKDGDTLL EHDHLHLLPN GSLWLSQPLA PNGSDESVPE AVGVIEGNYS CLAHGPLGVL ASQTAVVKLA TLADFSLHPE SQTVEENGTA RFECHIEGLP APIITWEKDQ VTLPEEPRLI VLPNGVLQIL DVQESDAGPY RCVATNSARQ HFSQEALLSV AHRGSLASTR GQDVVIVAAP ENTTVVSGQS VVMECVASAD PTPFVSWVRQ DGKPISTDVI VLGRTNLLIA NAQPWHSGVY VCRANKPRTR DFATAAAELR VLAAPAITQA PEALSRTRAS TARFVCRASG EPRPALRWLH NGAPLRPNGR VKVQGGGGSL VITQIGLQDA GYYQCVAENS AGMACAAASL AVVVREGLPS APTRVTATPL SSSAVLVAWE RPEMHSEQII GFSLHYQKAR GMDNVEYQFA VNNDTTELQV RDLEPNTDYE FYVVAYSQLG ASRTSTPALV HTLDDVPSAA PQLSLSSPNP SDIRVAWLPL PPSLSNGQVV KYKIEYGLGK EDQIFSTEVR GNETQLMLNS LQPNKVYRVR ISAGTAAGFG APSQWMHHRT PSMHNQSHVP FAPAELKVQA KMESLVVSWQ PPPHPTQISG YKLYWREVGA EEEANGDRLP GGRGDQAWDV GPVRLKKKVK QYELTQLVPG RLYEVKLVAF NKHEDGYAAV WKGKTEKAPA PDMPIQRGPP LPPAHVHAES NSSTSIWLRW KKPDFTTVKI VNYTVRFSPW GLRNASLVTY YTSSGEDILI GGLKPFTKYE FAVQSHGVDM DGPFGSVVER STLPDRPSTP PSDLRLSPLT PSTVRLHWCP PTEPNGEIVE YLILYSSNHT QPEHQWTLLT TQGNIFSAEV HGLESDTRYF FKMGARTEVG PGPFSRLQDV ITLQEKLSDS LDMHSVT |
| 6 | Human NOPE ECD (25-955), without signal peptide | ELLLPQ ETTVELSCGV GPLQVILGPE QAAVLNCSLG AAAAGPPTRV TWSKDGDTLL EHDHLHLLPN GSLWLSQPLA PNGSDESVPE AVGVIEGNYS CLAHGPLGVL ASQTAVVKLA TLADFSLHPE SQTVEENGTA RFECHIEGLP APIITWEKDQ VTLPEEPRLI VLPNGVLQIL DVQESDAGPY RCVATNSARQ HFSQEALLSV AHRGSLASTR GQDVVIVAAP ENTTVVSGQS VVMECVASAD PTPFVSWVRQ DGKPISTDVI VLGRTNLLIA NAQPWHSGVY VCRANKPRTR DFATAAAELR VLAAPAITQA PEALSRTRAS TARFVCRASG EPRPALRWLH NGAPLRPNGR |

TABLE OF SEQUENCES-continued

| SEQ ID NO | Description | Sequence |
|---|---|---|
| | | VKVQGGGGSL VITQIGLQDA GYYQCVAENS AGMACAAASL AVVVREGLPS APTRVTATPL SSSAVLVAWE RPEMHSEQII GFSLHYQKAR GMDNVEYQFA VNNDTTELQV RDLEPNTDYE FYVVAYSQLG ASRTSTPALV HTLDDVPSAA PQLSLSSPNP SDIRVAWLPL PPSLSNGQVV KYKIEYGLGK EDQIFSTEVR GNETQLMLNS LQPNKVYRVR ISAGTAAGFG APSQWMHHRT PSMHNQSHVP FAPAELKVQA KMESLVVSWQ PPPHPTQISG YKLYWREVGA EEEANGDRLP GGRGDQAWDV GPVRLKKKVK QYELTQLVPG RLYEVKLVAF NKHEDGYAAV WKGKTEKAPA PDMPIQRGPP LPPAHVEAES NSSTSIWLRW KKPDFTTVKI VNYTVRFSPW GLRNASLVTY YTSSGEDILI GGLKPFTKYE FAVQSHGVDM DGPFGSVVER STLPDRPSTP PSDLRLSPLT PSTVRLHWCP PTEPNGEIVE YLILYSSNHT QPEHQWTLLT TQGNIFSAEV HGLESDTRYF FKMGARTEVG PGPFSRLQDV ITLQEKLSDS LDMHS |
| 7 | Human NOPE ECD (25-426), without signal peptide | ELLLPQ ETTVELSCGV GPLQVILGPE QAAVLNCSLG AAAAGPPTRV TWSKDGDTLL EHDHLHLLPN GSLWLSQPLA PNGSDESVPE AVGVIEGNYS CLAHGPLGVL ASQTAVVKLA TLADFSLHPE SQTVEENGTA RFECHIEGLP APIITWEKDQ VTLPEEPRLI VLPNGVLQIL DVQESDAGPY RCVATNSARQ HFSQEALLSV AHRGSLASTR GQDVVIVAAP ENTTVVSGQS VVMECVASAD PTPFVSWVRQ DGKPISTDVI VLGRTNLLIA NAQPWHSGVY VCRANKPRTR DFATAAAELR VLAAPAITQA PEALSRTRAS TARFVCRASG EPRPALRWLH NGAPLRPNGR VKVQGGGGSL VITQIGLQDA GYYQCVAENS AGMACAAASL AVVVRE |
| 8 | Human NOPE ECD (25-620), without signal peptide | ELLLPQ ETTVELSCGV GPLQVILGPE QAAVLNCSLG AAAAGPPTRV TWSKDGDTLL EHDHLHLLPN GSLWLSQPLA PNGSDESVPE AVGVIEGNYS CLAHGPLGVL ASQTAVVKLA TLADFSLHPE SQTVEENGTA RFECHIEGLP APIITWEKDQ VTLPEEPRLI VLPNGVLQIL DVQESDAGPY RCVATNSARQ HFSQEALLSV AHRGSLASTR GQDVVIVAAP ENTTVVSGQS VVMECVASAD PTPFVSWVRQ DGKPISTDVI VLGRTNLLIA NAQPWHSGVY VCRANKPRTR DFATAAAELR VLAAPAITQA PEALSRTRAS TARFVCRASG EPRPALRWLE NGAPLRPNGR VKVQGGGGSL VITQIGLQDA GYYQCVAENS AGMACAAASL AVVVREGLPS APTRVTATPL SSSAVLVAWE RPEMHSEQII GFSLHYQKAR GMDNVEYQFA VNNDTTELQV RDLEPNTDYE FYVVAYSQLG ASRTSTPALV HTLDDVPSAA PQLSLSSPNP SDIRVAWLPL PPSLSNGQVV KYKIEYGLGK EDQIFSTEVR GNETQLMLNS LQPNKVYRVR ISAGTAAGFG APSQWMHHRT |
| 9 | Human NOPE ECD (427-955) | GLPS APTRVTATPL SSSAVLVAWE RPEMHSEQII GFSLHYQKAR GMDNVEYQFA VNNDTTELQV RDLEPNTDYE FYVVAYSQLG ASRTSTPALV HTLDDVPSAA PQLSLSSPNP SDIRVAWLPL PPSLSNGQVV KYKIEYGLGK EDQIFSTEVR GNETQLMLNS LQPNKVYRVR ISAGTAAGFG APSQWMHHRT PSMHNQSHVP FAPAELKVQA KMESLVVSWQ PPPHPTQISG YKLYWREVGA EEEANGDRLP GGRGDQAWDV GPVRLKKKVK QYELTQLVPG RLYEVKLVAF NKHEDGYAAV WKGKTEKAPA PDMPIQRGPP LPPAHVEAES NSSTSIWLRW KKPDFTTVKI VNYTVRFSPW GLRNASLVTY YTSSGEDILI GGLKPFTKYE FAVQSHGVDM DGPFGSVVER STLPDRPSTP PSDLRLSPLT PSTVRLHWCP PTEPNGEIVE YLILYSSNHT QPEHQWTLLT TQGNIFSAEV HGLESDTRYF FKMGARTEVG PGPFSRLQDV ITLQEKLSDS LDMHS |
| 10 | Human NOPE ECD (623-955) | MHNQSHVP FAPAELKVQA KMESLVVSWQ PPPHPTQISG YKLYWREVGA EEEANGDRLP GGRGDQAWDV GPVRLKKKVK QYELTQLVPG RLYEVKLVAF NKHEDGYAAV WKGKTEKAPA PDMPIQRGPP LPPAHVHAES NSSTSIWLRW KKPDFTTVKI VNYTVRFSPW GLRNASLVTY YTSSGEDILI GGLKPFTKYE FAVQSHGVDM DGPFGSVVER STLPDRPSTP PSDLRLSPLT PSTVRLHWCP PTEPNGEIVE YLILYSSNHT QPEHQWTLLT TQGNIFSAEV HGLESDTRYF FKMGARTEVG PGPFSRLQDV ITLQEKLSDS LDMHS |
| 11 | Mouse NOPE extracellular domain (ECD) (1-956), with signal peptide | MARADTGRGL LVLTFCLLSA RGELPLPQET TVKLSCDEGP LQVILGPEQA VVLDCTLGAT AAGPPTRVTW SKDGDTVLEH ENLHLLPNGS LWLSSPLEQE DSDDEEALRI WKVTEGSYSC LAHSPLGVVA SQVAVVKLAT LEDFSLHPES QIVEENGTAR FECHTKGLPA PIITWEKDQV TVPEESRLIT LPNGVLQILD VQDSDAGSYR CVATNSARQR FSQEASLTVA LRGSLEATRG QDVVIVAAPE NTTVVSGQSV VMECVASADP TPFVSWVRQD GKPISTDVIV LGRTNLLIAS AQPRHSGVYV CRANKPRTRD FATAAAELRV LAAPAISQAP EALSRTRAST ARFVCRASGE |

TABLE OF SEQUENCES-continued

| SEQ ID NO | Description | Sequence |
|---|---|---|
| | | PRPALHWLHD GIPLRPNGRV KVQGGGGSLV ITQIGLQDAG YYQCVAENSA GTACAAAPLA VVVREGLPSA PTRVTATPLS SSSVLVAWER PELHSEQIIG FSLHYQKARG VDNVEYQFAV NNDTTELQVR DLEPNTDYEF YVVAYSQLGA SRTSSPALVH TLDDVPSAAP QLTLSSPNPS DIRVAWLPLP SSLSNGQVLK YKIEYGLGKE DQVFSTEVPG NETQLTLNSL QPNKVYRVRI SAGTGAGYGV PSQWMQHRTP GVHNQSHVPF APAELKVRAK MESLVVSWQP PPEPTQISGY KLYWREVGTE EEADGDRPPG GRGDQAWDVG PVRLKKKVKQ YELTQLVPGR LYEVKLVAFN KHEDGYAAVW KGKTEKAPTP DLPIQRGPPL PPAHVHAESN SSTSIWLRWK KPDFTTVKIV NYTVRFGPWG LRNASLVTYY TSSGEDILIG GLKPFTKYEF AVQSHGVDMD GPFGSVVERS TLPDRPSTPP SDLRLSPLTP STVRLHWCPP TEPNGEIVEY LILYSNNHTQ PEHQWTLLTT EGNIFSAEVH GLESDTRYFF KMGARTEVGP GPFSRLQDVI TLQKTFSDSL DVHAVT |
| 12 | Mouse NOPE ECD (23-956), without signal peptide | ELPLPQET TVKLSCDEGP LQVILGPEQA VVLDCTLGAT AAGPPTRVTW SKDGDTVLEH ENLHLLPNGS LWLSSPLEQE DSDDEEALRI WKVTEGSYSC LAHSPLGVVA SQVAVVKLAT LEDFSLHPES QIVEENGTAR FECHTKGLPA PIITWEKDQV TVPEESRLIT LPNGVLQILD VQDSDAGSYR CVATNSARQR FSQEASLTVA LRGSLEATRG QDVIVAAPE NTTVVSGQSV VMECVASADP TPFVSWVRQD GKPISTDVIV LGRTNLLIAS AQPRHSGVYV CRANKPRTRD FATAAAELRV LAAPAISQAP EALSRTRAST ARFVCRASGE PRPALHWLHD GIPLRPNGRV KVQGGGGSLV ITQIGLQDAG YYQCVAENSA GTACAAAPLA VVVREGLPSA PTRVTATPLS SSSVLVAWER PELHSEQIIG FSLHYQKARG VDNVEYQFAV NNDTTELQVR DLEPNTDYEF YVVAYSQLGA SRTSSPALVH TLDDVPSAAP QLTLSSPNPS DIRVAWLPLP SSLSNGQVLK YKIEYGLGKE DQVFSTEVPG NETQLTLNSL QPNKVYRVRI SAGTGAGYGV PSQWMQHRTP GVHNQSHVPF APAELKVRAK MESLVVSWQP PPHPTQISGY KLYWREVGTE EEADGDRPPG GRGDQAWDVG PVRLKKKVKQ YELTQLVPGR LYEVKLVAFN KHEDGYAAVW KGKTEKAPTP DLPIQRGPPL PPAHVHAESN SSTSIWLRWK KPDFTTVKIV NYTVRFGPWG LRNASLVTYY TSSGEDILIG GLKPFTKYEF AVQSHGVDMD GPFGSVVERS TLPDRPSTPP SDLRLSPLTP STVRLHWCPP TEPNGEIVEY LILYSNNHTQ PEHQWTLLTT EGNIFSAEVH GLESDTRYFF KMGARTEVGP GPFSRLQDVI TLQKTFSDSL DVHAVT |
| 13 | Mouse NOPE ECD (23-619), without signal peptide | ELPLPQET TVKLSCDEGP LQVILGPEQA VVLDCTLGAT AAGPPTRVTW SKDGDTVLEH ENLHLLPNGS LWLSSPLEQE DSDDEEALRI WKVTEGSYSC LAHSPLGVVA SQVAVVKLAT LEDFSLHPES QIVEENGTAR FECHTKGLPA PIITWEKDQV TVPEESRLIT LPNGVLQILD VQDSDAGSYR CVATNSARQR FSQEASLTVA LRGSLEATRG QDVIVAAPE NTTVVSGQSV VMECVASADP TPFVSWVRQD GKPISTDVIV LGRTNLLIAS AQPRHSGVYV CRANKPRTRD FATAAAELRV LAAPAISQAP EALSRTRAST ARFVCRASGE PRPALHWLHD GIPLRPNGRV KVQGGGGSLV ITQIGLQDAG YYQCVAENSA GTACAAAPLA VVVREGLPSA PTRVTATPLS SSSVLVAWER PELESEQIIG FSLHYQKARG VDNVEYQFAV NNDTTELQVR DLEPNTDYEF YVVAYSQLGA SRTSSPALVH TLDDVPSAAP QLTLSSPNPS DIRVAWLPLP SSLSNGQVLK YKIEYGLGKE DQVFSTEVPG NETQLTLNSL QPNKVYRVRI SAGTGAGYGV PSQWMQHRT |
| 14 | Mouse NOPE ECD (623-956), without signal peptide | HNQSHVPF APAELKVRAK MESLVVSWQP PPEPTQISGY KLYWREVGTE EEADGDRPPG GRGDQAWDVG PVRLKKKVKQ YELTQLVPGR LYEVKLVAFN KHEDGYAAVW KGKTEKAPTP DLPIQRGPPL PPAHVHAESN SSTSIWLRWK KPDFTTVKIV NYTVRFGPWG LRNASLVTYY TSSGEDILIG GLKPFTKYEF AVQSHGVDMD GPFGSVVERS TLPDRPSTPP SDLRLSPLTP STVRLHWCPP TEPNGEIVEY LILYSNNHTQ PEHQWTLLTT EGNIFSAEVH GLESDTRYFF KMGARTEVGP GPFSRLQDVI TLQKTFSDSL DVHAVT |
| 15 | Human NOPE ECD (25-955)-Fc fusion molecule, without signal peptide | ELLLPQETTV ELSCGVGPLQ VILGPEQAAV LNCSLGAAAA GPPTRVTWSK DGDTLLEHDH LHLLPNGSLW LSQPLAPNGS DESVPEAVGV IEGNYSCLAH GPLGVLASQT AVVKLATLAD FSLHPESQTV EENGTARFEC HIEGLPAPII TWEKDQVTLP EEPRLIVLPN GVLQILDVQE SDAGPYRCVA TNSARQHFSQ EALLSVAHRG SLASTRGQDV VIVAAPENTT VVSGQSVVME CVASADPTPF VSWVRQDGKP ISTDVIVLGR TNLLIANAQP WHSGVYVCRA NKPRTRDFAT AAAELRVLAA PAITQAPEAL SRTRASTARF VCRASGEPRP ALRWLHNGAP LRPNGRVKVQ GGGGSLVITQ IGLQDAGYYQ CVAENSAGMA CAAASLAVVV REGLPSAPTR VTATPLSSSA VLVAWERPEM HSEQIIGFSL |

TABLE OF SEQUENCES-continued

| SEQ ID NO | Description | Sequence |
|---|---|---|
| | | HYQKARGMDN VEYQFAVNND TTELQVRDLE PNTDYEFYVV
AYSQLGASRT STPALVHTLD DVPSAAPQLS LSSPNPSDIR
VAWLPLPPSL SNGQVVKYKI EYGLGKEDQI FSTEVRGNET
QLMLNSLQPN KVYRVRISAG TAAGFGAPSQ WMHHRTPSMH
NQSHVPFAPA ELKVQAKMES LVVSWQPPPH PTQISGYKLY
WREVGAEEEA NGDRLPGGRG DQAWDVGPVR LKKKVKQYEL
TQLVPGRLYE VKLVAFNKHE DGYAAVWKGK TEKAPAPDMP
IQRGPPLPPA HVHAESNSST SIWLRWKKPD FTTVKIVNYT
VRFSPWGLRN ASLVTYYTSS GEDILIGGLK PFTKYEFAVQ
SHGVDMDGPF GSVVERSTLP DRPSTPPSDL RLSPLTPSTV
RLHWCPPTEP NGEIVEYLIL YSSNHTQPEH QWTLLTTQGN
IFSAEVHGLE SDTRYFFKMG ARTEVGPGPF SRLQDVITLQ
EKLSDSLDMH SGSEPKSSDK THTCPPCPAP ELLGGPSVFL
FPPKPKDTLM ISRTPEVTCV VVDVSHEDPE VKFNWYVDGV
EVHNAKTKPR EEQYNSTYRV VSVLTVLHQD WLNGKEYKCK
VSNKALPAPI EKTISKAKGQ PREPQVYTLP PSRDELTKNQ
VSLTCLVKGF YPSDIAVEWE SNGQPENNYK TTPPVLDSDG
SFFLYSKLTV DKSRWQQGNV FSCSVMHEAL HNHYTQKSLS
LSPGK |
| 16 | Human NOPE ECD (25-426)-Fc fusion molecule, without signal peptide | ELLLPQ ETTVELSCGV GPLQVILGPE QAAVLNCSLG
AAAAGPPTRV TWSKDGDTLL EHDHLHLLPN GSLWLSQPLA
PNGSDESVPE AVGVIEGNYS CLAHGPLGVL ASQTAVVKLA
TLADFSLEPE SQTVEENGTA RFECHIEGLP APIITWEKDQ
VTLPEEPRLI VLPNGVLQIL DVQESDAGPY RCVATNSARQ
HFSQEALLSV AHRGSLASTR GQDVVIVAAP ENTTVVSGQS
VVMECVASAD PTPFVSWVRQ DGKPISTDVI VLGRTNLLIA
NAQPWHSGVY VCRANKPRTR DFATAAAELR VLAAPAITQA
PEALSRTRAS TARFVCRASG EPRPALRWLH NGAPLRPNGR
VKVQGGGGSL VITQIGLQDA GYYQCVAENS AGMACAAASL
AVVVREGSEPKSSDK THTCPPCPAP ELLGGPSVFL
FPPKPKDTLM ISRTPEVTCV VVDVSHEDPE VKFNWYVDGV
EVENAKTKPR EEQYNSTYRV VSVLTVLHQD WLNGKEYKCK
VSNKALPAPI EKTISKAKGQ PREPQVYTLP PSRDELTKNQ
VSLTCLVKGF YPSDIAVEWE SNGQPENNYK TTPPVLDSDG
SFFLYSKLTV DKSRWQQGNV FSCSVMHEAL HNHYTQKSLS
LSPGK |
| 17 | Human NOPE ECD (25-620)-Fc fusion molecule, without signal peptide | ELLLPQ ETTVELSCGV GPLQVILGPE QAAVLNCSLG
AAAAGPPTRV TWSKDGDTLL EHDHLHLLPN GSLWLSQPLA
PNGSDESVPE AVGVIEGNYS CLAHGPLGVL ASQTAVVKLA
TLADFSLHPE SQTVEENGTA RFECHIEGLP APIITWEKDQ
VTLPEEPRLI VLPNGVLQIL DVQESDAGPY RCVATNSARQ
HFSQEALLSV AHRGSLASTR GQDVVIVAAP ENTTVVSGQS
VVMECVASAD PTPFVSWVRQ DGKPISTDVI VLGRTNLLIA
NAQPWHSGVY VCRANKPRTR DFATAAAELR VLAAPAITQA
PEALSRTRAS TARFVCRASG EPRPALRWLH NGAPLRPNGR
VKVQGGGGSL VITQIGLQDA GYYQCVAENS AGMACAAASL
AVVVREGLPS APTRVTATPL SSSAVLVAWE RPEMHSEQII
GFSLHYQKAR GMDNVEYQFA VNNDTTELQV RDLEPNTDYE
FYVVAYSQLG ASRTSTPALV HTLDDVPSAA PQLSLSSPNP
SDIRVAWLPL PPSLSNGQVV KYKIEYGLGK EDQIFSTEVR
GNETQLMLNS LQPNKVYRVR ISAGTAAGFG
APSQWMHHRTGSEPKSSDK THTCPPCPAP ELLGGPSVFL
FPPKPKDTLM ISRTPEVTCV VVDVSHEDPE VKFNWYVDGV
EVHNAKTKPR EEQYNSTYRV VSVLTVLHQD WLNGKEYKCK
VSNKALPAPI EKTISKAKGQ PREPQVYTLP PSRDELTKNQ
VSLTCLVKGF YPSDIAVEWE SNGQPENNYK TTPPVLDSDG
SFFLYSKLTV DKSRWQQGNV FSCSVMHEAL HNHYTQKSLS
LSPGK |
| 18 | Human NOPE ECD (427-955)-Fc fusion molecule, without signal peptide | GLPS APTRVTATPL SSSAVLVAWE RPEMHSEQII
GFSLNYQKAR GMDNVEYQFA VNNDTTELQV RDLEPNTDYE
FYVVAYSQLG ASRTSTPALV HTLDDVPSAA PQLSLSSPNP
SDIRVAWLPL PPSLSNGQVV KYKIEYGLGK EDQIFSTEVR
GNETQLMLNS LQPNKVYRVR ISAGTAAGFG APSQWMHHRT
PSMHNQSNVP FAPAELKVQA KMESLVVSWQ PPPHPTQISG
YKLYWREVGA EEEANGDRLP GGRGDQAWDV GPVRLKKKVK
QYELTQLVPG RLYEVKLVAF NKHEDGYAAV WKGKTEKAPA
PDMPIQRGPP LPPAHVHAES NSSTSIWLRW KKPDFTTVKI
VNYTVRFSPW GLRNASLVTY YTSSGEDILI GGLKPFTKYE
FAVQSHGVDM DGPFGSVVER STLPDRPSTP PSDLRLSPLT
PSTVRLEWCP PTEPNGEIVE YLILYSSNHT QPEHQWTLLT
TQGNIFSAEV HGLESDTRYF FKMGARTEVG PGPFSRLQDV
ITLQEKLSDS LDMHSGSEPKSSDK THTCPPCPAP
ELLGGPSVFL FPPKPKDTLM ISRTPEVTCV VVDVSHEDPE
VKFNWYVDGV EVHNAKTKPR EEQYNSTYRV VSVLTVLHQD
WLNGKEYKCK VSNKALPAPI EKTISKAKGQ PREPQVYTLP |

TABLE OF SEQUENCES-continued

| SEQ ID NO | Description | Sequence |
|---|---|---|
| | | PSRDELTKNQ VSLTCLVKGF YPSDIAVEWE SNGQPENNYK TTPPVLDSDG SFFLYSKLTV DKSRWQQGNV FSCSVMHEAL HNHYTQKSLS LSPGK |
| 19 | Human NOPE ECD (623-955)-Fc fusion molecule, without signal peptide | MHNQSHVP FAPAELKVQA KMESLVVSWQ PPPHPTQISG YKLYWREVGA EEEANGDRLP GGRGDQAWDV GPVRLKKKVK QYELTQLVPG RLYEVKLVAF NKKEDGYAAV WKGKTEKAPA PDMPIQRGPP LPPAHVHAES NSSTSIWLRW KKPDFTTVKI VNYTVRFSPW GLRNASLVTY YTSSGEDILI GGLKPFTKYE FAVQSHGVDM DGPFGSVVER STLPDRPSTP PSDLRLSPLT PSTVRLHWCP PTEPNGEIVE YLILYSSNHT QPEHQWTLLT TQGNIFSAEV HGLESDTRYF FKMGARTEVG PGPFSRLQDV ITLQEKLSDS LDMHSGSEPKSSDK THTCPPCPAP ELLGGPSVFL FPPKPKDTLM ISRTPEVTCV VVDVSHEDPE VKFNWYVDGV EVHNAKTKPR EEQYNSTYRV VSVLTVLHQD WLNGKEYKCK VSNKALPAPI EKTISKAKGQ PREPQVYTLP PSRDELTKNQ VSLTCLVKGF YPSDIAVEWE SNGQPENNYK TTPPVLDSDG SFFLYSKLTV DKSRWQQGNV FSCSVMHEAL HNHYTQKSLS LSPGK |
| 20 | Human myostatin | DFGL DCDEHSTESR CCRYPLTVDF EAFGWDWIIA PKRYKANYCS GECEFVFLQK YPHTHLVHQA NPRGSAGPCC TPTKMSPINM LYFNGKEQII YGKIPAMVVD RCGCS |
| 21 | Human pro-myostatin (with signal sequence) | MQKLQLCVYI YLFMLIVAGP VDLNENSEQK ENVEKEGLCN ACTWRQNTKS SRIEAIKIQI LSKLRLETAP NISKDVIRQL LPKAPPLREL IDQYDVQRDD SSDGSLEDDD YHATTETIIT MPTESDFLMQ VDGKPKCCFF KFSSKIQYNK VVKAQLWIYL RPVETPTTVF VQILRLIKPM KDGTRYTGIR SLKLDMNPGT GIWQSIDVKT VLQNWLKQPE SNLGIEIKAL DENGHDLAVT FPGPGEDGLN PFLEVKVTDT PKRSRRDFGL DCDEHSTESR CCRYPLTVDF EAFGWDWIIA PKRYKANYCS GECEFVFLQK YPHTHLVHQA NPRGSAGPCC TPTKMSPINM LYFNGKEQII YGKIPAMVVD RCGCS |
| 22 | Human pro-myostatin (without signal sequence) | NENSEQK ENVEKEGLCN ACTWRQNTKS SRIEAIKIQI LSKLRLETAP NISKDVIRQL LPKAPPLREL IDQYDVQRDD SSDGSLEDDD YHATTETIIT MPTESDFLMQ VDGKPKCCFF KFSSKIQYNK VVKAQLWIYL RPVETPTTVF VQILRLIKPM KDGTRYTGIR SLKLDMNPGT GIWQSIDVKT VLQNWLKQPE SNLGIEIKAL DENGHDLAVT FPGPGEDGLN PFLEVKVTDT PKRSRRDFGL DCDEHSTESR CCRYPLTVDF EAFGWDWIIA PKRYKANYCS GECEFVFLQK YPHTHLVHQA NPRGSAGPCC TPTKMSPINM LYFNGKEQII YGKIPAMVVD RCGCS |
| 23 | Mouse myostatin | DFG LDCDEHSTES RCCRYPLTVD FEAFGWDWII APKRYKANYC SGECEFVFLQ KYPHTHLVHQ ANPRGSAGPC CTPTKMSPIN MLYFNGKEQI IYGKIPAMVV DRCGCS |
| 24 | Mouse pro-myostatin (with signal sequence) | MMQKLQMYVY IYLFMLIAAG PVDLNEGSER EENVEKEGLC NACAWRQNTR YSRIEAIKIQ ILSKLRLETA PNISKDAIRQ LLPRAPPLRE LIDQYDVQRD DSSDGSLEDD DYHATTETII TMPTESDFLM QADGKPKCCF FKFSSKIQYN KVVKAQLWIY LRPVKTPTTV FVQILRLIKP MKDGTRYTGI RSLKLDMSPG TGIWQSIDVK TVLQNWLKQP ESNLGIEIKA LDENGHDLAV TFPGPGEDGL NPFLEVKVTD TPKRSRRDFG LDCDEHSTES RCCRYPLTVD FEAFGWDWII APKRYKANYC SGECEFVFLQ KYPHTHLVHQ ANPRGSAGPC CTPTKMSPIN MLYFNGKEQI IYGKIPAMVV DRCGCS |
| 25 | Mouse pro-myostatin (without signal sequence) | EGSER EENVEKEGLC NACAWRQNTR YSRIEAIKIQ ILSKLRLETA PNISKDAIRQ LLPRAPPLRE LIDQYDVQRD DSSDGSLEDD DYHATTETII TMPTESDFLM QADGKPKCCF FKFSSKIQYN KVVKAQLWIY LRPVKTPTTV FVQILRLIKP MKDGTRYTGI RSLKLDMSPG TGIWQSIDVK TVLQNWLKQP ESNLGIEIKA LDENGHDLAV TFPGPGEDGL NPFLEVKVTD TPKRSRRDFG LDCDEHSTES RCCRYPLTVD FEAFGWDWII APKRYKANYC SGECEFVFLQ KYPHTHLVHQ ANPRGSAGPC CTPTKMSPIN MLYFNGKEQI IYGKIPAMVV DRCGCS |
| 26 | Fc C237S | EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSR DELTKNQVSL TCLVKGFYPS DIAVEWESNG QPENNYKTTP PVLDSDGSFF LYSKLTVDKS RWQQGNVFSC SVMHEALHNH YTQKSLSLSP GK |

TABLE OF SEQUENCES-continued

| SEQ ID NO | Description | Sequence |
|---|---|---|
| 27 | Exemplary Fc #1 | ERKCCVECPP CPAPPVAGPS VFLFPPKPKD TLMISRTPEV TCVVVDVSHE DPEVQFNWYV DGVEVHNAKT KPREEQFNST FRVVSVLTVV HQDWLNGKEY KCKVSNKGLP APIEKTISKT KGQPREPQVY TLPPSREEMT KNQVSLTCLV KGFYPSDIAV EWESNGQPEN NYKTTPPMLD SDGSFFLYSK LTVDKSRWQQ GNVFSCSVMH EALHNHYTQK SLSLSPGK |
| 28 | Exemplary Fc #2 | ESKYGPPCPS CPAPEFLGGP SVFLFPPKPK DTLMISRTPE VTCVVVDVSQ EDPEVQFNWY VDGVEVHNAK TKPREEQFNS TYRVVSVLTV LHQDWLNGKE YKCKVSNKGL PSSIEKTISK AKGQPREPQV YTLPPSQEEM TKNQVSLTCL VKGFYPSDIA VEWESNGQPE NNYKTTPPVL DSDGSFFLYS RLTVDKSRWQ EGNVFSCSVM HEALHNHYTQ KSLSLSLGK |

The invention claimed is:

1. A NOPE ECD fusion molecule comprising the sequence of SEQ ID NO: 17.

2. A polynucleotide encoding the NOPE ECD fusion molecule of claim 1.

3. A vector comprising the polynucleotide of claim 2.

4. A host cell comprising the vector of claim 3.

5. A method for treating a muscle degenerative disorder, wherein the muscle degenerative disorder is selected from muscular dystrophy, myotonic dystrophy, polymyositis, and dermatomyositis in a subject in need of such treatment, the method comprising administering to the subject an effective amount of a NOPE extracellular domain (ECD) polypeptide or a NOPE ECD fusion molecule, wherein the NOPE ECD or NOPE ECD fusion molecule comprises amino acids 26 to 620 of SEQ ID NO: 1.

6. The method of claim 5, wherein the muscle degenerative disorder is muscular dystrophy.

7. The method of claim 6, wherein the muscular dystrophy is selected from Duchenne muscular dystrophy, Becker muscular dystrophy, congenital muscular dystrophy, Fukuyama muscular dystrophy, Emery Dreifuss muscular dystrophy, limb girdle muscular dystrophy, and fascioscapulohumeral muscular dystrophy.

8. The method of claim 5, wherein the muscle degenerative disorder is myotonic dystrophy.

9. The method of claim 8, wherein the myotonic dystrophy is selected from myotonic dystrophy type I, myotonic dystrophy type II, and congenital myotonia.

10. The method of claim 5, wherein the method comprises administering to the subject an effective amount of the NOPE ECD fusion molecule.

11. The method of claim 5, wherein the NOPE ECD polypeptide or NOPE ECD fusion molecule is capable of binding myostatin with a $K_D$ of less than 100 nM and/or inhibiting myostatin-mediated activation of SMAD2/3.

12. The method of claim 10, wherein the NOPE ECD fusion molecule comprises a NOPE ECD polypeptide and an Fc.

13. The method of claim 12, wherein the NOPE ECD fusion molecule comprises the sequence of SEQ ID NO: 17.

14. A method of treating amyotrophic lateral sclerosis (ALS), comprising administering to a subject with ALS an effective amount of a NOPE extracellular domain (ECD) polypeptide or a NOPE ECD fusion molecule, wherein the NOPE ECD or NOPE ECD fusion molecule comprises amino acids 26 to 620 of SEQ ID NO: 1.

15. The method of claim 14, wherein the treatment delays progression of ALS by having at least one effect selected from the group consisting of: reducing physical decline, improving forced vital capacity, slowing the decline in forced vital capacity, slowing the decline in the subject's score on the ALS functional rating scale (ALSFRS), improving the subject's score on the ALSFRS, delaying occurrence of life-changing events, improving the subject's time of survival, delaying a tracheostomy and delaying placement of a percutaneous endoscopic gastrostomy (PEG).

16. The method of claim 14, wherein the method comprises administering to the subject an effective amount of the NOPE ECD fusion molecule.

17. The method of claim 14, wherein the NOPE ECD polypeptide or NOPE ECD fusion molecule is capable of binding myostatin with a KD of less than 100 nM and/or inhibiting myostatin-mediated activation of SMAD2/3.

18. The method of claim 16, wherein the NOPE ECD fusion molecule comprises a NOPE ECD polypeptide and an Fc.

19. The method of claim 18, wherein the NOPE ECD fusion molecule comprises the sequence of SEQ ID NO: 17.

20. A method for increasing type I slow muscle mass or decreasing fat mass, the method comprising administering to a subject an effective amount of a NOPE extracellular domain (ECD) fusion molecule comprising the sequence of SEQ ID NO: 17.

* * * * *

UNITED STATES PATENT AND TRADEMARK OFFICE
CERTIFICATE OF CORRECTION

PATENT NO. : 10,799,559 B2
APPLICATION NO. : 16/095974
DATED : October 13, 2020
INVENTOR(S) : Aaron Curtis Hinken et al.

Page 1 of 1

It is certified that error appears in the above-identified patent and that said Letters Patent is hereby corrected as shown below:

In the Claims

In Claim 17, Column 132, Line 26 should read --binding myostatin with a $K_D$ of less than 100nM and/or--

Signed and Sealed this
Thirtieth Day of March, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 28

<210> SEQ ID NO 1
<211> LENGTH: 1250
<212> TYPE: PRT
<213> ORGANISM: Artificial Sequence
<220> FEATURE:
<223> OTHER INFORMATION: Human NOPE precursor (1-1250), with signal peptide.

<400> SEQUENCE: 1

```
Met Ala Arg Gly Asp Ala Gly Arg Gly Arg Gly Leu Leu Ala Leu Thr
1               5                   10                  15

Phe Cys Leu Leu Ala Ala Arg Gly Glu Leu Leu Leu Pro Gln Glu Thr
            20                  25                  30

Thr Val Glu Leu Ser Cys Gly Val Gly Pro Leu Gln Val Ile Leu Gly
        35                  40                  45

Pro Glu Gln Ala Ala Val Leu Asn Cys Ser Leu Gly Ala Ala Ala Ala
    50                  55                  60

Gly Pro Pro Thr Arg Val Thr Trp Ser Lys Asp Gly Asp Thr Leu Leu
65                  70                  75                  80

Glu His Asp His Leu His Leu Pro Asn Gly Ser Leu Trp Leu Ser
                85                  90                  95

Gln Pro Leu Ala Pro Asn Gly Ser Asp Glu Ser Val Pro Glu Ala Val
            100                 105                 110

Gly Val Ile Glu Gly Asn Tyr Ser Cys Leu Ala His Gly Pro Leu Gly
        115                 120                 125

Val Leu Ala Ser Gln Thr Ala Val Val Lys Leu Ala Thr Leu Ala Asp
    130                 135                 140

Phe Ser Leu His Pro Glu Ser Gln Thr Val Glu Glu Asn Gly Thr Ala
145                 150                 155                 160

Arg Phe Glu Cys His Ile Glu Gly Leu Pro Ala Pro Ile Ile Thr Trp
                165                 170                 175

Glu Lys Asp Gln Val Thr Leu Pro Glu Pro Arg Leu Ile Val Leu
            180                 185                 190

Pro Asn Gly Val Leu Gln Ile Leu Asp Val Gln Glu Ser Asp Ala Gly
        195                 200                 205

Pro Tyr Arg Cys Val Ala Thr Asn Ser Ala Arg Gln His Phe Ser Gln
    210                 215                 220

Glu Ala Leu Leu Ser Val Ala His Arg Gly Ser Leu Ala Ser Thr Arg
225                 230                 235                 240
```

-continued

```
Gly Gln Asp Val Val Ile Val Ala Ala Pro Glu Asn Thr Thr Val Val
                245                 250                 255

Ser Gly Gln Ser Val Val Met Glu Cys Val Ala Ser Ala Asp Pro Thr
            260                 265                 270

Pro Phe Val Ser Trp Val Arg Gln Asp Gly Lys Pro Ile Ser Thr Asp
        275                 280                 285

Val Ile Val Leu Gly Arg Thr Asn Leu Leu Ile Ala Asn Ala Gln Pro
    290                 295                 300

Trp His Ser Gly Val Tyr Val Cys Arg Ala Asn Lys Pro Arg Thr Arg
305                 310                 315                 320

Asp Phe Ala Thr Ala Ala Glu Leu Arg Val Leu Ala Ala Pro Ala
                325                 330                 335

Ile Thr Gln Ala Pro Glu Ala Leu Ser Arg Thr Arg Ala Ser Thr Ala
                340                 345                 350

Arg Phe Val Cys Arg Ala Ser Gly Glu Pro Arg Pro Ala Leu Arg Trp
            355                 360                 365

Leu His Asn Gly Ala Pro Leu Arg Pro Asn Gly Arg Val Lys Val Gln
        370                 375                 380

Gly Gly Gly Gly Ser Leu Val Ile Thr Gln Ile Gly Leu Gln Asp Ala
385                 390                 395                 400

Gly Tyr Tyr Gln Cys Val Ala Glu Asn Ser Ala Gly Met Ala Cys Ala
                405                 410                 415

Ala Ala Ser Leu Ala Val Val Arg Glu Gly Leu Pro Ser Ala Pro
                420                 425                 430

Thr Arg Val Thr Ala Thr Pro Leu Ser Ser Ser Ala Val Leu Val Ala
            435                 440                 445

Trp Glu Arg Pro Glu Met His Ser Glu Gln Ile Ile Gly Phe Ser Leu
        450                 455                 460

His Tyr Gln Lys Ala Arg Gly Met Asp Asn Val Glu Tyr Gln Phe Ala
465                 470                 475                 480

Val Asn Asn Asp Thr Thr Glu Leu Gln Val Arg Asp Leu Glu Pro Asn
                485                 490                 495

Thr Asp Tyr Glu Phe Tyr Val Val Ala Tyr Ser Gln Leu Gly Ala Ser
            500                 505                 510

Arg Thr Ser Thr Pro Ala Leu Val His Thr Leu Asp Asp Val Pro Ser
        515                 520                 525

Ala Ala Pro Gln Leu Ser Leu Ser Ser Pro Asn Pro Ser Asp Ile Arg
    530                 535                 540

Val Ala Trp Leu Pro Leu Pro Pro Ser Leu Ser Asn Gly Gln Val Val
545                 550                 555                 560

Lys Tyr Lys Ile Glu Tyr Gly Leu Gly Lys Glu Asp Gln Ile Phe Ser
                565                 570                 575

Thr Glu Val Arg Gly Asn Glu Thr Gln Leu Met Leu Asn Ser Leu Gln
            580                 585                 590

Pro Asn Lys Val Tyr Arg Val Arg Ile Ser Ala Gly Thr Ala Ala Gly
        595                 600                 605

Phe Gly Ala Pro Ser Gln Trp Met His His Arg Thr Pro Ser Met His
        610                 615                 620

Asn Gln Ser His Val Pro Phe Ala Pro Ala Glu Leu Lys Val Gln Ala
625                 630                 635                 640

Lys Met Glu Ser Leu Val Val Ser Trp Gln Pro Pro His Pro Thr
                645                 650                 655
```

```
Gln Ile Ser Gly Tyr Lys Leu Tyr Trp Arg Glu Val Gly Ala Glu
            660                 665                 670

Glu Ala Asn Gly Asp Arg Leu Pro Gly Gly Arg Gly Asp Gln Ala Trp
        675                 680                 685

Asp Val Gly Pro Val Arg Leu Lys Lys Val Lys Gln Tyr Glu Leu
    690                 695                 700

Thr Gln Leu Val Pro Gly Arg Leu Tyr Glu Val Lys Leu Val Ala Phe
705                 710                 715                 720

Asn Lys His Glu Asp Gly Tyr Ala Ala Val Trp Lys Gly Lys Thr Glu
            725                 730                 735

Lys Ala Pro Ala Pro Asp Met Pro Ile Gln Arg Gly Pro Pro Leu Pro
            740                 745                 750

Pro Ala His Val His Ala Glu Ser Asn Ser Thr Ser Ile Trp Leu
    755                 760                 765

Arg Trp Lys Lys Pro Asp Phe Thr Thr Val Lys Ile Val Asn Tyr Thr
    770                 775                 780

Val Arg Phe Ser Pro Trp Gly Leu Arg Asn Ala Ser Leu Val Thr Tyr
785                 790                 795                 800

Tyr Thr Ser Ser Gly Glu Asp Ile Leu Ile Gly Gly Leu Lys Pro Phe
            805                 810                 815

Thr Lys Tyr Glu Phe Ala Val Gln Ser His Gly Val Asp Met Asp Gly
        820                 825                 830

Pro Phe Gly Ser Val Val Glu Arg Ser Thr Leu Pro Asp Arg Pro Ser
        835                 840                 845

Thr Pro Pro Ser Asp Leu Arg Leu Ser Pro Leu Thr Pro Ser Thr Val
850                 855                 860

Arg Leu His Trp Cys Pro Pro Thr Glu Pro Asn Gly Glu Ile Val Glu
865                 870                 875                 880

Tyr Leu Ile Leu Tyr Ser Ser Asn His Thr Gln Pro Glu His Gln Trp
            885                 890                 895

Thr Leu Leu Thr Thr Gln Gly Asn Ile Phe Ser Ala Glu Val His Gly
        900                 905                 910

Leu Glu Ser Asp Thr Arg Tyr Phe Phe Lys Met Gly Ala Arg Thr Glu
        915                 920                 925

Val Gly Pro Gly Pro Phe Ser Arg Leu Gln Asp Val Ile Thr Leu Gln
    930                 935                 940

Glu Lys Leu Ser Asp Ser Leu Asp Met His Ser Val Thr Gly Ile Ile
945                 950                 955                 960

Val Gly Val Cys Leu Gly Leu Leu Cys Leu Leu Ala Cys Met Cys Ala
            965                 970                 975

Gly Leu Arg Arg Ser Pro His Arg Glu Ser Leu Pro Gly Leu Ser Ser
        980                 985                 990

Thr Ala Thr Pro Gly Asn Pro Ala Leu Tyr Ser Arg Ala Arg Leu Gly
        995                 1000                1005

Pro Pro Ser Pro Pro Ala Ala His Glu Leu Glu Ser Leu Val His Pro
    1010                1015                1020

His Pro Gln Asp Trp Ser Pro Pro Ser Asp Val Glu Asp Arg Ala
1025                1030                1035                1040

Glu Val His Ser Leu Met Gly Gly Val Ser Glu Gly Arg Ser His
                1045                1050                1055

Ser Lys Arg Lys Ile Ser Trp Ala Gln Pro Ser Gly Leu Ser Trp Ala
            1060                1065                1070

Gly Ser Trp Ala Gly Cys Glu Leu Pro Gln Ala Gly Pro Arg Pro Ala
```

```
                    1075                1080                1085

Leu Thr Arg Ala Leu Leu Pro Pro Ala Gly Thr Gly Gln Thr Leu Leu
                1090                1095                1100

Leu Gln Ala Leu Val Tyr Asp Ala Ile Lys Gly Asn Gly Arg Lys Lys
1105                1110                1115                1120

Ser Pro Pro Ala Cys Arg Asn Gln Val Glu Ala Val Ile Val His
                    1125                1130                1135

Ser Asp Phe Ser Ala Ser Asn Gly Asn Pro Asp Leu His Leu Gln Asp
                1140                1145                1150

Leu Glu Pro Glu Asp Pro Leu Pro Pro Glu Ala Pro Asp Leu Ile Ser
                1155                1160                1165

Gly Val Gly Asp Pro Gly Gln Gly Ala Ala Trp Leu Asp Arg Glu Leu
                1170                1175                1180

Gly Gly Cys Glu Leu Ala Ala Pro Gly Pro Asp Arg Leu Thr Cys Leu
1185                1190                1195                1200

Pro Glu Ala Ala Ser Ala Ser Cys Ser Tyr Pro Asp Leu Gln Pro Gly
                    1205                1210                1215

Glu Val Leu Glu Glu Thr Pro Gly Asp Ser Cys Gln Leu Lys Ser Pro
                1220                1225                1230

Cys Pro Leu Gly Ala Ser Pro Gly Leu Pro Arg Ser Pro Val Ser Ser
            1235                1240                1245

Ser Ala
    1250

<210> SEQ ID NO 2
<211> LENGTH: 1226
<212> TYPE: PRT
<213> ORGANISM: Artificial Sequence
<220> FEATURE:
<223> OTHER INFORMATION: Human mature NOPE (25-1250), without signal
      peptide.

<400> SEQUENCE: 2

Glu Leu Leu Leu Pro Gln Glu Thr Thr Val Glu Leu Ser Cys Gly Val
1               5                   10                  15

Gly Pro Leu Gln Val Ile Leu Gly Pro Glu Gln Ala Ala Val Leu Asn
                20                  25                  30

Cys Ser Leu Gly Ala Ala Ala Ala Gly Pro Pro Thr Arg Val Thr Trp
            35                  40                  45

Ser Lys Asp Gly Asp Thr Leu Leu Glu His Asp Leu His Leu Leu
    50                  55                  60

Pro Asn Gly Ser Leu Trp Leu Ser Gln Pro Leu Ala Pro Asn Gly Ser
65                  70                  75                  80

Asp Glu Ser Val Pro Glu Ala Val Gly Val Ile Glu Gly Asn Tyr Ser
                85                  90                  95

Cys Leu Ala His Gly Pro Leu Gly Val Leu Ala Ser Gln Thr Ala Val
                100                 105                 110

Val Lys Leu Ala Thr Leu Ala Asp Phe Ser Leu His Pro Glu Ser Gln
            115                 120                 125

Thr Val Glu Glu Asn Gly Thr Ala Arg Phe Glu Cys His Ile Glu Gly
        130                 135                 140

Leu Pro Ala Pro Ile Ile Thr Trp Glu Lys Asp Gln Val Thr Leu Pro
145                 150                 155                 160

Glu Glu Pro Arg Leu Ile Val Leu Pro Asn Gly Val Leu Gln Ile Leu
                165                 170                 175
```

```
Asp Val Gln Glu Ser Asp Ala Gly Pro Tyr Arg Cys Val Ala Thr Asn
            180                 185                 190

Ser Ala Arg Gln His Phe Ser Gln Glu Ala Leu Leu Ser Val Ala His
        195                 200                 205

Arg Gly Ser Leu Ala Ser Thr Arg Gly Gln Asp Val Ile Val Ala
    210                 215                 220

Ala Pro Glu Asn Thr Thr Val Val Ser Gly Gln Ser Val Val Met Glu
225                 230                 235                 240

Cys Val Ala Ser Ala Asp Pro Thr Pro Phe Val Ser Trp Val Arg Gln
                245                 250                 255

Asp Gly Lys Pro Ile Ser Thr Asp Val Ile Val Leu Gly Arg Thr Asn
            260                 265                 270

Leu Leu Ile Ala Asn Ala Gln Pro Trp His Ser Gly Val Tyr Val Cys
        275                 280                 285

Arg Ala Asn Lys Pro Arg Thr Arg Asp Phe Ala Thr Ala Ala Ala Glu
    290                 295                 300

Leu Arg Val Leu Ala Ala Pro Ala Ile Thr Gln Ala Pro Glu Ala Leu
305                 310                 315                 320

Ser Arg Thr Arg Ala Ser Thr Ala Arg Phe Val Cys Arg Ala Ser Gly
                325                 330                 335

Glu Pro Arg Pro Ala Leu Arg Trp Leu His Asn Gly Ala Pro Leu Arg
            340                 345                 350

Pro Asn Gly Arg Val Lys Val Gln Gly Gly Gly Ser Leu Val Ile
        355                 360                 365

Thr Gln Ile Gly Leu Gln Asp Ala Gly Tyr Tyr Gln Cys Val Ala Glu
370                 375                 380

Asn Ser Ala Gly Met Ala Cys Ala Ala Ala Ser Leu Ala Val Val Val
385                 390                 395                 400

Arg Glu Gly Leu Pro Ser Ala Pro Thr Arg Val Thr Ala Thr Pro Leu
                405                 410                 415

Ser Ser Ser Ala Val Leu Val Ala Trp Glu Arg Pro Glu Met His Ser
            420                 425                 430

Glu Gln Ile Ile Gly Phe Ser Leu His Tyr Gln Lys Ala Arg Gly Met
        435                 440                 445

Asp Asn Val Glu Tyr Gln Phe Ala Val Asn Asn Asp Thr Thr Glu Leu
    450                 455                 460

Gln Val Arg Asp Leu Glu Pro Asn Thr Asp Tyr Glu Phe Tyr Val Val
465                 470                 475                 480

Ala Tyr Ser Gln Leu Gly Ala Ser Arg Thr Ser Thr Pro Ala Leu Val
                485                 490                 495

His Thr Leu Asp Asp Val Pro Ser Ala Ala Pro Gln Leu Ser Leu Ser
            500                 505                 510

Ser Pro Asn Pro Ser Asp Ile Arg Val Ala Trp Leu Pro Leu Pro Pro
        515                 520                 525

Ser Leu Ser Asn Gly Gln Val Val Lys Tyr Lys Ile Glu Tyr Gly Leu
    530                 535                 540

Gly Lys Glu Asp Gln Ile Phe Ser Thr Glu Val Arg Gly Asn Glu Thr
545                 550                 555                 560

Gln Leu Met Leu Asn Ser Leu Gln Pro Asn Lys Val Tyr Arg Val Arg
                565                 570                 575

Ile Ser Ala Gly Thr Ala Ala Gly Phe Gly Ala Pro Ser Gln Trp Met
            580                 585                 590

His His Arg Thr Pro Ser Met His Asn Gln Ser His Val Pro Phe Ala
```

```
                    595                 600                 605
Pro Ala Glu Leu Lys Val Gln Ala Lys Met Glu Ser Leu Val Val Ser
610                 615                 620

Trp Gln Pro Pro His Pro Thr Gln Ile Ser Gly Tyr Lys Leu Tyr
625                 630                 635                 640

Trp Arg Glu Val Gly Ala Glu Glu Ala Asn Gly Asp Arg Leu Pro
                    645                 650                 655

Gly Gly Arg Gly Asp Gln Ala Trp Asp Val Gly Pro Val Arg Leu Lys
                660                 665                 670

Lys Lys Val Lys Gln Tyr Glu Leu Thr Gln Leu Val Pro Gly Arg Leu
            675                 680                 685

Tyr Glu Val Lys Leu Val Ala Phe Asn Lys His Glu Asp Gly Tyr Ala
690                 695                 700

Ala Val Trp Lys Gly Lys Thr Glu Lys Ala Pro Ala Pro Asp Met Pro
705                 710                 715                 720

Ile Gln Arg Gly Pro Pro Leu Pro Pro Ala His Val His Ala Glu Ser
                725                 730                 735

Asn Ser Ser Thr Ser Ile Trp Leu Arg Trp Lys Lys Pro Asp Phe Thr
            740                 745                 750

Thr Val Lys Ile Val Asn Tyr Thr Val Arg Phe Ser Pro Trp Gly Leu
            755                 760                 765

Arg Asn Ala Ser Leu Val Thr Tyr Tyr Thr Ser Ser Gly Glu Asp Ile
770                 775                 780

Leu Ile Gly Gly Leu Lys Pro Phe Thr Lys Tyr Glu Phe Ala Val Gln
785                 790                 795                 800

Ser His Gly Val Asp Met Asp Gly Pro Phe Gly Ser Val Val Glu Arg
                805                 810                 815

Ser Thr Leu Pro Asp Arg Pro Ser Thr Pro Ser Asp Leu Arg Leu
            820                 825                 830

Ser Pro Leu Thr Pro Ser Thr Val Arg Leu His Trp Cys Pro Pro Thr
835                 840                 845

Glu Pro Asn Gly Glu Ile Val Glu Tyr Leu Ile Leu Tyr Ser Ser Asn
850                 855                 860

His Thr Gln Pro Glu His Gln Trp Thr Leu Leu Thr Thr Gln Gly Asn
865                 870                 875                 880

Ile Phe Ser Ala Glu Val His Gly Leu Glu Ser Asp Thr Arg Tyr Phe
                885                 890                 895

Phe Lys Met Gly Ala Arg Thr Glu Val Gly Pro Gly Pro Phe Ser Arg
            900                 905                 910

Leu Gln Asp Val Ile Thr Leu Gln Glu Lys Leu Ser Asp Ser Leu Asp
            915                 920                 925

Met His Ser Val Thr Gly Ile Ile Val Gly Val Cys Leu Gly Leu Leu
930                 935                 940

Cys Leu Leu Ala Cys Met Cys Ala Gly Leu Arg Arg Ser Pro His Arg
945                 950                 955                 960

Glu Ser Leu Pro Gly Leu Ser Ser Thr Ala Thr Pro Gly Asn Pro Ala
                965                 970                 975

Leu Tyr Ser Arg Ala Arg Leu Gly Pro Pro Ser Pro Ala Ala His
            980                 985                 990

Glu Leu Glu Ser Leu Val His Pro His Pro Gln Asp Trp Ser Pro Pro
            995                 1000                1005

Pro Ser Asp Val Glu Asp Arg Ala Glu Val His Ser Leu Met Gly Gly
            1010                1015                1020
```

```
Gly Val Ser Glu Gly Arg Ser His Ser Lys Arg Lys Ile Ser Trp Ala
1025                1030                1035                1040

Gln Pro Ser Gly Leu Ser Trp Ala Gly Ser Trp Ala Gly Cys Glu Leu
                1045                1050                1055

Pro Gln Ala Gly Pro Arg Pro Ala Leu Thr Arg Ala Leu Leu Pro Pro
            1060                1065                1070

Ala Gly Thr Gly Gln Thr Leu Leu Gln Ala Leu Val Tyr Asp Ala
        1075                1080                1085

Ile Lys Gly Asn Gly Arg Lys Lys Ser Pro Pro Ala Cys Arg Asn Gln
1090                1095                1100

Val Glu Ala Glu Val Ile Val His Ser Asp Phe Ser Ala Ser Asn Gly
1105                1110                1115                1120

Asn Pro Asp Leu His Leu Gln Asp Leu Glu Pro Glu Asp Pro Leu Pro
            1125                1130                1135

Pro Glu Ala Pro Asp Leu Ile Ser Gly Val Gly Asp Pro Gly Gln Gly
            1140                1145                1150

Ala Ala Trp Leu Asp Arg Glu Leu Gly Gly Cys Glu Leu Ala Ala Pro
            1155                1160                1165

Gly Pro Asp Arg Leu Thr Cys Leu Pro Glu Ala Ala Ser Ala Ser Cys
        1170                1175                1180

Ser Tyr Pro Asp Leu Gln Pro Gly Glu Val Leu Glu Glu Thr Pro Gly
1185                1190                1195                1200

Asp Ser Cys Gln Leu Lys Ser Pro Cys Pro Leu Gly Ala Ser Pro Gly
                1205                1210                1215

Leu Pro Arg Ser Pro Val Ser Ser Ala
            1220                1225

<210> SEQ ID NO 3
<211> LENGTH: 1252
<212> TYPE: PRT
<213> ORGANISM: Artificial Sequence
<220> FEATURE:
<223> OTHER INFORMATION: Mouse NOPE precursor (1-1252), with signal
      peptide.

<400> SEQUENCE: 3

Met Ala Arg Ala Asp Thr Gly Arg Gly Leu Leu Val Leu Thr Phe Cys
1               5                   10                  15

Leu Leu Ser Ala Arg Gly Glu Leu Pro Leu Pro Gln Glu Thr Thr Val
                20                  25                  30

Lys Leu Ser Cys Asp Glu Gly Pro Leu Gln Val Ile Leu Gly Pro Glu
            35                  40                  45

Gln Ala Val Val Leu Asp Cys Thr Leu Gly Ala Thr Ala Ala Gly Pro
        50                  55                  60

Pro Thr Arg Val Thr Trp Ser Lys Asp Gly Asp Thr Val Leu Glu His
65                  70                  75                  80

Glu Asn Leu His Leu Leu Pro Asn Gly Ser Leu Trp Leu Ser Ser Pro
                85                  90                  95

Leu Glu Gln Glu Asp Ser Asp Glu Glu Ala Leu Arg Ile Trp Lys
            100                 105                 110

Val Thr Glu Gly Ser Tyr Ser Cys Leu Ala His Ser Pro Leu Gly Val
            115                 120                 125

Val Ala Ser Gln Val Ala Val Val Lys Leu Ala Thr Leu Glu Asp Phe
        130                 135                 140

Ser Leu His Pro Glu Ser Gln Ile Val Glu Glu Asn Gly Thr Ala Arg
```

-continued

```
            145                 150                 155                 160
        Phe Glu Cys His Thr Lys Gly Leu Pro Ala Pro Ile Ile Thr Trp Glu
                        165                 170                 175
        Lys Asp Gln Val Thr Val Pro Glu Glu Ser Arg Leu Ile Thr Leu Pro
                        180                 185                 190
        Asn Gly Val Leu Gln Ile Leu Asp Val Gln Asp Ser Asp Ala Gly Ser
                        195                 200                 205
        Tyr Arg Cys Val Ala Thr Asn Ser Ala Arg Gln Arg Phe Ser Gln Glu
                210                 215                 220
        Ala Ser Leu Thr Val Ala Leu Arg Gly Ser Leu Glu Ala Thr Arg Gly
        225                 230                 235                 240
        Gln Asp Val Val Ile Val Ala Ala Pro Glu Asn Thr Val Val Ser
                        245                 250                 255
        Gly Gln Ser Val Val Met Glu Cys Val Ala Ser Ala Asp Pro Thr Pro
                        260                 265                 270
        Phe Val Ser Trp Val Arg Gln Asp Gly Lys Pro Ile Ser Thr Asp Val
                        275                 280                 285
        Ile Val Leu Gly Arg Thr Asn Leu Leu Ile Ala Ser Ala Gln Pro Arg
                        290                 295                 300
        His Ser Gly Val Tyr Val Cys Arg Ala Asn Lys Pro Arg Thr Arg Asp
        305                 310                 315                 320
        Phe Ala Thr Ala Ala Glu Leu Arg Val Leu Ala Pro Ala Ile
                        325                 330                 335
        Ser Gln Ala Pro Glu Ala Leu Ser Arg Thr Arg Ala Ser Thr Ala Arg
                        340                 345                 350
        Phe Val Cys Arg Ala Ser Gly Glu Pro Arg Pro Ala Leu His Trp Leu
                        355                 360                 365
        His Asp Gly Ile Pro Leu Arg Pro Asn Gly Arg Val Lys Val Gln Gly
                        370                 375                 380
        Gly Gly Gly Ser Leu Val Ile Thr Gln Ile Gly Leu Gln Asp Ala Gly
        385                 390                 395                 400
        Tyr Tyr Gln Cys Val Ala Glu Asn Ser Ala Gly Thr Ala Cys Ala Ala
                        405                 410                 415
        Ala Pro Leu Ala Val Val Arg Glu Gly Leu Pro Ser Ala Pro Thr
                        420                 425                 430
        Arg Val Thr Ala Thr Pro Leu Ser Ser Ser Val Leu Val Ala Trp
                        435                 440                 445
        Glu Arg Pro Glu Leu His Ser Glu Gln Ile Ile Gly Phe Ser Leu His
        450                 455                 460
        Tyr Gln Lys Ala Arg Gly Val Asp Asn Val Glu Tyr Gln Phe Ala Val
        465                 470                 475                 480
        Asn Asn Asp Thr Thr Glu Leu Gln Val Arg Asp Leu Glu Pro Asn Thr
                        485                 490                 495
        Asp Tyr Glu Phe Tyr Val Val Ala Tyr Ser Gln Leu Gly Ala Ser Arg
                        500                 505                 510
        Thr Ser Ser Pro Ala Leu Val His Thr Leu Asp Asp Val Pro Ser Ala
                        515                 520                 525
        Ala Pro Gln Leu Thr Leu Ser Ser Pro Asn Pro Ser Asp Ile Arg Val
                        530                 535                 540
        Ala Trp Leu Pro Leu Pro Ser Ser Leu Ser Asn Gly Gln Val Leu Lys
        545                 550                 555                 560
        Tyr Lys Ile Glu Tyr Gly Leu Gly Lys Glu Asp Gln Val Phe Ser Thr
                        565                 570                 575
```

```
Glu Val Pro Gly Asn Glu Thr Gln Leu Thr Leu Asn Ser Leu Gln Pro
            580                 585                 590

Asn Lys Val Tyr Arg Val Arg Ile Ser Ala Gly Thr Gly Ala Gly Tyr
        595                 600                 605

Gly Val Pro Ser Gln Trp Met Gln His Arg Thr Pro Gly Val His Asn
610                 615                 620

Gln Ser His Val Pro Phe Ala Pro Ala Glu Leu Lys Val Arg Ala Lys
625                 630                 635                 640

Met Glu Ser Leu Val Val Ser Trp Gln Pro Pro His Pro Thr Gln
            645                 650                 655

Ile Ser Gly Tyr Lys Leu Tyr Trp Arg Glu Val Gly Thr Glu Glu
            660                 665                 670

Ala Asp Gly Asp Arg Pro Pro Gly Arg Gly Asp Gln Ala Trp Asp
            675                 680                 685

Val Gly Pro Val Arg Leu Lys Lys Val Lys Gln Tyr Glu Leu Thr
            690                 695                 700

Gln Leu Val Pro Gly Arg Leu Tyr Glu Val Lys Leu Val Ala Phe Asn
705                 710                 715                 720

Lys His Glu Asp Gly Tyr Ala Ala Val Trp Lys Gly Lys Thr Glu Lys
            725                 730                 735

Ala Pro Thr Pro Asp Leu Pro Ile Gln Arg Gly Pro Pro Leu Pro Pro
            740                 745                 750

Ala His Val His Ala Glu Ser Asn Ser Ser Thr Ser Ile Trp Leu Arg
            755                 760                 765

Trp Lys Lys Pro Asp Phe Thr Thr Val Lys Ile Val Asn Tyr Thr Val
770                 775                 780

Arg Phe Gly Pro Trp Gly Leu Arg Asn Ala Ser Leu Val Thr Tyr Tyr
785                 790                 795                 800

Thr Ser Ser Gly Glu Asp Ile Leu Ile Gly Gly Leu Lys Pro Phe Thr
            805                 810                 815

Lys Tyr Glu Phe Ala Val Gln Ser His Gly Val Asp Met Asp Gly Pro
            820                 825                 830

Phe Gly Ser Val Val Glu Arg Ser Thr Leu Pro Asp Arg Pro Ser Thr
            835                 840                 845

Pro Pro Ser Asp Leu Arg Leu Ser Pro Leu Thr Pro Ser Thr Val Arg
            850                 855                 860

Leu His Trp Cys Pro Pro Thr Glu Pro Asn Gly Glu Ile Val Glu Tyr
865                 870                 875                 880

Leu Ile Leu Tyr Ser Asn Asn His Thr Gln Pro Glu His Gln Trp Thr
                885                 890                 895

Leu Leu Thr Thr Glu Gly Asn Ile Phe Ser Ala Glu Val His Gly Leu
            900                 905                 910

Glu Ser Asp Thr Arg Tyr Phe Phe Lys Met Gly Ala Arg Thr Glu Val
            915                 920                 925

Gly Pro Gly Pro Phe Ser Arg Leu Gln Asp Val Ile Thr Leu Gln Lys
            930                 935                 940

Thr Phe Ser Asp Ser Leu Asp Val His Ala Val Thr Gly Ile Ile Val
945                 950                 955                 960

Gly Val Cys Leu Gly Leu Leu Cys Leu Leu Ala Cys Met Cys Ala Gly
                965                 970                 975

Leu Arg Arg Ser Ser His Arg Glu Ala Leu Pro Gly Leu Ser Ser Ser
            980                 985                 990
```

```
Gly Thr Pro Gly Asn Pro Ala Leu Tyr Thr Arg Ala Arg Leu Gly Pro
        995                 1000                1005

Pro Ser Val Pro Ala Ala His Glu Leu Glu Ser Leu Val His Pro Arg
    1010                1015                1020

Pro Gln Asp Trp Ser Pro Pro Ser Asp Val Glu Asp Lys Ala Glu
1025                1030                1035                1040

Val His Ser Leu Met Gly Gly Ser Val Ser Asp Cys Arg Gly His Ser
            1045                1050                1055

Lys Arg Lys Ile Ser Trp Ala Gln Ala Gly Gly Pro Asn Trp Ala Gly
        1060                1065                1070

Ser Trp Ala Gly Cys Glu Leu Pro Gln Gly Ser Gly Pro Arg Pro Ala
    1075                1080                1085

Leu Thr Arg Ala Leu Leu Pro Pro Ala Gly Thr Gly Gln Thr Leu Leu
1090                1095                1100

Leu Gln Ala Leu Val Tyr Asp Ala Ile Lys Ser Asn Gly Arg Lys Lys
1105                1110                1115                1120

Pro Ser Pro Ala Cys Arg Asn Gln Val Glu Ala Glu Val Ile Val His
            1125                1130                1135

Ser Asp Phe Gly Ala Ser Lys Gly Cys Pro Asp Leu His Leu Gln Asp
        1140                1145                1150

Leu Glu Pro Glu Glu Pro Leu Thr Ala Glu Thr Leu Pro Ser Thr Ser
    1155                1160                1165

Gly Ala Val Asp Leu Ser Gln Gly Ala Asp Trp Leu Gly Arg Glu Leu
1170                1175                1180

Gly Gly Cys Gln Pro Thr Thr Ser Gly Pro Glu Arg Leu Thr Cys Leu
1185                1190                1195                1200

Pro Glu Ala Ala Ser Ala Ser Cys Ser Cys Ser Asp Leu Gln Pro Ser
            1205                1210                1215

Thr Ala Ile Glu Glu Ala Pro Gly Lys Ser Cys Gln Pro Lys Ala Leu
        1220                1225                1230

Cys Pro Leu Thr Val Ser Pro Ser Leu Pro Arg Ala Pro Val Ser Ser
    1235                1240                1245

Ala Gln Val Pro
    1250

<210> SEQ ID NO 4
<211> LENGTH: 1230
<212> TYPE: PRT
<213> ORGANISM: Artificial Sequence
<220> FEATURE:
<223> OTHER INFORMATION: Mouse mature NOPE (23-1252), without signal
      peptide.

<400> SEQUENCE: 4

Glu Leu Pro Leu Pro Gln Glu Thr Thr Val Lys Leu Ser Cys Asp Glu
1               5                   10                  15

Gly Pro Leu Gln Val Ile Leu Gly Pro Glu Gln Ala Val Val Leu Asp
            20                  25                  30

Cys Thr Leu Gly Ala Thr Ala Ala Gly Pro Pro Thr Arg Val Thr Trp
        35                  40                  45

Ser Lys Asp Gly Asp Thr Val Leu Glu His Glu Asn Leu His Leu Leu
    50                  55                  60

Pro Asn Gly Ser Leu Trp Leu Ser Ser Pro Leu Glu Gln Glu Asp Ser
65                  70                  75                  80

Asp Asp Glu Glu Ala Leu Arg Ile Trp Lys Val Thr Glu Gly Ser Tyr
                85                  90                  95
```

-continued

```
Ser Cys Leu Ala His Ser Pro Leu Gly Val Ala Ser Gln Val Ala
            100                 105                 110

Val Val Lys Leu Ala Thr Leu Glu Asp Phe Ser Leu His Pro Glu Ser
        115                 120                 125

Gln Ile Val Glu Glu Asn Gly Thr Ala Arg Phe Glu Cys His Thr Lys
    130                 135                 140

Gly Leu Pro Ala Pro Ile Ile Thr Trp Glu Lys Asp Gln Val Thr Val
145                 150                 155                 160

Pro Glu Glu Ser Arg Leu Ile Thr Leu Pro Asn Gly Val Leu Gln Ile
                165                 170                 175

Leu Asp Val Gln Asp Ser Asp Ala Gly Ser Tyr Arg Cys Val Ala Thr
            180                 185                 190

Asn Ser Ala Arg Gln Arg Phe Ser Gln Glu Ala Ser Leu Thr Val Ala
        195                 200                 205

Leu Arg Gly Ser Leu Glu Ala Thr Arg Gly Gln Asp Val Val Ile Val
    210                 215                 220

Ala Ala Pro Glu Asn Thr Thr Val Val Ser Gly Gln Ser Val Val Met
225                 230                 235                 240

Glu Cys Val Ala Ser Ala Asp Pro Thr Pro Phe Val Ser Trp Val Arg
                245                 250                 255

Gln Asp Gly Lys Pro Ile Ser Thr Asp Val Ile Val Leu Gly Arg Thr
            260                 265                 270

Asn Leu Leu Ile Ala Ser Ala Gln Pro Arg His Ser Gly Val Tyr Val
        275                 280                 285

Cys Arg Ala Asn Lys Pro Arg Thr Arg Asp Phe Ala Thr Ala Ala Ala
    290                 295                 300

Glu Leu Arg Val Leu Ala Ala Pro Ala Ile Ser Gln Ala Pro Glu Ala
305                 310                 315                 320

Leu Ser Arg Thr Arg Ala Ser Thr Ala Arg Phe Val Cys Arg Ala Ser
                325                 330                 335

Gly Glu Pro Arg Pro Ala Leu His Trp Leu His Asp Gly Ile Pro Leu
            340                 345                 350

Arg Pro Asn Gly Arg Val Lys Val Gln Gly Gly Gly Ser Leu Val
        355                 360                 365

Ile Thr Gln Ile Gly Leu Gln Asp Ala Gly Tyr Tyr Gln Cys Val Ala
    370                 375                 380

Glu Asn Ser Ala Gly Thr Ala Cys Ala Ala Ala Pro Leu Ala Val Val
385                 390                 395                 400

Val Arg Glu Gly Leu Pro Ser Ala Pro Thr Arg Val Thr Ala Thr Pro
                405                 410                 415

Leu Ser Ser Ser Val Leu Val Ala Trp Glu Arg Pro Glu Leu His
            420                 425                 430

Ser Glu Gln Ile Ile Gly Phe Ser Leu His Tyr Gln Lys Ala Arg Gly
        435                 440                 445

Val Asp Asn Val Glu Tyr Gln Phe Ala Val Asn Asn Asp Thr Thr Glu
    450                 455                 460

Leu Gln Val Arg Asp Leu Glu Pro Asn Thr Asp Tyr Glu Phe Tyr Val
465                 470                 475                 480

Val Ala Tyr Ser Gln Leu Gly Ala Ser Arg Thr Ser Ser Pro Ala Leu
                485                 490                 495

Val His Thr Leu Asp Asp Val Pro Ser Ala Ala Pro Gln Leu Thr Leu
            500                 505                 510
```

```
Ser Ser Pro Asn Pro Ser Asp Ile Arg Val Ala Trp Leu Pro Leu Pro
            515                 520                 525
Ser Ser Leu Ser Asn Gly Gln Val Leu Lys Tyr Lys Ile Glu Tyr Gly
530                 535                 540
Leu Gly Lys Glu Asp Gln Val Phe Ser Thr Glu Val Pro Gly Asn Glu
545                 550                 555                 560
Thr Gln Leu Thr Leu Asn Ser Leu Gln Pro Asn Lys Val Tyr Arg Val
                565                 570                 575
Arg Ile Ser Ala Gly Thr Gly Ala Gly Tyr Gly Val Pro Ser Gln Trp
            580                 585                 590
Met Gln His Arg Thr Pro Gly Val His Asn Gln Ser His Val Pro Phe
        595                 600                 605
Ala Pro Ala Glu Leu Lys Val Arg Ala Lys Met Glu Ser Leu Val Val
610                 615                 620
Ser Trp Gln Pro Pro His Pro Thr Gln Ile Ser Gly Tyr Lys Leu
625                 630                 635                 640
Tyr Trp Arg Glu Val Gly Thr Glu Glu Ala Asp Gly Asp Arg Pro
                645                 650                 655
Pro Gly Gly Arg Gly Asp Gln Ala Trp Asp Val Gly Pro Val Arg Leu
            660                 665                 670
Lys Lys Lys Val Lys Gln Tyr Glu Leu Thr Gln Leu Val Pro Gly Arg
            675                 680                 685
Leu Tyr Glu Val Lys Leu Val Ala Phe Asn Lys His Glu Asp Gly Tyr
        690                 695                 700
Ala Ala Val Trp Lys Gly Lys Thr Glu Lys Ala Pro Thr Pro Asp Leu
705                 710                 715                 720
Pro Ile Gln Arg Gly Pro Pro Leu Pro Pro Ala His Val His Ala Glu
                725                 730                 735
Ser Asn Ser Ser Thr Ser Ile Trp Leu Arg Trp Lys Lys Pro Asp Phe
            740                 745                 750
Thr Thr Val Lys Ile Val Asn Tyr Thr Val Arg Phe Gly Pro Trp Gly
            755                 760                 765
Leu Arg Asn Ala Ser Leu Val Thr Tyr Tyr Thr Ser Ser Gly Glu Asp
770                 775                 780
Ile Leu Ile Gly Gly Leu Lys Pro Phe Thr Lys Tyr Glu Phe Ala Val
785                 790                 795                 800
Gln Ser His Gly Val Asp Met Asp Gly Pro Phe Gly Ser Val Val Glu
                805                 810                 815
Arg Ser Thr Leu Pro Asp Arg Pro Ser Thr Pro Pro Ser Asp Leu Arg
            820                 825                 830
Leu Ser Pro Leu Thr Pro Ser Thr Val Arg Leu His Trp Cys Pro Pro
            835                 840                 845
Thr Glu Pro Asn Gly Glu Ile Val Glu Tyr Leu Ile Leu Tyr Ser Asn
850                 855                 860
Asn His Thr Gln Pro Glu His Gln Trp Thr Leu Leu Thr Thr Glu Gly
865                 870                 875                 880
Asn Ile Phe Ser Ala Glu Val His Gly Leu Glu Ser Asp Thr Arg Tyr
                885                 890                 895
Phe Phe Lys Met Gly Ala Arg Thr Glu Val Gly Pro Gly Pro Phe Ser
            900                 905                 910
Arg Leu Gln Asp Val Ile Thr Leu Gln Lys Thr Phe Ser Asp Ser Leu
            915                 920                 925
Asp Val His Ala Val Thr Gly Ile Ile Val Gly Val Cys Leu Gly Leu
```

```
            930             935             940
Leu Cys Leu Leu Ala Cys Met Cys Ala Gly Leu Arg Arg Ser Ser His
945                 950                 955                 960

Arg Glu Ala Leu Pro Gly Leu Ser Ser Ser Gly Thr Pro Gly Asn Pro
                965                 970                 975

Ala Leu Tyr Thr Arg Ala Arg Leu Gly Pro Pro Ser Val Pro Ala Ala
            980                 985                 990

His Glu Leu Glu Ser Leu Val His Pro Arg Pro Gln Asp Trp Ser Pro
        995                 1000                1005

Pro Pro Ser Asp Val Glu Asp Lys Ala Glu Val His Ser Leu Met Gly
    1010                1015                1020

Gly Ser Val Ser Asp Cys Arg Gly His Ser Lys Arg Lys Ile Ser Trp
1025                1030                1035                1040

Ala Gln Ala Gly Gly Pro Asn Trp Ala Gly Ser Trp Ala Gly Cys Glu
                1045                1050                1055

Leu Pro Gln Gly Ser Gly Pro Arg Pro Ala Leu Thr Arg Ala Leu Leu
            1060                1065                1070

Pro Pro Ala Gly Thr Gly Gln Thr Leu Leu Leu Gln Ala Leu Val Tyr
        1075                1080                1085

Asp Ala Ile Lys Ser Asn Gly Arg Lys Lys Pro Ser Pro Ala Cys Arg
    1090                1095                1100

Asn Gln Val Glu Ala Glu Val Ile Val His Ser Asp Phe Gly Ala Ser
1105                1110                1115                1120

Lys Gly Cys Pro Asp Leu His Leu Gln Asp Leu Glu Pro Glu Pro
                1125                1130                1135

Leu Thr Ala Glu Thr Leu Pro Ser Thr Ser Gly Ala Val Asp Leu Ser
            1140                1145                1150

Gln Gly Ala Asp Trp Leu Gly Arg Glu Leu Gly Gly Cys Gln Pro Thr
        1155                1160                1165

Thr Ser Gly Pro Glu Arg Leu Thr Cys Leu Pro Glu Ala Ala Ser Ala
    1170                1175                1180

Ser Cys Ser Cys Ser Asp Leu Gln Pro Ser Thr Ala Ile Glu Glu Ala
1185                1190                1195                1200

Pro Gly Lys Ser Cys Gln Pro Lys Ala Leu Cys Pro Leu Thr Val Ser
                1205                1210                1215

Pro Ser Leu Pro Arg Ala Pro Val Ser Ser Ala Gln Val Pro
            1220                1225                1230

<210> SEQ ID NO 5
<211> LENGTH: 957
<212> TYPE: PRT
<213> ORGANISM: Artificial Sequence
<220> FEATURE:
<223> OTHER INFORMATION: Human NOPE extracellular domain (ECD) (1-957),
      with signal peptide.

<400> SEQUENCE: 5

Met Ala Arg Gly Asp Ala Gly Arg Gly Arg Gly Leu Leu Ala Leu Thr
1               5                   10                  15

Phe Cys Leu Leu Ala Ala Arg Gly Glu Leu Leu Leu Pro Gln Glu Thr
                20                  25                  30

Thr Val Glu Leu Ser Cys Gly Val Gly Pro Leu Gln Val Ile Leu Gly
            35                  40                  45

Pro Glu Gln Ala Ala Val Leu Asn Cys Ser Leu Gly Ala Ala Ala Ala
        50                  55                  60
```

```
Gly Pro Pro Thr Arg Val Thr Trp Ser Lys Asp Gly Asp Thr Leu Leu
 65                  70                  75                  80

Glu His Asp His Leu His Leu Leu Pro Asn Gly Ser Leu Trp Leu Ser
                 85                  90                  95

Gln Pro Leu Ala Pro Asn Gly Ser Asp Glu Ser Val Pro Glu Ala Val
            100                 105                 110

Gly Val Ile Glu Gly Asn Tyr Ser Cys Leu Ala His Gly Pro Leu Gly
        115                 120                 125

Val Leu Ala Ser Gln Thr Ala Val Val Lys Leu Ala Thr Leu Ala Asp
    130                 135                 140

Phe Ser Leu His Pro Glu Ser Gln Thr Val Glu Glu Asn Gly Thr Ala
145                 150                 155                 160

Arg Phe Glu Cys His Ile Glu Gly Leu Pro Ala Pro Ile Ile Thr Trp
                165                 170                 175

Glu Lys Asp Gln Val Thr Leu Pro Glu Glu Pro Arg Leu Ile Val Leu
            180                 185                 190

Pro Asn Gly Val Leu Gln Ile Leu Asp Val Gln Glu Ser Asp Ala Gly
        195                 200                 205

Pro Tyr Arg Cys Val Ala Thr Asn Ser Ala Arg Gln His Phe Ser Gln
    210                 215                 220

Glu Ala Leu Leu Ser Val Ala His Arg Gly Ser Leu Ala Ser Thr Arg
225                 230                 235                 240

Gly Gln Asp Val Val Ile Val Ala Ala Pro Glu Asn Thr Thr Val Val
                245                 250                 255

Ser Gly Gln Ser Val Val Met Glu Cys Val Ala Ser Ala Asp Pro Thr
            260                 265                 270

Pro Phe Val Ser Trp Val Arg Gln Asp Gly Lys Pro Ile Ser Thr Asp
        275                 280                 285

Val Ile Val Leu Gly Arg Thr Asn Leu Leu Ile Ala Asn Ala Gln Pro
    290                 295                 300

Trp His Ser Gly Val Tyr Val Cys Arg Ala Asn Lys Pro Arg Thr Arg
305                 310                 315                 320

Asp Phe Ala Thr Ala Ala Ala Glu Leu Arg Val Leu Ala Ala Pro Ala
                325                 330                 335

Ile Thr Gln Ala Pro Glu Ala Leu Ser Arg Thr Arg Ala Ser Thr Ala
            340                 345                 350

Arg Phe Val Cys Arg Ala Ser Gly Glu Pro Arg Pro Ala Leu Arg Trp
        355                 360                 365

Leu His Asn Gly Ala Pro Leu Arg Pro Asn Gly Arg Val Lys Val Gln
    370                 375                 380

Gly Gly Gly Gly Ser Leu Val Ile Thr Gln Ile Gly Leu Gln Asp Ala
385                 390                 395                 400

Gly Tyr Tyr Gln Cys Val Ala Glu Asn Ser Ala Gly Met Ala Cys Ala
                405                 410                 415

Ala Ala Ser Leu Ala Val Val Arg Glu Gly Leu Pro Ser Ala Pro Pro
            420                 425                 430

Thr Arg Val Thr Ala Thr Pro Leu Ser Ser Ser Ala Val Leu Val Ala
        435                 440                 445

Trp Glu Arg Pro Glu Met His Ser Glu Gln Ile Ile Gly Phe Ser Leu
    450                 455                 460

His Tyr Gln Lys Ala Arg Gly Met Asp Asn Val Glu Tyr Gln Phe Ala
465                 470                 475                 480

Val Asn Asn Asp Thr Thr Glu Leu Gln Val Arg Asp Leu Glu Pro Asn
```

```
                485               490               495
Thr Asp Tyr Glu Phe Tyr Val Val Ala Tyr Ser Gln Leu Gly Ala Ser
            500               505               510

Arg Thr Ser Thr Pro Ala Leu Val His Thr Leu Asp Asp Val Pro Ser
            515               520               525

Ala Ala Pro Gln Leu Ser Leu Ser Ser Pro Asn Pro Ser Asp Ile Arg
        530               535               540

Val Ala Trp Leu Pro Leu Pro Pro Ser Leu Ser Asn Gly Gln Val Val
545               550               555               560

Lys Tyr Lys Ile Glu Tyr Gly Leu Gly Lys Glu Asp Gln Ile Phe Ser
                565               570               575

Thr Glu Val Arg Gly Asn Glu Thr Gln Leu Met Leu Asn Ser Leu Gln
                580               585               590

Pro Asn Lys Val Tyr Arg Val Arg Ile Ser Ala Gly Thr Ala Ala Gly
            595               600               605

Phe Gly Ala Pro Ser Gln Trp Met His His Arg Thr Pro Ser Met His
        610               615               620

Asn Gln Ser His Val Pro Phe Ala Pro Ala Glu Leu Lys Val Gln Ala
625               630               635               640

Lys Met Glu Ser Leu Val Val Ser Trp Gln Pro Pro His Pro Pro Thr
                645               650               655

Gln Ile Ser Gly Tyr Lys Leu Tyr Trp Arg Glu Val Gly Ala Glu Glu
                660               665               670

Glu Ala Asn Gly Asp Arg Leu Pro Gly Gly Arg Gly Asp Gln Ala Trp
            675               680               685

Asp Val Gly Pro Val Arg Leu Lys Lys Val Lys Gln Tyr Glu Leu
        690               695               700

Thr Gln Leu Val Pro Gly Arg Leu Tyr Glu Val Lys Leu Val Ala Phe
705               710               715               720

Asn Lys His Glu Asp Gly Tyr Ala Ala Val Trp Lys Gly Lys Thr Glu
                725               730               735

Lys Ala Pro Ala Pro Asp Met Pro Ile Gln Arg Gly Pro Pro Leu Pro
            740               745               750

Pro Ala His Val His Ala Glu Ser Asn Ser Ser Thr Ser Ile Trp Leu
        755               760               765

Arg Trp Lys Lys Pro Asp Phe Thr Thr Val Lys Ile Val Asn Tyr Thr
        770               775               780

Val Arg Phe Ser Pro Trp Gly Leu Arg Asn Ala Ser Leu Val Thr Tyr
785               790               795               800

Tyr Thr Ser Ser Gly Glu Asp Ile Leu Ile Gly Gly Leu Lys Pro Phe
            805               810               815

Thr Lys Tyr Glu Phe Ala Val Gln Ser His Gly Val Asp Met Asp Gly
            820               825               830

Pro Phe Gly Ser Val Val Glu Arg Ser Thr Leu Pro Asp Arg Pro Ser
        835               840               845

Thr Pro Pro Ser Asp Leu Arg Leu Ser Pro Leu Thr Pro Ser Thr Val
    850               855               860

Arg Leu His Trp Cys Pro Pro Thr Glu Pro Asn Gly Glu Ile Val Glu
865               870               875               880

Tyr Leu Ile Leu Tyr Ser Ser Asn His Thr Gln Pro Glu His Gln Trp
                885               890               895

Thr Leu Leu Thr Thr Gln Gly Asn Ile Phe Ser Ala Glu Val His Gly
            900               905               910
```

```
Leu Glu Ser Asp Thr Arg Tyr Phe Phe Lys Met Gly Ala Arg Thr Glu
            915                 920                 925

Val Gly Pro Gly Pro Phe Ser Arg Leu Gln Asp Val Ile Thr Leu Gln
    930                 935                 940

Glu Lys Leu Ser Asp Ser Leu Asp Met His Ser Val Thr
945                 950                 955

<210> SEQ ID NO 6
<211> LENGTH: 931
<212> TYPE: PRT
<213> ORGANISM: Artificial Sequence
<220> FEATURE:
<223> OTHER INFORMATION: Human NOPE ECD (25-955), without signal
      peptide.

<400> SEQUENCE: 6

Glu Leu Leu Leu Pro Gln Glu Thr Thr Val Glu Leu Ser Cys Gly Val
1               5                   10                  15

Gly Pro Leu Gln Val Ile Leu Gly Pro Glu Gln Ala Ala Val Leu Asn
            20                  25                  30

Cys Ser Leu Gly Ala Ala Ala Gly Pro Pro Thr Arg Val Thr Trp
        35                  40                  45

Ser Lys Asp Gly Asp Thr Leu Leu Glu His Asp His Leu His Leu Leu
    50                  55                  60

Pro Asn Gly Ser Leu Trp Leu Ser Gln Pro Leu Ala Pro Asn Gly Ser
65                  70                  75                  80

Asp Glu Ser Val Pro Glu Ala Val Gly Val Ile Glu Gly Asn Tyr Ser
                85                  90                  95

Cys Leu Ala His Gly Pro Leu Gly Val Leu Ala Ser Gln Thr Ala Val
            100                 105                 110

Val Lys Leu Ala Thr Leu Ala Asp Phe Ser Leu His Pro Glu Ser Gln
        115                 120                 125

Thr Val Glu Glu Asn Gly Thr Ala Arg Phe Glu Cys His Ile Glu Gly
    130                 135                 140

Leu Pro Ala Pro Ile Ile Thr Trp Glu Lys Asp Gln Val Thr Leu Pro
145                 150                 155                 160

Glu Glu Pro Arg Leu Ile Val Leu Pro Asn Gly Val Leu Gln Ile Leu
                165                 170                 175

Asp Val Gln Glu Ser Asp Ala Gly Pro Tyr Arg Cys Val Ala Thr Asn
            180                 185                 190

Ser Ala Arg Gln His Phe Ser Gln Glu Ala Leu Leu Ser Val Ala His
        195                 200                 205

Arg Gly Ser Leu Ala Ser Thr Arg Gly Gln Asp Val Val Ile Val Ala
    210                 215                 220

Ala Pro Glu Asn Thr Thr Val Ser Gly Gln Ser Val Val Met Glu
225                 230                 235                 240

Cys Val Ala Ser Ala Asp Pro Thr Pro Phe Val Ser Trp Val Arg Gln
                245                 250                 255

Asp Gly Lys Pro Ile Ser Thr Asp Val Ile Val Leu Gly Arg Thr Asn
            260                 265                 270

Leu Leu Ile Ala Asn Ala Gln Pro Trp His Ser Gly Val Tyr Val Cys
        275                 280                 285

Arg Ala Asn Lys Pro Arg Thr Arg Asp Phe Ala Thr Ala Ala Ala Glu
    290                 295                 300

Leu Arg Val Leu Ala Ala Pro Ala Ile Thr Gln Ala Pro Glu Ala Leu
```

```
            305                 310                 315                 320
Ser Arg Thr Arg Ala Ser Thr Ala Arg Phe Val Cys Arg Ala Ser Gly
                325                 330                 335

Glu Pro Arg Pro Ala Leu Arg Trp Leu His Asn Gly Ala Pro Leu Arg
                340                 345                 350

Pro Asn Gly Arg Val Lys Val Gln Gly Gly Gly Ser Leu Val Ile
                355                 360                 365

Thr Gln Ile Gly Leu Gln Asp Ala Gly Tyr Tyr Gln Cys Val Ala Glu
    370                 375                 380

Asn Ser Ala Gly Met Ala Cys Ala Ala Ala Ser Leu Ala Val Val Val
385                 390                 395                 400

Arg Glu Gly Leu Pro Ser Ala Pro Thr Arg Val Thr Ala Thr Pro Leu
                405                 410                 415

Ser Ser Ser Ala Val Leu Val Ala Trp Glu Arg Pro Glu Met His Ser
                420                 425                 430

Glu Gln Ile Ile Gly Phe Ser Leu His Tyr Gln Lys Ala Arg Gly Met
            435                 440                 445

Asp Asn Val Glu Tyr Gln Phe Ala Val Asn Asn Asp Thr Thr Glu Leu
    450                 455                 460

Gln Val Arg Asp Leu Glu Pro Asn Thr Asp Tyr Glu Phe Tyr Val Val
465                 470                 475                 480

Ala Tyr Ser Gln Leu Gly Ala Ser Arg Thr Ser Thr Pro Ala Leu Val
                485                 490                 495

His Thr Leu Asp Asp Val Pro Ser Ala Ala Pro Gln Leu Ser Leu Ser
                500                 505                 510

Ser Pro Asn Pro Ser Asp Ile Arg Val Ala Trp Leu Pro Leu Pro Pro
            515                 520                 525

Ser Leu Ser Asn Gly Gln Val Val Lys Tyr Lys Ile Glu Tyr Gly Leu
            530                 535                 540

Gly Lys Glu Asp Gln Ile Phe Ser Thr Glu Val Arg Gly Asn Glu Thr
545                 550                 555                 560

Gln Leu Met Leu Asn Ser Leu Gln Pro Asn Lys Val Tyr Arg Val Arg
                565                 570                 575

Ile Ser Ala Gly Thr Ala Ala Gly Phe Gly Ala Pro Ser Gln Trp Met
            580                 585                 590

His His Arg Thr Pro Ser Met His Asn Gln Ser His Val Pro Phe Ala
            595                 600                 605

Pro Ala Glu Leu Lys Val Gln Ala Lys Met Glu Ser Leu Val Val Ser
            610                 615                 620

Trp Gln Pro Pro Pro His Pro Thr Gln Ile Ser Gly Tyr Lys Leu Tyr
625                 630                 635                 640

Trp Arg Glu Val Gly Ala Glu Glu Ala Asn Gly Asp Arg Leu Pro
                645                 650                 655

Gly Gly Arg Gly Asp Gln Ala Trp Asp Val Gly Pro Val Arg Leu Lys
                660                 665                 670

Lys Lys Val Lys Gln Tyr Glu Leu Thr Gln Leu Val Pro Gly Arg Leu
            675                 680                 685

Tyr Glu Val Lys Leu Val Ala Phe Asn Lys His Glu Asp Gly Tyr Ala
            690                 695                 700

Ala Val Trp Lys Gly Lys Thr Glu Lys Ala Pro Ala Pro Asp Met Pro
705                 710                 715                 720

Ile Gln Arg Gly Pro Pro Leu Pro Pro Ala His Val His Ala Glu Ser
            725                 730                 735
```

```
Asn Ser Ser Thr Ser Ile Trp Leu Arg Trp Lys Lys Pro Asp Phe Thr
                740                 745                 750

Thr Val Lys Ile Val Asn Tyr Thr Val Arg Phe Ser Pro Trp Gly Leu
            755                 760                 765

Arg Asn Ala Ser Leu Val Thr Tyr Tyr Thr Ser Ser Gly Glu Asp Ile
        770                 775                 780

Leu Ile Gly Gly Leu Lys Pro Phe Thr Lys Tyr Glu Phe Ala Val Gln
785                 790                 795                 800

Ser His Gly Val Asp Met Asp Gly Pro Phe Gly Ser Val Val Glu Arg
                805                 810                 815

Ser Thr Leu Pro Asp Arg Pro Ser Thr Pro Ser Asp Leu Arg Leu
            820                 825                 830

Ser Pro Leu Thr Pro Ser Thr Val Arg Leu His Trp Cys Pro Pro Thr
        835                 840                 845

Glu Pro Asn Gly Glu Ile Val Glu Tyr Leu Ile Leu Tyr Ser Ser Asn
850                 855                 860

His Thr Gln Pro Glu His Gln Trp Thr Leu Leu Thr Gln Gly Asn
865                 870                 875                 880

Ile Phe Ser Ala Glu Val His Gly Leu Glu Ser Asp Thr Arg Tyr Phe
            885                 890                 895

Phe Lys Met Gly Ala Arg Thr Glu Val Gly Pro Gly Pro Phe Ser Arg
        900                 905                 910

Leu Gln Asp Val Ile Thr Leu Gln Glu Lys Leu Ser Asp Ser Leu Asp
            915                 920                 925

Met His Ser
        930

<210> SEQ ID NO 7
<211> LENGTH: 402
<212> TYPE: PRT
<213> ORGANISM: Artificial Sequence
<220> FEATURE:
<223> OTHER INFORMATION: Human NOPE ECD (25-426), without signal
      peptide.

<400> SEQUENCE: 7

Glu Leu Leu Leu Pro Gln Glu Thr Thr Val Glu Leu Ser Cys Gly Val
1               5                   10                  15

Gly Pro Leu Gln Val Ile Leu Gly Pro Glu Gln Ala Ala Val Leu Asn
            20                  25                  30

Cys Ser Leu Gly Ala Ala Ala Ala Gly Pro Pro Thr Arg Val Thr Trp
        35                  40                  45

Ser Lys Asp Gly Asp Thr Leu Leu Glu His Asp His Leu His Leu Leu
    50                  55                  60

Pro Asn Gly Ser Leu Trp Leu Ser Gln Pro Leu Ala Pro Asn Gly Ser
65                  70                  75                  80

Asp Glu Ser Val Pro Glu Ala Val Gly Val Ile Glu Gly Asn Tyr Ser
                85                  90                  95

Cys Leu Ala His Gly Pro Leu Gly Val Leu Ala Ser Gln Thr Ala Val
            100                 105                 110

Val Lys Leu Ala Thr Leu Ala Asp Phe Ser Leu His Pro Glu Ser Gln
        115                 120                 125

Thr Val Glu Glu Asn Gly Thr Ala Arg Phe Glu Cys His Ile Glu Gly
    130                 135                 140

Leu Pro Ala Pro Ile Ile Thr Trp Glu Lys Asp Gln Val Thr Leu Pro
```

```
145                 150                 155                 160
Glu Glu Pro Arg Leu Ile Val Leu Pro Asn Gly Val Leu Gln Ile Leu
                165                 170                 175
Asp Val Gln Glu Ser Asp Ala Gly Pro Tyr Arg Cys Val Ala Thr Asn
            180                 185                 190
Ser Ala Arg Gln His Phe Ser Gln Glu Ala Leu Leu Ser Val Ala His
        195                 200                 205
Arg Gly Ser Leu Ala Ser Thr Arg Gly Gln Asp Val Val Ile Val Ala
    210                 215                 220
Ala Pro Glu Asn Thr Thr Val Val Ser Gly Gln Ser Val Val Met Glu
225                 230                 235                 240
Cys Val Ala Ser Ala Asp Pro Thr Pro Phe Val Ser Trp Val Arg Gln
                245                 250                 255
Asp Gly Lys Pro Ile Ser Thr Asp Val Ile Val Leu Gly Arg Thr Asn
            260                 265                 270
Leu Leu Ile Ala Asn Ala Gln Pro Trp His Ser Gly Val Tyr Val Cys
        275                 280                 285
Arg Ala Asn Lys Pro Arg Thr Arg Asp Phe Ala Thr Ala Ala Ala Glu
    290                 295                 300
Leu Arg Val Leu Ala Ala Pro Ala Ile Thr Gln Ala Pro Glu Ala Leu
305                 310                 315                 320
Ser Arg Thr Arg Ala Ser Thr Ala Arg Phe Val Cys Arg Ala Ser Gly
                325                 330                 335
Glu Pro Arg Pro Ala Leu Arg Trp Leu His Asn Gly Ala Pro Leu Arg
            340                 345                 350
Pro Asn Gly Arg Val Lys Val Gln Gly Gly Gly Ser Leu Val Ile
        355                 360                 365
Thr Gln Ile Gly Leu Gln Asp Ala Gly Tyr Tyr Gln Cys Val Ala Glu
    370                 375                 380
Asn Ser Ala Gly Met Ala Cys Ala Ala Ala Ser Leu Ala Val Val Val
385                 390                 395                 400
Arg Glu

<210> SEQ ID NO 8
<211> LENGTH: 596
<212> TYPE: PRT
<213> ORGANISM: Artificial Sequence
<220> FEATURE:
<223> OTHER INFORMATION: Human NOPE ECD (25-620), without signal
      peptide.

<400> SEQUENCE: 8

Glu Leu Leu Pro Gln Glu Thr Thr Val Glu Leu Ser Cys Gly Val
1               5                   10                  15

Gly Pro Leu Gln Val Ile Leu Gly Pro Glu Gln Ala Ala Val Leu Asn
                20                  25                  30

Cys Ser Leu Gly Ala Ala Ala Gly Pro Thr Arg Val Thr Trp
        35                  40                  45

Ser Lys Asp Gly Asp Thr Leu Leu Glu His Asp His Leu His Leu Leu
    50                  55                  60

Pro Asn Gly Ser Leu Trp Leu Ser Gln Pro Leu Ala Pro Asn Gly Ser
65                  70                  75                  80

Asp Glu Ser Val Pro Glu Ala Val Gly Val Ile Glu Gly Asn Tyr Ser
                85                  90                  95

Cys Leu Ala His Gly Pro Leu Gly Val Leu Ala Ser Gln Thr Ala Val
```

```
                100                 105                 110
Val Lys Leu Ala Thr Leu Ala Asp Phe Ser Leu His Pro Glu Ser Gln
            115                 120                 125

Thr Val Glu Glu Asn Gly Thr Ala Arg Phe Glu Cys His Ile Glu Gly
        130                 135                 140

Leu Pro Ala Pro Ile Ile Thr Trp Glu Lys Asp Gln Val Thr Leu Pro
145                 150                 155                 160

Glu Glu Pro Arg Leu Ile Val Leu Pro Asn Gly Val Leu Gln Ile Leu
                165                 170                 175

Asp Val Gln Glu Ser Asp Ala Gly Pro Tyr Arg Cys Val Ala Thr Asn
            180                 185                 190

Ser Ala Arg Gln His Phe Ser Gln Glu Ala Leu Leu Ser Val Ala His
        195                 200                 205

Arg Gly Ser Leu Ala Ser Thr Arg Gly Gln Asp Val Val Ile Val Ala
    210                 215                 220

Ala Pro Glu Asn Thr Thr Val Val Ser Gly Gln Ser Val Val Met Glu
225                 230                 235                 240

Cys Val Ala Ser Ala Asp Pro Thr Pro Phe Val Ser Trp Val Arg Gln
                245                 250                 255

Asp Gly Lys Pro Ile Ser Thr Asp Val Ile Val Leu Gly Arg Thr Asn
            260                 265                 270

Leu Leu Ile Ala Asn Ala Gln Pro Trp His Ser Gly Val Tyr Val Cys
        275                 280                 285

Arg Ala Asn Lys Pro Arg Thr Arg Asp Phe Ala Thr Ala Ala Ala Glu
    290                 295                 300

Leu Arg Val Leu Ala Ala Pro Ala Ile Thr Gln Ala Pro Glu Ala Leu
305                 310                 315                 320

Ser Arg Thr Arg Ala Ser Thr Ala Arg Phe Val Cys Arg Ala Ser Gly
                325                 330                 335

Glu Pro Arg Pro Ala Leu Arg Trp Leu His Asn Gly Ala Pro Leu Arg
            340                 345                 350

Pro Asn Gly Arg Val Lys Val Gln Gly Gly Gly Ser Leu Val Ile
        355                 360                 365

Thr Gln Ile Gly Leu Gln Asp Ala Gly Tyr Tyr Gln Cys Val Ala Glu
    370                 375                 380

Asn Ser Ala Gly Met Ala Cys Ala Ala Ala Ser Leu Ala Val Val Val
385                 390                 395                 400

Arg Glu Gly Leu Pro Ser Ala Pro Thr Arg Val Thr Ala Thr Pro Leu
                405                 410                 415

Ser Ser Ser Ala Val Leu Val Ala Trp Glu Arg Pro Glu Met His Ser
            420                 425                 430

Glu Gln Ile Ile Gly Phe Ser Leu His Tyr Gln Lys Ala Arg Gly Met
        435                 440                 445

Asp Asn Val Glu Tyr Gln Phe Ala Val Asn Asn Asp Thr Thr Glu Leu
    450                 455                 460

Gln Val Arg Asp Leu Glu Pro Asn Thr Asp Tyr Glu Phe Tyr Val Val
465                 470                 475                 480

Ala Tyr Ser Gln Leu Gly Ala Ser Arg Thr Ser Thr Pro Ala Leu Val
                485                 490                 495

His Thr Leu Asp Asp Val Pro Ser Ala Ala Pro Gln Leu Ser Leu Ser
            500                 505                 510

Ser Pro Asn Pro Ser Asp Ile Arg Val Ala Trp Leu Pro Leu Pro Pro
        515                 520                 525
```

```
Ser Leu Ser Asn Gly Gln Val Val Lys Tyr Lys Ile Glu Tyr Gly Leu
        530                 535                 540

Gly Lys Glu Asp Gln Ile Phe Ser Thr Glu Val Arg Gly Asn Glu Thr
545                 550                 555                 560

Gln Leu Met Leu Asn Ser Leu Gln Pro Asn Lys Val Tyr Arg Val Arg
                565                 570                 575

Ile Ser Ala Gly Thr Ala Ala Gly Phe Gly Ala Pro Ser Gln Trp Met
            580                 585                 590

His His Arg Thr
        595

<210> SEQ ID NO 9
<211> LENGTH: 529
<212> TYPE: PRT
<213> ORGANISM: Artificial Sequence
<220> FEATURE:
<223> OTHER INFORMATION: Human NOPE ECD (427-955).

<400> SEQUENCE: 9

Gly Leu Pro Ser Ala Pro Thr Arg Val Thr Ala Thr Pro Leu Ser Ser
1               5                   10                  15

Ser Ala Val Leu Val Ala Trp Glu Arg Pro Glu Met His Ser Glu Gln
            20                  25                  30

Ile Ile Gly Phe Ser Leu His Tyr Gln Lys Ala Arg Gly Met Asp Asn
        35                  40                  45

Val Glu Tyr Gln Phe Ala Val Asn Asn Asp Thr Thr Glu Leu Gln Val
    50                  55                  60

Arg Asp Leu Glu Pro Asn Thr Asp Tyr Glu Phe Tyr Val Val Ala Tyr
65                  70                  75                  80

Ser Gln Leu Gly Ala Ser Arg Thr Ser Thr Pro Ala Leu Val His Thr
                85                  90                  95

Leu Asp Asp Val Pro Ser Ala Ala Pro Gln Leu Ser Leu Ser Ser Pro
            100                 105                 110

Asn Pro Ser Asp Ile Arg Val Ala Trp Leu Pro Leu Pro Pro Ser Leu
        115                 120                 125

Ser Asn Gly Gln Val Val Lys Tyr Lys Ile Glu Tyr Gly Leu Gly Lys
    130                 135                 140

Glu Asp Gln Ile Phe Ser Thr Glu Val Arg Gly Asn Glu Thr Gln Leu
145                 150                 155                 160

Met Leu Asn Ser Leu Gln Pro Asn Lys Val Tyr Arg Val Arg Ile Ser
                165                 170                 175

Ala Gly Thr Ala Ala Gly Phe Gly Ala Pro Ser Gln Trp Met His His
            180                 185                 190

Arg Thr Pro Ser Met His Asn Gln Ser His Val Pro Phe Ala Pro Ala
        195                 200                 205

Glu Leu Lys Val Gln Ala Lys Met Glu Ser Leu Val Val Ser Trp Gln
    210                 215                 220

Pro Pro His Pro Thr Gln Ile Ser Gly Tyr Lys Leu Tyr Trp Arg
225                 230                 235                 240

Glu Val Gly Ala Glu Glu Ala Asn Gly Asp Arg Leu Pro Gly Gly
                245                 250                 255

Arg Gly Asp Gln Ala Trp Asp Val Gly Pro Val Arg Leu Lys Lys Lys
            260                 265                 270

Val Lys Gln Tyr Glu Leu Thr Gln Leu Val Pro Gly Arg Leu Tyr Glu
        275                 280                 285
```

-continued

Val Lys Leu Val Ala Phe Asn Lys His Glu Asp Gly Tyr Ala Ala Val
        290                 295                 300

Trp Lys Gly Lys Thr Glu Lys Ala Pro Ala Pro Asp Met Pro Ile Gln
305                 310                 315                 320

Arg Gly Pro Pro Leu Pro Pro Ala His Val His Ala Glu Ser Asn Ser
                325                 330                 335

Ser Thr Ser Ile Trp Leu Arg Trp Lys Lys Pro Asp Phe Thr Thr Val
            340                 345                 350

Lys Ile Val Asn Tyr Thr Val Arg Phe Ser Pro Trp Gly Leu Arg Asn
        355                 360                 365

Ala Ser Leu Val Thr Tyr Tyr Thr Ser Ser Gly Glu Asp Ile Leu Ile
    370                 375                 380

Gly Gly Leu Lys Pro Phe Thr Lys Tyr Glu Phe Ala Val Gln Ser His
385                 390                 395                 400

Gly Val Asp Met Asp Gly Pro Phe Gly Ser Val Val Glu Arg Ser Thr
                405                 410                 415

Leu Pro Asp Arg Pro Ser Thr Pro Pro Ser Asp Leu Arg Leu Ser Pro
            420                 425                 430

Leu Thr Pro Ser Thr Val Arg Leu His Trp Cys Pro Pro Thr Glu Pro
        435                 440                 445

Asn Gly Glu Ile Val Glu Tyr Leu Ile Leu Tyr Ser Ser Asn His Thr
    450                 455                 460

Gln Pro Glu His Gln Trp Thr Leu Leu Thr Thr Gln Gly Asn Ile Phe
465                 470                 475                 480

Ser Ala Glu Val His Gly Leu Glu Ser Asp Thr Arg Tyr Phe Phe Lys
                485                 490                 495

Met Gly Ala Arg Thr Glu Val Gly Pro Gly Pro Phe Ser Arg Leu Gln
            500                 505                 510

Asp Val Ile Thr Leu Gln Glu Lys Leu Ser Asp Ser Leu Asp Met His
        515                 520                 525

Ser

<210> SEQ ID NO 10
<211> LENGTH: 333
<212> TYPE: PRT
<213> ORGANISM: Artificial Sequence
<220> FEATURE:
<223> OTHER INFORMATION: Human NOPE ECD (623-955).

<400> SEQUENCE: 10

Met His Asn Gln Ser His Val Pro Phe Ala Pro Ala Glu Leu Lys Val
1               5                   10                  15

Gln Ala Lys Met Glu Ser Leu Val Val Ser Trp Gln Pro Pro His
            20                  25                  30

Pro Thr Gln Ile Ser Gly Tyr Lys Leu Tyr Trp Arg Glu Val Gly Ala
        35                  40                  45

Glu Glu Ala Asn Gly Asp Arg Leu Pro Gly Arg Gly Asp Gln
    50                  55                  60

Ala Trp Asp Val Gly Pro Val Arg Leu Lys Lys Val Lys Gln Tyr
65                  70                  75                  80

Glu Leu Thr Gln Leu Val Pro Gly Arg Leu Tyr Glu Val Lys Leu Val
                85                  90                  95

Ala Phe Asn Lys His Glu Asp Gly Tyr Ala Ala Val Trp Lys Gly Lys
            100                 105                 110

```
Thr Glu Lys Ala Pro Ala Pro Asp Met Pro Ile Gln Arg Gly Pro Pro
            115                 120                 125

Leu Pro Pro Ala His Val His Ala Glu Ser Asn Ser Thr Ser Ile
130                 135                 140

Trp Leu Arg Trp Lys Lys Pro Asp Phe Thr Thr Val Lys Ile Val Asn
145                 150                 155                 160

Tyr Thr Val Arg Phe Ser Pro Trp Gly Leu Arg Asn Ala Ser Leu Val
                165                 170                 175

Thr Tyr Tyr Thr Ser Ser Gly Glu Asp Ile Leu Ile Gly Gly Leu Lys
            180                 185                 190

Pro Phe Thr Lys Tyr Glu Phe Ala Val Gln Ser His Gly Val Asp Met
        195                 200                 205

Asp Gly Pro Phe Gly Ser Val Val Glu Arg Ser Thr Leu Pro Asp Arg
    210                 215                 220

Pro Ser Thr Pro Pro Ser Asp Leu Arg Leu Ser Pro Leu Thr Pro Ser
225                 230                 235                 240

Thr Val Arg Leu His Trp Cys Pro Pro Thr Glu Pro Asn Gly Glu Ile
                245                 250                 255

Val Glu Tyr Leu Ile Leu Tyr Ser Ser Asn His Thr Gln Pro Glu His
            260                 265                 270

Gln Trp Thr Leu Leu Thr Thr Gln Gly Asn Ile Phe Ser Ala Glu Val
        275                 280                 285

His Gly Leu Glu Ser Asp Thr Arg Tyr Phe Phe Lys Met Gly Ala Arg
    290                 295                 300

Thr Glu Val Gly Pro Gly Pro Phe Ser Arg Leu Gln Asp Val Ile Thr
305                 310                 315                 320

Leu Gln Glu Lys Leu Ser Asp Ser Leu Asp Met His Ser
                325                 330

<210> SEQ ID NO 11
<211> LENGTH: 956
<212> TYPE: PRT
<213> ORGANISM: Artificial Sequence
<220> FEATURE:
<223> OTHER INFORMATION: Mouse NOPE extracellular domain (ECD) (1-956),
      with signal peptide.

<400> SEQUENCE: 11

Met Ala Arg Ala Asp Thr Gly Arg Gly Leu Leu Val Leu Thr Phe Cys
1               5                   10                  15

Leu Leu Ser Ala Arg Gly Glu Leu Pro Leu Pro Gln Glu Thr Thr Val
            20                  25                  30

Lys Leu Ser Cys Asp Glu Gly Pro Leu Gln Val Ile Leu Gly Pro Glu
        35                  40                  45

Gln Ala Val Val Leu Asp Cys Thr Leu Gly Ala Thr Ala Ala Gly Pro
    50                  55                  60

Pro Thr Arg Val Thr Trp Ser Lys Asp Gly Asp Thr Val Leu Glu His
65                  70                  75                  80

Glu Asn Leu His Leu Leu Pro Asn Gly Ser Leu Trp Leu Ser Pro
                85                  90                  95

Leu Glu Gln Glu Asp Ser Asp Glu Glu Ala Leu Arg Ile Trp Lys
            100                 105                 110

Val Thr Glu Gly Ser Tyr Ser Cys Leu Ala His Ser Pro Leu Gly Val
        115                 120                 125

Val Ala Ser Gln Val Ala Val Val Lys Leu Ala Thr Leu Glu Asp Phe
    130                 135                 140
```

```
Ser Leu His Pro Glu Ser Gln Ile Val Glu Glu Asn Gly Thr Ala Arg
145                 150                 155                 160

Phe Glu Cys His Thr Lys Gly Leu Pro Ala Pro Ile Ile Thr Trp Glu
            165                 170                 175

Lys Asp Gln Val Thr Val Pro Glu Glu Ser Arg Leu Ile Thr Leu Pro
            180                 185                 190

Asn Gly Val Leu Gln Ile Leu Asp Val Gln Asp Ser Asp Ala Gly Ser
            195                 200                 205

Tyr Arg Cys Val Ala Thr Asn Ser Ala Arg Gln Arg Phe Ser Gln Glu
210                 215                 220

Ala Ser Leu Thr Val Ala Leu Arg Gly Ser Leu Glu Ala Thr Arg Gly
225                 230                 235                 240

Gln Asp Val Val Ile Val Ala Ala Pro Glu Asn Thr Thr Val Val Ser
            245                 250                 255

Gly Gln Ser Val Val Met Glu Cys Val Ala Ser Ala Asp Pro Thr Pro
            260                 265                 270

Phe Val Ser Trp Val Arg Gln Asp Gly Lys Pro Ile Ser Thr Asp Val
            275                 280                 285

Ile Val Leu Gly Arg Thr Asn Leu Leu Ile Ala Ser Ala Gln Pro Arg
290                 295                 300

His Ser Gly Val Tyr Val Cys Arg Ala Asn Lys Pro Arg Thr Arg Asp
305                 310                 315                 320

Phe Ala Thr Ala Ala Ala Glu Leu Arg Val Leu Ala Ala Pro Ala Ile
            325                 330                 335

Ser Gln Ala Pro Glu Ala Leu Ser Arg Thr Arg Ala Ser Thr Ala Arg
            340                 345                 350

Phe Val Cys Arg Ala Ser Gly Glu Pro Arg Pro Ala Leu His Trp Leu
            355                 360                 365

His Asp Gly Ile Pro Leu Arg Pro Asn Gly Arg Val Lys Val Gln Gly
370                 375                 380

Gly Gly Gly Ser Leu Val Ile Thr Gln Ile Gly Leu Gln Asp Ala Gly
385                 390                 395                 400

Tyr Tyr Gln Cys Val Ala Glu Asn Ser Ala Gly Thr Ala Cys Ala Ala
            405                 410                 415

Ala Pro Leu Ala Val Val Arg Glu Gly Leu Pro Ser Ala Pro Thr
            420                 425                 430

Arg Val Thr Ala Thr Pro Leu Ser Ser Ser Val Leu Val Ala Trp
            435                 440                 445

Glu Arg Pro Glu Leu His Ser Glu Gln Ile Ile Gly Phe Ser Leu His
450                 455                 460

Tyr Gln Lys Ala Arg Gly Val Asp Asn Val Glu Tyr Gln Phe Ala Val
465                 470                 475                 480

Asn Asn Asp Thr Thr Glu Leu Gln Val Arg Asp Leu Glu Pro Asn Thr
            485                 490                 495

Asp Tyr Glu Phe Tyr Val Val Ala Tyr Ser Gln Leu Gly Ala Ser Arg
            500                 505                 510

Thr Ser Ser Pro Ala Leu Val His Thr Leu Asp Asp Val Pro Ser Ala
            515                 520                 525

Ala Pro Gln Leu Thr Leu Ser Ser Pro Asn Pro Ser Asp Ile Arg Val
            530                 535                 540

Ala Trp Leu Pro Leu Pro Ser Ser Leu Ser Asn Gly Gln Val Leu Lys
545                 550                 555                 560
```

Tyr Lys Ile Glu Tyr Gly Leu Gly Lys Glu Asp Gln Val Phe Ser Thr
            565                 570                 575

Glu Val Pro Gly Asn Glu Thr Gln Leu Thr Leu Asn Ser Leu Gln Pro
        580                 585                 590

Asn Lys Val Tyr Arg Val Arg Ile Ser Ala Gly Thr Gly Ala Gly Tyr
        595                 600                 605

Gly Val Pro Ser Gln Trp Met Gln His Arg Thr Pro Gly Val His Asn
    610                 615                 620

Gln Ser His Val Pro Phe Ala Pro Ala Glu Leu Lys Val Arg Ala Lys
625                 630                 635                 640

Met Glu Ser Leu Val Val Ser Trp Gln Pro Pro His Pro Thr Gln
                645                 650                 655

Ile Ser Gly Tyr Lys Leu Tyr Trp Arg Glu Val Gly Thr Glu Glu Glu
            660                 665                 670

Ala Asp Gly Asp Arg Pro Pro Gly Arg Gly Asp Gln Ala Trp Asp
                675                 680                 685

Val Gly Pro Val Arg Leu Lys Lys Val Lys Gln Tyr Glu Leu Thr
    690                 695                 700

Gln Leu Val Pro Gly Arg Leu Tyr Glu Val Lys Leu Val Ala Phe Asn
705                 710                 715                 720

Lys His Glu Asp Gly Tyr Ala Ala Val Trp Lys Gly Lys Thr Glu Lys
                725                 730                 735

Ala Pro Thr Pro Asp Leu Pro Ile Gln Arg Gly Pro Pro Leu Pro Pro
                740                 745                 750

Ala His Val His Ala Glu Ser Asn Ser Ser Thr Ser Ile Trp Leu Arg
                755                 760                 765

Trp Lys Lys Pro Asp Phe Thr Thr Val Lys Ile Val Asn Tyr Thr Val
    770                 775                 780

Arg Phe Gly Pro Trp Gly Leu Arg Asn Ala Ser Leu Val Thr Tyr Tyr
785                 790                 795                 800

Thr Ser Ser Gly Glu Asp Ile Leu Ile Gly Leu Lys Pro Phe Thr
                805                 810                 815

Lys Tyr Glu Phe Ala Val Gln Ser His Gly Val Asp Met Asp Gly Pro
        820                 825                 830

Phe Gly Ser Val Val Glu Arg Ser Thr Leu Pro Asp Arg Pro Ser Thr
    835                 840                 845

Pro Pro Ser Asp Leu Arg Leu Ser Pro Leu Thr Pro Ser Thr Val Arg
        850                 855                 860

Leu His Trp Cys Pro Pro Thr Glu Pro Asn Gly Glu Ile Val Glu Tyr
865                 870                 875                 880

Leu Ile Leu Tyr Ser Asn Asn His Thr Gln Pro Glu His Gln Trp Thr
                885                 890                 895

Leu Leu Thr Thr Glu Gly Asn Ile Phe Ser Ala Glu Val His Gly Leu
            900                 905                 910

Glu Ser Asp Thr Arg Tyr Phe Phe Lys Met Gly Ala Arg Thr Glu Val
        915                 920                 925

Gly Pro Gly Pro Phe Ser Arg Leu Gln Asp Val Ile Thr Leu Gln Lys
    930                 935                 940

Thr Phe Ser Asp Ser Leu Asp Val His Ala Val Thr
945                 950                 955

<210> SEQ ID NO 12
<211> LENGTH: 934
<212> TYPE: PRT

<213> ORGANISM: Artificial Sequence
<220> FEATURE:
<223> OTHER INFORMATION: Mouse NOPE ECD (23-956), without signal peptide.

<400> SEQUENCE: 12

```
Glu Leu Pro Leu Pro Gln Glu Thr Thr Val Lys Leu Ser Cys Asp Glu
1               5                   10                  15

Gly Pro Leu Gln Val Ile Leu Gly Pro Glu Gln Ala Val Val Leu Asp
            20                  25                  30

Cys Thr Leu Gly Ala Thr Ala Ala Gly Pro Pro Thr Arg Val Thr Trp
        35                  40                  45

Ser Lys Asp Gly Asp Thr Val Leu Glu His Glu Asn Leu His Leu Leu
    50                  55                  60

Pro Asn Gly Ser Leu Trp Leu Ser Ser Pro Leu Glu Gln Glu Asp Ser
65                  70                  75                  80

Asp Asp Glu Glu Ala Leu Arg Ile Trp Lys Val Thr Glu Gly Ser Tyr
                85                  90                  95

Ser Cys Leu Ala His Ser Pro Leu Gly Val Val Ala Ser Gln Val Ala
            100                 105                 110

Val Val Lys Leu Ala Thr Leu Glu Asp Phe Ser Leu His Pro Glu Ser
        115                 120                 125

Gln Ile Val Glu Glu Asn Gly Thr Ala Arg Phe Glu Cys His Thr Lys
    130                 135                 140

Gly Leu Pro Ala Pro Ile Ile Thr Trp Glu Lys Asp Gln Val Thr Val
145                 150                 155                 160

Pro Glu Glu Ser Arg Leu Ile Thr Leu Pro Asn Gly Val Leu Gln Ile
                165                 170                 175

Leu Asp Val Gln Asp Ser Asp Ala Gly Ser Tyr Arg Cys Val Ala Thr
            180                 185                 190

Asn Ser Ala Arg Gln Arg Phe Ser Gln Glu Ala Ser Leu Thr Val Ala
        195                 200                 205

Leu Arg Gly Ser Leu Glu Ala Thr Arg Gly Gln Asp Val Val Ile Val
    210                 215                 220

Ala Ala Pro Glu Asn Thr Thr Val Val Ser Gly Gln Ser Val Val Met
225                 230                 235                 240

Glu Cys Val Ala Ser Ala Asp Pro Thr Pro Phe Val Ser Trp Val Arg
                245                 250                 255

Gln Asp Gly Lys Pro Ile Ser Thr Asp Val Ile Val Leu Gly Arg Thr
            260                 265                 270

Asn Leu Leu Ile Ala Ser Ala Gln Pro Arg His Ser Gly Val Tyr Val
        275                 280                 285

Cys Arg Ala Asn Lys Pro Arg Thr Arg Asp Phe Ala Thr Ala Ala Ala
    290                 295                 300

Glu Leu Arg Val Leu Ala Ala Pro Ala Ile Ser Gln Ala Pro Glu Ala
305                 310                 315                 320

Leu Ser Arg Thr Arg Ala Ser Thr Ala Arg Phe Val Cys Arg Ala Ser
                325                 330                 335

Gly Glu Pro Arg Pro Ala Leu His Trp Leu His Asp Gly Ile Pro Leu
            340                 345                 350

Arg Pro Asn Gly Arg Val Lys Val Gln Gly Gly Gly Ser Leu Val
        355                 360                 365

Ile Thr Gln Ile Gly Leu Gln Asp Ala Gly Tyr Tyr Gln Cys Val Ala
    370                 375                 380
```

```
Glu Asn Ser Ala Gly Thr Ala Cys Ala Ala Ala Pro Leu Ala Val Val
385                 390                 395                 400

Val Arg Glu Gly Leu Pro Ser Ala Pro Thr Arg Val Thr Ala Thr Pro
            405                 410                 415

Leu Ser Ser Ser Val Leu Val Ala Trp Glu Arg Pro Glu Leu His
                420                 425                 430

Ser Glu Gln Ile Ile Gly Phe Ser Leu His Tyr Gln Lys Ala Arg Gly
        435                 440                 445

Val Asp Asn Val Glu Tyr Gln Phe Ala Val Asn Asp Thr Thr Glu
    450                 455                 460

Leu Gln Val Arg Asp Leu Glu Pro Asn Thr Asp Tyr Glu Phe Tyr Val
465                 470                 475                 480

Val Ala Tyr Ser Gln Leu Gly Ala Ser Arg Thr Ser Pro Ala Leu
                485                 490                 495

Val His Thr Leu Asp Asp Val Pro Ser Ala Ala Pro Gln Leu Thr Leu
                500                 505                 510

Ser Ser Pro Asn Pro Ser Asp Ile Arg Val Ala Trp Leu Pro Leu Pro
        515                 520                 525

Ser Ser Leu Ser Asn Gly Gln Val Leu Lys Tyr Lys Ile Glu Tyr Gly
530                 535                 540

Leu Gly Lys Glu Asp Gln Val Phe Ser Thr Glu Val Pro Gly Asn Glu
545                 550                 555                 560

Thr Gln Leu Thr Leu Asn Ser Leu Gln Pro Asn Lys Val Tyr Arg Val
                565                 570                 575

Arg Ile Ser Ala Gly Thr Gly Ala Gly Tyr Gly Val Pro Ser Gln Trp
            580                 585                 590

Met Gln His Arg Thr Pro Gly Val His Asn Gln Ser His Val Pro Phe
        595                 600                 605

Ala Pro Ala Glu Leu Lys Val Arg Ala Lys Met Glu Ser Leu Val Val
    610                 615                 620

Ser Trp Gln Pro Pro His Pro Thr Gln Ile Ser Gly Tyr Lys Leu
625                 630                 635                 640

Tyr Trp Arg Glu Val Gly Thr Glu Glu Ala Asp Gly Asp Arg Pro
                645                 650                 655

Pro Gly Gly Arg Gly Asp Gln Ala Trp Asp Val Gly Pro Val Arg Leu
            660                 665                 670

Lys Lys Lys Val Lys Gln Tyr Glu Leu Thr Gln Leu Val Pro Gly Arg
        675                 680                 685

Leu Tyr Glu Val Lys Leu Val Ala Phe Asn Lys His Glu Asp Gly Tyr
    690                 695                 700

Ala Ala Val Trp Lys Gly Lys Thr Glu Lys Ala Pro Thr Pro Asp Leu
705                 710                 715                 720

Pro Ile Gln Arg Gly Pro Pro Leu Pro Pro Ala His Val His Ala Glu
                725                 730                 735

Ser Asn Ser Ser Thr Ser Ile Trp Leu Arg Trp Lys Lys Pro Asp Phe
                740                 745                 750

Thr Thr Val Lys Ile Val Asn Tyr Thr Val Arg Phe Gly Pro Trp Gly
            755                 760                 765

Leu Arg Asn Ala Ser Leu Val Thr Tyr Tyr Thr Ser Ser Gly Glu Asp
        770                 775                 780

Ile Leu Ile Gly Gly Leu Lys Pro Phe Thr Lys Tyr Glu Phe Ala Val
785                 790                 795                 800

Gln Ser His Gly Val Asp Met Asp Gly Pro Phe Gly Ser Val Val Glu
```

```
                    805                 810                 815
Arg Ser Thr Leu Pro Asp Arg Pro Ser Thr Pro Pro Ser Asp Leu Arg
            820                 825                 830

Leu Ser Pro Leu Thr Pro Ser Thr Val Arg Leu His Trp Cys Pro Pro
            835                 840                 845

Thr Glu Pro Asn Gly Glu Ile Val Glu Tyr Leu Ile Leu Tyr Ser Asn
            850                 855                 860

Asn His Thr Gln Pro Glu His Gln Trp Thr Leu Leu Thr Thr Glu Gly
865                 870                 875                 880

Asn Ile Phe Ser Ala Glu Val His Gly Leu Glu Ser Asp Thr Arg Tyr
                885                 890                 895

Phe Phe Lys Met Gly Ala Arg Thr Glu Val Gly Pro Gly Pro Phe Ser
                900                 905                 910

Arg Leu Gln Asp Val Ile Thr Leu Gln Lys Thr Phe Ser Asp Ser Leu
            915                 920                 925

Asp Val His Ala Val Thr
            930

<210> SEQ ID NO 13
<211> LENGTH: 597
<212> TYPE: PRT
<213> ORGANISM: Artificial Sequence
<220> FEATURE:
<223> OTHER INFORMATION: Mouse NOPE ECD (23-619), without signal
      peptide.

<400> SEQUENCE: 13

Glu Leu Pro Leu Pro Gln Glu Thr Thr Val Lys Leu Ser Cys Asp Glu
1               5                   10                  15

Gly Pro Leu Gln Val Ile Leu Gly Pro Glu Gln Ala Val Val Leu Asp
            20                  25                  30

Cys Thr Leu Gly Ala Thr Ala Ala Gly Pro Pro Thr Arg Val Thr Trp
        35                  40                  45

Ser Lys Asp Gly Asp Thr Val Leu Glu His Glu Asn Leu His Leu Leu
    50                  55                  60

Pro Asn Gly Ser Leu Trp Leu Ser Pro Leu Glu Gln Glu Asp Ser
65                  70                  75                  80

Asp Asp Glu Glu Ala Leu Arg Ile Trp Lys Val Thr Glu Gly Ser Tyr
                85                  90                  95

Ser Cys Leu Ala His Ser Pro Leu Gly Val Val Ala Ser Gln Val Ala
            100                 105                 110

Val Val Lys Leu Ala Thr Leu Glu Asp Phe Ser Leu His Pro Glu Ser
        115                 120                 125

Gln Ile Val Glu Glu Asn Gly Thr Ala Arg Phe Glu Cys His Thr Lys
    130                 135                 140

Gly Leu Pro Ala Pro Ile Ile Thr Trp Glu Lys Asp Gln Val Thr Val
145                 150                 155                 160

Pro Glu Glu Ser Arg Leu Ile Thr Leu Pro Asn Gly Val Leu Gln Ile
                165                 170                 175

Leu Asp Val Gln Asp Ser Asp Ala Gly Ser Tyr Arg Cys Val Ala Thr
            180                 185                 190

Asn Ser Ala Arg Gln Arg Phe Ser Gln Glu Ala Ser Leu Thr Val Ala
        195                 200                 205

Leu Arg Gly Ser Leu Glu Ala Thr Arg Gly Gln Asp Val Val Ile Val
    210                 215                 220
```

Ala Ala Pro Glu Asn Thr Thr Val Val Ser Gly Gln Ser Val Val Met
225                 230                 235                 240

Glu Cys Val Ala Ser Ala Asp Pro Thr Pro Phe Val Ser Trp Val Arg
            245                 250                 255

Gln Asp Gly Lys Pro Ile Ser Thr Asp Val Ile Val Leu Gly Arg Thr
            260                 265                 270

Asn Leu Leu Ile Ala Ser Ala Gln Pro Arg His Ser Gly Val Tyr Val
        275                 280                 285

Cys Arg Ala Asn Lys Pro Arg Thr Arg Asp Phe Ala Thr Ala Ala Ala
290                 295                 300

Glu Leu Arg Val Leu Ala Ala Pro Ala Ile Ser Gln Ala Pro Glu Ala
305                 310                 315                 320

Leu Ser Arg Thr Arg Ala Ser Thr Ala Arg Phe Val Cys Arg Ala Ser
                325                 330                 335

Gly Glu Pro Arg Pro Ala Leu His Trp Leu His Asp Gly Ile Pro Leu
                340                 345                 350

Arg Pro Asn Gly Arg Val Lys Val Gln Gly Gly Gly Ser Leu Val
            355                 360                 365

Ile Thr Gln Ile Gly Leu Gln Asp Ala Gly Tyr Tyr Gln Cys Val Ala
370                 375                 380

Glu Asn Ser Ala Gly Thr Ala Cys Ala Ala Ala Pro Leu Ala Val Val
385                 390                 395                 400

Val Arg Glu Gly Leu Pro Ser Ala Pro Thr Arg Val Thr Ala Thr Pro
                405                 410                 415

Leu Ser Ser Ser Ser Val Leu Val Ala Trp Glu Arg Pro Glu Leu His
            420                 425                 430

Ser Glu Gln Ile Ile Gly Phe Ser Leu His Tyr Gln Lys Ala Arg Gly
            435                 440                 445

Val Asp Asn Val Glu Tyr Gln Phe Ala Val Asn Asn Asp Thr Thr Glu
450                 455                 460

Leu Gln Val Arg Asp Leu Glu Pro Asn Thr Asp Tyr Glu Phe Tyr Val
465                 470                 475                 480

Val Ala Tyr Ser Gln Leu Gly Ala Ser Arg Thr Ser Ser Pro Ala Leu
                485                 490                 495

Val His Thr Leu Asp Asp Val Pro Ser Ala Ala Pro Gln Leu Thr Leu
            500                 505                 510

Ser Ser Pro Asn Pro Ser Asp Ile Arg Val Ala Trp Leu Pro Leu Pro
            515                 520                 525

Ser Ser Leu Ser Asn Gly Gln Val Leu Lys Tyr Lys Ile Glu Tyr Gly
            530                 535                 540

Leu Gly Lys Glu Asp Gln Val Phe Ser Thr Glu Val Pro Gly Asn Glu
545                 550                 555                 560

Thr Gln Leu Thr Leu Asn Ser Leu Gln Pro Asn Lys Val Tyr Arg Val
                565                 570                 575

Arg Ile Ser Ala Gly Thr Gly Ala Gly Tyr Gly Val Pro Ser Gln Trp
            580                 585                 590

Met Gln His Arg Thr
        595

<210> SEQ ID NO 14
<211> LENGTH: 334
<212> TYPE: PRT
<213> ORGANISM: Artificial Sequence
<220> FEATURE:
<223> OTHER INFORMATION: Mouse NOPE ECD (623-956), without signal peptide.

<400> SEQUENCE: 14

His Asn Gln Ser His Val Pro Phe Ala Pro Ala Glu Leu Lys Val Arg
1               5                   10                  15

Ala Lys Met Glu Ser Leu Val Val Ser Trp Gln Pro Pro His Pro
            20                  25                  30

Thr Gln Ile Ser Gly Tyr Lys Leu Tyr Trp Arg Glu Val Gly Thr Glu
            35                  40                  45

Glu Glu Ala Asp Gly Asp Arg Pro Pro Gly Gly Arg Gly Asp Gln Ala
        50                  55                  60

Trp Asp Val Gly Pro Val Arg Leu Lys Lys Val Lys Gln Tyr Glu
65                  70                  75                  80

Leu Thr Gln Leu Val Pro Gly Arg Leu Tyr Glu Val Lys Leu Val Ala
                85                  90                  95

Phe Asn Lys His Glu Asp Gly Tyr Ala Ala Val Trp Lys Gly Lys Thr
            100                 105                 110

Glu Lys Ala Pro Thr Pro Asp Leu Pro Ile Gln Arg Gly Pro Pro Leu
        115                 120                 125

Pro Pro Ala His Val His Ala Glu Ser Asn Ser Thr Ser Ile Trp
130                 135                 140

Leu Arg Trp Lys Lys Pro Asp Phe Thr Thr Val Lys Ile Val Asn Tyr
145                 150                 155                 160

Thr Val Arg Phe Gly Pro Trp Gly Leu Arg Asn Ala Ser Leu Val Thr
                165                 170                 175

Tyr Tyr Thr Ser Ser Gly Glu Asp Ile Leu Ile Gly Gly Leu Lys Pro
            180                 185                 190

Phe Thr Lys Tyr Glu Phe Ala Val Gln Ser His Gly Val Asp Met Asp
        195                 200                 205

Gly Pro Phe Gly Ser Val Val Glu Arg Ser Thr Leu Pro Asp Arg Pro
210                 215                 220

Ser Thr Pro Pro Ser Asp Leu Arg Leu Ser Pro Leu Thr Pro Ser Thr
225                 230                 235                 240

Val Arg Leu His Trp Cys Pro Pro Thr Glu Pro Asn Gly Glu Ile Val
                245                 250                 255

Glu Tyr Leu Ile Leu Tyr Ser Asn Asn His Thr Gln Pro Glu His Gln
            260                 265                 270

Trp Thr Leu Leu Thr Thr Glu Gly Asn Ile Phe Ser Ala Glu Val His
        275                 280                 285

Gly Leu Glu Ser Asp Thr Arg Tyr Phe Phe Lys Met Gly Ala Arg Thr
290                 295                 300

Glu Val Gly Pro Gly Pro Phe Ser Arg Leu Gln Asp Val Ile Thr Leu
305                 310                 315                 320

Gln Lys Thr Phe Ser Asp Ser Leu Asp Val His Ala Val Thr
                325                 330

<210> SEQ ID NO 15
<211> LENGTH: 1165
<212> TYPE: PRT
<213> ORGANISM: Artificial Sequence
<220> FEATURE:
<223> OTHER INFORMATION: Human NOPE ECD (25-955)-Fc fusion molecule,
      without signal peptide.

<400> SEQUENCE: 15

Glu Leu Leu Leu Pro Gln Glu Thr Thr Val Glu Leu Ser Cys Gly Val

-continued

```
1               5                   10                  15
Gly Pro Leu Gln Val Ile Leu Gly Pro Glu Gln Ala Ala Val Leu Asn
                20                  25                  30
Cys Ser Leu Gly Ala Ala Ala Gly Pro Pro Thr Arg Val Thr Trp
                35                  40                  45
Ser Lys Asp Gly Asp Thr Leu Leu Glu His Asp His Leu His Leu Leu
                50                  55                  60
Pro Asn Gly Ser Leu Trp Leu Ser Gln Pro Leu Ala Pro Asn Gly Ser
65                  70                  75                  80
Asp Glu Ser Val Pro Glu Ala Val Gly Ile Glu Gly Asn Tyr Ser
                85                  90                  95
Cys Leu Ala His Gly Pro Leu Gly Val Leu Ala Ser Gln Thr Ala Val
                100                 105                 110
Val Lys Leu Ala Thr Leu Ala Asp Phe Ser Leu His Pro Glu Ser Gln
                115                 120                 125
Thr Val Glu Glu Asn Gly Thr Ala Arg Phe Glu Cys His Ile Glu Gly
                130                 135                 140
Leu Pro Ala Pro Ile Ile Thr Trp Glu Lys Asp Gln Val Thr Leu Pro
145                 150                 155                 160
Glu Glu Pro Arg Leu Ile Val Leu Pro Asn Gly Val Leu Gln Ile Leu
                165                 170                 175
Asp Val Gln Glu Ser Asp Ala Gly Pro Tyr Arg Cys Val Ala Thr Asn
                180                 185                 190
Ser Ala Arg Gln His Phe Ser Gln Glu Ala Leu Leu Ser Val Ala His
                195                 200                 205
Arg Gly Ser Leu Ala Ser Thr Arg Gly Gln Asp Val Val Ile Val Ala
                210                 215                 220
Ala Pro Glu Asn Thr Thr Val Val Ser Gly Gln Ser Val Val Met Glu
225                 230                 235                 240
Cys Val Ala Ser Ala Asp Pro Thr Pro Phe Val Ser Trp Val Arg Gln
                245                 250                 255
Asp Gly Lys Pro Ile Ser Thr Asp Val Ile Val Leu Gly Arg Thr Asn
                260                 265                 270
Leu Leu Ile Ala Asn Ala Gln Pro Trp His Ser Gly Val Tyr Val Cys
                275                 280                 285
Arg Ala Asn Lys Pro Arg Thr Arg Asp Phe Ala Thr Ala Ala Ala Glu
                290                 295                 300
Leu Arg Val Leu Ala Ala Pro Ala Ile Thr Gln Ala Pro Glu Ala Leu
305                 310                 315                 320
Ser Arg Thr Arg Ala Ser Thr Ala Arg Phe Val Cys Arg Ala Ser Gly
                325                 330                 335
Glu Pro Arg Pro Ala Leu Arg Trp Leu His Asn Gly Ala Pro Leu Arg
                340                 345                 350
Pro Asn Gly Arg Val Lys Val Gln Gly Gly Gly Ser Leu Val Ile
                355                 360                 365
Thr Gln Ile Gly Leu Gln Asp Ala Gly Tyr Tyr Gln Cys Val Ala Glu
                370                 375                 380
Asn Ser Ala Gly Met Ala Cys Ala Ala Ala Ser Leu Ala Val Val Val
385                 390                 395                 400
Arg Glu Gly Leu Pro Ser Ala Pro Thr Arg Val Thr Ala Thr Pro Leu
                405                 410                 415
Ser Ser Ser Ala Val Leu Val Ala Trp Glu Arg Pro Glu Met His Ser
                420                 425                 430
```

```
Glu Gln Ile Ile Gly Phe Ser Leu His Tyr Gln Lys Ala Arg Gly Met
        435                 440                 445

Asp Asn Val Glu Tyr Gln Phe Ala Val Asn Asn Asp Thr Thr Glu Leu
        450                 455                 460

Gln Val Arg Asp Leu Glu Pro Asn Thr Asp Tyr Glu Phe Tyr Val Val
465                 470                 475                 480

Ala Tyr Ser Gln Leu Gly Ala Ser Arg Thr Ser Thr Pro Ala Leu Val
                    485                 490                 495

His Thr Leu Asp Asp Val Pro Ser Ala Ala Pro Gln Leu Ser Leu Ser
                500                 505                 510

Ser Pro Asn Pro Ser Asp Ile Arg Val Ala Trp Leu Pro Leu Pro Pro
            515                 520                 525

Ser Leu Ser Asn Gly Gln Val Val Lys Tyr Lys Ile Glu Tyr Gly Leu
        530                 535                 540

Gly Lys Glu Asp Gln Ile Phe Ser Thr Glu Val Arg Gly Asn Glu Thr
545                 550                 555                 560

Gln Leu Met Leu Asn Ser Leu Gln Pro Asn Lys Val Tyr Arg Val Arg
                    565                 570                 575

Ile Ser Ala Gly Thr Ala Ala Gly Phe Gly Ala Pro Ser Gln Trp Met
                580                 585                 590

His His Arg Thr Pro Ser Met His Asn Gln Ser His Val Pro Phe Ala
            595                 600                 605

Pro Ala Glu Leu Lys Val Gln Ala Lys Met Glu Ser Leu Val Val Ser
        610                 615                 620

Trp Gln Pro Pro Pro His Pro Thr Gln Ile Ser Gly Tyr Lys Leu Tyr
625                 630                 635                 640

Trp Arg Glu Val Gly Ala Glu Glu Ala Asn Gly Asp Arg Leu Pro
                    645                 650                 655

Gly Gly Arg Gly Asp Gln Ala Trp Asp Val Gly Pro Val Arg Leu Lys
                660                 665                 670

Lys Lys Val Lys Gln Tyr Glu Leu Thr Gln Leu Val Pro Gly Arg Leu
            675                 680                 685

Tyr Glu Val Lys Leu Val Ala Phe Asn Lys His Glu Asp Gly Tyr Ala
        690                 695                 700

Ala Val Trp Lys Gly Lys Thr Glu Lys Ala Pro Ala Pro Asp Met Pro
705                 710                 715                 720

Ile Gln Arg Gly Pro Pro Leu Pro Pro Ala His Val His Ala Glu Ser
                    725                 730                 735

Asn Ser Ser Thr Ser Ile Trp Leu Arg Trp Lys Lys Pro Asp Phe Thr
                740                 745                 750

Thr Val Lys Ile Val Asn Tyr Thr Val Arg Phe Ser Pro Trp Gly Leu
            755                 760                 765

Arg Asn Ala Ser Leu Val Thr Tyr Tyr Thr Ser Ser Gly Glu Asp Ile
        770                 775                 780

Leu Ile Gly Gly Leu Lys Pro Phe Thr Lys Tyr Glu Phe Ala Val Gln
785                 790                 795                 800

Ser His Gly Val Asp Met Asp Gly Pro Phe Gly Ser Val Val Glu Arg
                    805                 810                 815

Ser Thr Leu Pro Asp Arg Pro Ser Thr Pro Pro Ser Asp Leu Arg Leu
                820                 825                 830

Ser Pro Leu Thr Pro Ser Thr Val Arg Leu His Trp Cys Pro Pro Thr
            835                 840                 845
```

Glu Pro Asn Gly Glu Ile Val Glu Tyr Leu Ile Leu Tyr Ser Ser Asn
850                 855                 860

His Thr Gln Pro Glu His Gln Trp Thr Leu Leu Thr Thr Gln Gly Asn
865                 870                 875                 880

Ile Phe Ser Ala Glu Val His Gly Leu Glu Ser Asp Thr Arg Tyr Phe
                885                 890                 895

Phe Lys Met Gly Ala Arg Thr Glu Val Gly Pro Gly Pro Phe Ser Arg
            900                 905                 910

Leu Gln Asp Val Ile Thr Leu Gln Glu Lys Leu Ser Asp Ser Leu Asp
        915                 920                 925

Met His Ser Gly Ser Glu Pro Lys Ser Ser Asp Lys Thr His Thr Cys
930                 935                 940

Pro Pro Cys Pro Ala Pro Glu Leu Leu Gly Gly Pro Ser Val Phe Leu
945                 950                 955                 960

Phe Pro Pro Lys Pro Lys Asp Thr Leu Met Ile Ser Arg Thr Pro Glu
                965                 970                 975

Val Thr Cys Val Val Val Asp Val Ser His Glu Asp Pro Glu Val Lys
            980                 985                 990

Phe Asn Trp Tyr Val Asp Gly Val Glu Val His Asn Ala Lys Thr Lys
        995                 1000                1005

Pro Arg Glu Glu Gln Tyr Asn Ser Thr Tyr Arg Val Val Ser Val Leu
    1010                1015                1020

Thr Val Leu His Gln Asp Trp Leu Asn Gly Lys Glu Tyr Lys Cys Lys
1025                1030                1035                1040

Val Ser Asn Lys Ala Leu Pro Ala Pro Ile Glu Lys Thr Ile Ser Lys
                1045                1050                1055

Ala Lys Gly Gln Pro Arg Glu Pro Gln Val Tyr Thr Leu Pro Pro Ser
            1060                1065                1070

Arg Asp Glu Leu Thr Lys Asn Gln Val Ser Leu Thr Cys Leu Val Lys
        1075                1080                1085

Gly Phe Tyr Pro Ser Asp Ile Ala Val Glu Trp Glu Ser Asn Gly Gln
    1090                1095                1100

Pro Glu Asn Asn Tyr Lys Thr Thr Pro Pro Val Leu Asp Ser Asp Gly
1105                1110                1115                1120

Ser Phe Phe Leu Tyr Ser Lys Leu Thr Val Asp Lys Ser Arg Trp Gln
                1125                1130                1135

Gln Gly Asn Val Phe Ser Cys Ser Val Met His Glu Ala Leu His Asn
            1140                1145                1150

His Tyr Thr Gln Lys Ser Leu Ser Leu Ser Pro Gly Lys
        1155                1160                1165

<210> SEQ ID NO 16
<211> LENGTH: 636
<212> TYPE: PRT
<213> ORGANISM: Artificial Sequence
<220> FEATURE:
<223> OTHER INFORMATION: Human NOPE ECD (25-426)-Fc fusion molecule,
      without signal peptide.

<400> SEQUENCE: 16

Glu Leu Leu Pro Gln Glu Thr Val Glu Leu Ser Cys Gly Val
1               5                   10                  15

Gly Pro Leu Gln Val Ile Leu Gly Pro Glu Gln Ala Ala Val Leu Asn
            20                  25                  30

Cys Ser Leu Gly Ala Ala Ala Ala Gly Pro Pro Thr Arg Val Thr Trp
        35                  40                  45

```
Ser Lys Asp Gly Asp Thr Leu Leu Glu His Asp His Leu His Leu Leu
     50                  55                  60

Pro Asn Gly Ser Leu Trp Leu Ser Gln Pro Leu Ala Pro Asn Gly Ser
 65                  70                  75                  80

Asp Glu Ser Val Pro Glu Ala Val Gly Val Ile Glu Gly Asn Tyr Ser
                 85                  90                  95

Cys Leu Ala His Gly Pro Leu Gly Val Leu Ala Ser Gln Thr Ala Val
             100                 105                 110

Val Lys Leu Ala Thr Leu Ala Asp Phe Ser Leu His Pro Glu Ser Gln
         115                 120                 125

Thr Val Glu Glu Asn Gly Thr Ala Arg Phe Glu Cys His Ile Glu Gly
     130                 135                 140

Leu Pro Ala Pro Ile Ile Thr Trp Glu Lys Asp Gln Val Thr Leu Pro
145                 150                 155                 160

Glu Glu Pro Arg Leu Ile Val Leu Pro Asn Gly Val Leu Gln Ile Leu
                 165                 170                 175

Asp Val Gln Glu Ser Asp Ala Gly Pro Tyr Arg Cys Val Ala Thr Asn
             180                 185                 190

Ser Ala Arg Gln His Phe Ser Gln Glu Ala Leu Leu Ser Val Ala His
         195                 200                 205

Arg Gly Ser Leu Ala Ser Thr Arg Gly Gln Asp Val Val Ile Val Ala
     210                 215                 220

Ala Pro Glu Asn Thr Thr Val Val Ser Gly Gln Ser Val Val Met Glu
225                 230                 235                 240

Cys Val Ala Ser Ala Asp Pro Thr Pro Phe Val Ser Trp Val Arg Gln
                 245                 250                 255

Asp Gly Lys Pro Ile Ser Thr Asp Val Ile Val Leu Gly Arg Thr Asn
             260                 265                 270

Leu Leu Ile Ala Asn Ala Gln Pro Trp His Ser Gly Val Tyr Val Cys
         275                 280                 285

Arg Ala Asn Lys Pro Arg Thr Arg Asp Phe Ala Thr Ala Ala Ala Glu
     290                 295                 300

Leu Arg Val Leu Ala Ala Pro Ala Ile Thr Gln Ala Pro Glu Ala Leu
305                 310                 315                 320

Ser Arg Thr Arg Ala Ser Thr Ala Arg Phe Val Cys Arg Ala Ser Gly
                 325                 330                 335

Glu Pro Arg Pro Ala Leu Arg Trp Leu His Asn Gly Ala Pro Leu Arg
             340                 345                 350

Pro Asn Gly Arg Val Lys Val Gln Gly Gly Gly Ser Leu Val Ile
         355                 360                 365

Thr Gln Ile Gly Leu Gln Asp Ala Gly Tyr Tyr Gln Cys Val Ala Glu
     370                 375                 380

Asn Ser Ala Gly Met Ala Cys Ala Ala Ala Ser Leu Ala Val Val Val
385                 390                 395                 400

Arg Glu Gly Ser Glu Pro Lys Ser Ser Asp Lys Thr His Thr Cys Pro
                 405                 410                 415

Pro Cys Pro Ala Pro Glu Leu Leu Gly Gly Pro Ser Val Phe Leu Phe
             420                 425                 430

Pro Pro Lys Pro Lys Asp Thr Leu Met Ile Ser Arg Thr Pro Glu Val
         435                 440                 445

Thr Cys Val Val Val Asp Val Ser His Glu Asp Pro Glu Val Lys Phe
450                 455                 460
```

```
Asn Trp Tyr Val Asp Gly Val Glu Val His Asn Ala Lys Thr Lys Pro
465                 470                 475                 480

Arg Glu Glu Gln Tyr Asn Ser Thr Tyr Arg Val Val Ser Val Leu Thr
                485                 490                 495

Val Leu His Gln Asp Trp Leu Asn Gly Lys Glu Tyr Lys Cys Lys Val
            500                 505                 510

Ser Asn Lys Ala Leu Pro Ala Pro Ile Glu Lys Thr Ile Ser Lys Ala
        515                 520                 525

Lys Gly Gln Pro Arg Glu Pro Gln Val Tyr Thr Leu Pro Pro Ser Arg
530                 535                 540

Asp Glu Leu Thr Lys Asn Gln Val Ser Leu Thr Cys Leu Val Lys Gly
545                 550                 555                 560

Phe Tyr Pro Ser Asp Ile Ala Val Glu Trp Glu Ser Asn Gly Gln Pro
                565                 570                 575

Glu Asn Asn Tyr Lys Thr Thr Pro Pro Val Leu Asp Ser Asp Gly Ser
                580                 585                 590

Phe Phe Leu Tyr Ser Lys Leu Thr Val Asp Lys Ser Arg Trp Gln Gln
            595                 600                 605

Gly Asn Val Phe Ser Cys Ser Val Met His Glu Ala Leu His Asn His
        610                 615                 620

Tyr Thr Gln Lys Ser Leu Ser Leu Ser Pro Gly Lys
625                 630                 635

<210> SEQ ID NO 17
<211> LENGTH: 830
<212> TYPE: PRT
<213> ORGANISM: Artificial Sequence
<220> FEATURE:
<223> OTHER INFORMATION: Human NOPE ECD (25-620)-Fc fusion molecule,
      without signal peptide.

<400> SEQUENCE: 17

Glu Leu Leu Pro Gln Glu Thr Thr Val Glu Leu Ser Cys Gly Val
1               5                   10                  15

Gly Pro Leu Gln Val Ile Leu Gly Pro Glu Gln Ala Ala Val Leu Asn
                20                  25                  30

Cys Ser Leu Gly Ala Ala Ala Gly Pro Pro Thr Arg Val Thr Trp
            35                  40                  45

Ser Lys Asp Gly Asp Thr Leu Leu Glu His Asp His Leu His Leu Leu
        50                  55                  60

Pro Asn Gly Ser Leu Trp Leu Ser Gln Pro Leu Ala Pro Asn Gly Ser
65                  70                  75                  80

Asp Glu Ser Val Pro Glu Ala Val Gly Val Ile Glu Gly Asn Tyr Ser
                85                  90                  95

Cys Leu Ala His Gly Pro Leu Gly Val Leu Ala Ser Gln Thr Ala Val
            100                 105                 110

Val Lys Leu Ala Thr Leu Ala Asp Phe Ser Leu His Pro Glu Ser Gln
        115                 120                 125

Thr Val Glu Glu Asn Gly Thr Ala Arg Phe Glu Cys His Ile Glu Gly
    130                 135                 140

Leu Pro Ala Pro Ile Ile Thr Trp Glu Lys Asp Gln Val Thr Leu Pro
145                 150                 155                 160

Glu Glu Pro Arg Leu Ile Val Leu Pro Asn Gly Val Leu Gln Ile Leu
                165                 170                 175

Asp Val Gln Glu Ser Asp Ala Gly Pro Tyr Arg Cys Val Ala Thr Asn
            180                 185                 190
```

```
Ser Ala Arg Gln His Phe Ser Gln Glu Ala Leu Leu Ser Val Ala His
        195                 200                 205

Arg Gly Ser Leu Ala Ser Thr Arg Gly Gln Asp Val Ile Val Ala
        210                 215                 220

Ala Pro Glu Asn Thr Thr Val Val Ser Gly Gln Ser Val Met Glu
225                 230                 235                 240

Cys Val Ala Ser Ala Asp Pro Thr Pro Phe Val Ser Trp Val Arg Gln
                245                 250                 255

Asp Gly Lys Pro Ile Ser Thr Asp Val Ile Val Leu Gly Arg Thr Asn
                260                 265                 270

Leu Leu Ile Ala Asn Ala Gln Pro Trp His Ser Gly Val Tyr Val Cys
            275                 280                 285

Arg Ala Asn Lys Pro Arg Thr Arg Asp Phe Ala Thr Ala Ala Glu
        290                 295                 300

Leu Arg Val Leu Ala Ala Pro Ala Ile Thr Gln Ala Pro Glu Ala Leu
305                 310                 315                 320

Ser Arg Thr Arg Ala Ser Thr Ala Arg Phe Val Cys Arg Ala Ser Gly
                325                 330                 335

Glu Pro Arg Pro Ala Leu Arg Trp Leu His Asn Gly Ala Pro Leu Arg
                340                 345                 350

Pro Asn Gly Arg Val Lys Val Gln Gly Gly Gly Ser Leu Val Ile
        355                 360                 365

Thr Gln Ile Gly Leu Gln Asp Ala Gly Tyr Tyr Gln Cys Val Ala Glu
        370                 375                 380

Asn Ser Ala Gly Met Ala Cys Ala Ala Ala Ser Leu Ala Val Val Val
385                 390                 395                 400

Arg Glu Gly Leu Pro Ser Ala Pro Thr Arg Val Thr Ala Thr Pro Leu
                405                 410                 415

Ser Ser Ser Ala Val Leu Val Ala Trp Glu Arg Pro Glu Met His Ser
                420                 425                 430

Glu Gln Ile Ile Gly Phe Ser Leu His Tyr Gln Lys Ala Arg Gly Met
        435                 440                 445

Asp Asn Val Glu Tyr Gln Phe Ala Val Asn Asn Asp Thr Thr Glu Leu
        450                 455                 460

Gln Val Arg Asp Leu Glu Pro Asn Thr Asp Tyr Glu Phe Tyr Val Val
465                 470                 475                 480

Ala Tyr Ser Gln Leu Gly Ala Ser Arg Thr Ser Thr Pro Ala Leu Val
                485                 490                 495

His Thr Leu Asp Asp Val Pro Ser Ala Pro Gln Leu Ser Leu Ser
                500                 505                 510

Ser Pro Asn Pro Ser Asp Ile Arg Val Ala Trp Leu Pro Leu Pro Pro
            515                 520                 525

Ser Leu Ser Asn Gly Gln Val Val Lys Tyr Lys Ile Glu Tyr Gly Leu
            530                 535                 540

Gly Lys Glu Asp Gln Ile Phe Ser Thr Glu Val Arg Gly Asn Glu Thr
545                 550                 555                 560

Gln Leu Met Leu Asn Ser Leu Gln Pro Asn Lys Val Tyr Arg Val Arg
                565                 570                 575

Ile Ser Ala Gly Thr Ala Ala Gly Phe Gly Ala Pro Ser Gln Trp Met
                580                 585                 590

His His Arg Thr Gly Ser Glu Pro Lys Ser Ser Asp Lys Thr His Thr
            595                 600                 605
```

```
Cys Pro Pro Cys Pro Ala Pro Glu Leu Leu Gly Gly Pro Ser Val Phe
    610                 615                 620

Leu Phe Pro Pro Lys Pro Lys Asp Thr Leu Met Ile Ser Arg Thr Pro
625                 630                 635                 640

Glu Val Thr Cys Val Val Val Asp Val Ser His Glu Asp Pro Glu Val
                645                 650                 655

Lys Phe Asn Trp Tyr Val Asp Gly Val Glu Val His Asn Ala Lys Thr
                660                 665                 670

Lys Pro Arg Glu Glu Gln Tyr Asn Ser Thr Tyr Arg Val Val Ser Val
            675                 680                 685

Leu Thr Val Leu His Gln Asp Trp Leu Asn Gly Lys Glu Tyr Lys Cys
690                 695                 700

Lys Val Ser Asn Lys Ala Leu Pro Ala Pro Ile Glu Lys Thr Ile Ser
705                 710                 715                 720

Lys Ala Lys Gly Gln Pro Arg Glu Pro Gln Val Tyr Thr Leu Pro Pro
                725                 730                 735

Ser Arg Asp Glu Leu Thr Lys Asn Gln Val Ser Leu Thr Cys Leu Val
                740                 745                 750

Lys Gly Phe Tyr Pro Ser Asp Ile Ala Val Glu Trp Glu Ser Asn Gly
            755                 760                 765

Gln Pro Glu Asn Asn Tyr Lys Thr Thr Pro Pro Val Leu Asp Ser Asp
770                 775                 780

Gly Ser Phe Phe Leu Tyr Ser Lys Leu Thr Val Asp Lys Ser Arg Trp
785                 790                 795                 800

Gln Gln Gly Asn Val Phe Ser Cys Ser Val Met His Glu Ala Leu His
                805                 810                 815

Asn His Tyr Thr Gln Lys Ser Leu Ser Leu Ser Pro Gly Lys
            820                 825                 830

<210> SEQ ID NO 18
<211> LENGTH: 763
<212> TYPE: PRT
<213> ORGANISM: Artificial Sequence
<220> FEATURE:
<223> OTHER INFORMATION: Human NOPE ECD (427-955)-Fc fusion molecule,
      without signal peptide.

<400> SEQUENCE: 18

Gly Leu Pro Ser Ala Pro Thr Arg Val Thr Ala Thr Pro Leu Ser Ser
1               5                   10                  15

Ser Ala Val Leu Val Ala Trp Glu Arg Pro Glu Met His Ser Glu Gln
                20                  25                  30

Ile Ile Gly Phe Ser Leu His Tyr Gln Lys Ala Arg Gly Met Asp Asn
            35                  40                  45

Val Glu Tyr Gln Phe Ala Val Asn Asn Asp Thr Thr Glu Leu Gln Val
        50                  55                  60

Arg Asp Leu Glu Pro Asn Thr Asp Tyr Glu Phe Tyr Val Val Ala Tyr
65                  70                  75                  80

Ser Gln Leu Gly Ala Ser Arg Thr Ser Thr Pro Ala Leu Val His Thr
                85                  90                  95

Leu Asp Asp Val Pro Ser Ala Pro Gln Leu Ser Leu Ser Ser Pro
                100                 105                 110

Asn Pro Ser Asp Ile Arg Val Ala Trp Leu Pro Leu Pro Pro Ser Leu
            115                 120                 125

Ser Asn Gly Gln Val Val Lys Tyr Lys Ile Glu Tyr Gly Leu Gly Lys
130                 135                 140
```

```
Glu Asp Gln Ile Phe Ser Thr Glu Val Arg Gly Asn Glu Thr Gln Leu
145                 150                 155                 160

Met Leu Asn Ser Leu Gln Pro Asn Lys Val Tyr Arg Val Arg Ile Ser
            165                 170                 175

Ala Gly Thr Ala Ala Gly Phe Gly Ala Pro Ser Gln Trp Met His His
        180                 185                 190

Arg Thr Pro Ser Met His Asn Gln Ser His Val Pro Phe Ala Pro Ala
        195                 200                 205

Glu Leu Lys Val Gln Ala Lys Met Glu Ser Leu Val Val Ser Trp Gln
        210                 215                 220

Pro Pro His Pro Thr Gln Ile Ser Gly Tyr Lys Leu Tyr Trp Arg
225                 230                 235                 240

Glu Val Gly Ala Glu Glu Ala Asn Gly Asp Arg Leu Pro Gly Gly
            245                 250                 255

Arg Gly Asp Gln Ala Trp Asp Val Gly Pro Val Arg Leu Lys Lys Lys
            260                 265                 270

Val Lys Gln Tyr Glu Leu Thr Gln Leu Val Pro Gly Arg Leu Tyr Glu
        275                 280                 285

Val Lys Leu Val Ala Phe Asn Lys His Glu Asp Gly Tyr Ala Ala Val
        290                 295                 300

Trp Lys Gly Lys Thr Glu Lys Ala Pro Ala Pro Asp Met Pro Ile Gln
305                 310                 315                 320

Arg Gly Pro Pro Leu Pro Ala His Val His Ala Glu Ser Asn Ser
            325                 330                 335

Ser Thr Ser Ile Trp Leu Arg Trp Lys Lys Pro Asp Phe Thr Thr Val
            340                 345                 350

Lys Ile Val Asn Tyr Thr Val Arg Phe Ser Pro Trp Gly Leu Arg Asn
        355                 360                 365

Ala Ser Leu Val Thr Tyr Tyr Thr Ser Ser Gly Glu Asp Ile Leu Ile
        370                 375                 380

Gly Gly Leu Lys Pro Phe Thr Lys Tyr Glu Phe Ala Val Gln Ser His
385                 390                 395                 400

Gly Val Asp Met Asp Gly Pro Phe Gly Ser Val Val Glu Arg Ser Thr
            405                 410                 415

Leu Pro Asp Arg Pro Ser Thr Pro Pro Ser Asp Leu Arg Leu Ser Pro
            420                 425                 430

Leu Thr Pro Ser Thr Val Arg Leu His Trp Cys Pro Pro Thr Glu Pro
        435                 440                 445

Asn Gly Glu Ile Val Glu Tyr Leu Ile Leu Tyr Ser Ser Asn His Thr
        450                 455                 460

Gln Pro Glu His Gln Trp Thr Leu Leu Thr Thr Gln Gly Asn Ile Phe
465                 470                 475                 480

Ser Ala Glu Val His Gly Leu Glu Ser Asp Thr Arg Tyr Phe Phe Lys
            485                 490                 495

Met Gly Ala Arg Thr Glu Val Gly Pro Gly Pro Phe Ser Arg Leu Gln
            500                 505                 510

Asp Val Ile Thr Leu Gln Glu Lys Leu Ser Asp Ser Leu Asp Met His
        515                 520                 525

Ser Gly Ser Glu Pro Lys Ser Ser Asp Lys Thr His Thr Cys Pro Pro
        530                 535                 540

Cys Pro Ala Pro Glu Leu Leu Gly Gly Pro Ser Val Phe Leu Phe Pro
545                 550                 555                 560
```

```
Pro Lys Pro Lys Asp Thr Leu Met Ile Ser Arg Thr Pro Glu Val Thr
            565                 570                 575

Cys Val Val Asp Val Ser His Glu Asp Pro Glu Val Lys Phe Asn
        580                 585                 590

Trp Tyr Val Asp Gly Val Glu Val His Asn Ala Lys Thr Lys Pro Arg
        595                 600                 605

Glu Glu Gln Tyr Asn Ser Thr Tyr Arg Val Val Ser Val Leu Thr Val
        610                 615                 620

Leu His Gln Asp Trp Leu Asn Gly Lys Glu Tyr Lys Cys Lys Val Ser
625                 630                 635                 640

Asn Lys Ala Leu Pro Ala Pro Ile Glu Lys Thr Ile Ser Lys Ala Lys
                645                 650                 655

Gly Gln Pro Arg Glu Pro Gln Val Tyr Thr Leu Pro Pro Ser Arg Asp
            660                 665                 670

Glu Leu Thr Lys Asn Gln Val Ser Leu Thr Cys Leu Val Lys Gly Phe
        675                 680                 685

Tyr Pro Ser Asp Ile Ala Val Glu Trp Glu Ser Asn Gly Gln Pro Glu
        690                 695                 700

Asn Asn Tyr Lys Thr Thr Pro Pro Val Leu Asp Ser Asp Gly Ser Phe
705                 710                 715                 720

Phe Leu Tyr Ser Lys Leu Thr Val Asp Lys Ser Arg Trp Gln Gln Gly
                725                 730                 735

Asn Val Phe Ser Cys Ser Val Met His Glu Ala Leu His Asn His Tyr
            740                 745                 750

Thr Gln Lys Ser Leu Ser Leu Ser Pro Gly Lys
            755                 760

<210> SEQ ID NO 19
<211> LENGTH: 567
<212> TYPE: PRT
<213> ORGANISM: Artificial Sequence
<220> FEATURE:
<223> OTHER INFORMATION: Human NOPE ECD (623-955)-Fc fusion molecule,
      without signal peptide.

<400> SEQUENCE: 19

Met His Asn Gln Ser His Val Pro Phe Ala Pro Ala Glu Leu Lys Val
1               5                   10                  15

Gln Ala Lys Met Glu Ser Leu Val Val Ser Trp Gln Pro Pro His
            20                  25                  30

Pro Thr Gln Ile Ser Gly Tyr Lys Leu Tyr Trp Arg Glu Val Gly Ala
        35                  40                  45

Glu Glu Glu Ala Asn Gly Asp Arg Leu Pro Gly Gly Arg Gly Asp Gln
    50                  55                  60

Ala Trp Asp Val Gly Pro Val Arg Leu Lys Lys Val Lys Gln Tyr
65                  70                  75                  80

Glu Leu Thr Gln Leu Val Pro Gly Arg Leu Tyr Glu Val Lys Leu Val
                85                  90                  95

Ala Phe Asn Lys His Glu Asp Gly Tyr Ala Ala Val Trp Lys Gly Lys
            100                 105                 110

Thr Glu Lys Ala Pro Ala Pro Asp Met Pro Ile Gln Arg Gly Pro Pro
        115                 120                 125

Leu Pro Pro Ala His Val His Ala Glu Ser Asn Ser Ser Thr Ser Ile
    130                 135                 140

Trp Leu Arg Trp Lys Lys Pro Asp Phe Thr Thr Val Lys Ile Val Asn
145                 150                 155                 160
```

Tyr Thr Val Arg Phe Ser Pro Trp Gly Leu Arg Asn Ala Ser Leu Val
            165                 170                 175

Thr Tyr Tyr Thr Ser Ser Gly Glu Asp Ile Leu Ile Gly Gly Leu Lys
        180                 185                 190

Pro Phe Thr Lys Tyr Glu Phe Ala Val Gln Ser His Gly Val Asp Met
    195                 200                 205

Asp Gly Pro Phe Gly Ser Val Val Glu Arg Ser Thr Leu Pro Asp Arg
210                 215                 220

Pro Ser Thr Pro Pro Ser Asp Leu Arg Leu Ser Pro Leu Thr Pro Ser
225                 230                 235                 240

Thr Val Arg Leu His Trp Cys Pro Pro Thr Glu Pro Asn Gly Glu Ile
                245                 250                 255

Val Glu Tyr Leu Ile Leu Tyr Ser Ser Asn His Thr Gln Pro Glu His
                260                 265                 270

Gln Trp Thr Leu Leu Thr Thr Gln Gly Asn Ile Phe Ser Ala Glu Val
            275                 280                 285

His Gly Leu Glu Ser Asp Thr Arg Tyr Phe Phe Lys Met Gly Ala Arg
        290                 295                 300

Thr Glu Val Gly Pro Gly Pro Phe Ser Arg Leu Gln Asp Val Ile Thr
305                 310                 315                 320

Leu Gln Glu Lys Leu Ser Asp Ser Leu Asp Met His Ser Gly Ser Glu
                325                 330                 335

Pro Lys Ser Ser Asp Lys Thr His Thr Cys Pro Pro Cys Pro Ala Pro
            340                 345                 350

Glu Leu Leu Gly Gly Pro Ser Val Phe Leu Phe Pro Pro Lys Pro Lys
        355                 360                 365

Asp Thr Leu Met Ile Ser Arg Thr Pro Glu Val Thr Cys Val Val Val
    370                 375                 380

Asp Val Ser His Glu Asp Pro Glu Val Lys Phe Asn Trp Tyr Val Asp
385                 390                 395                 400

Gly Val Glu Val His Asn Ala Lys Thr Lys Pro Arg Glu Glu Gln Tyr
                405                 410                 415

Asn Ser Thr Tyr Arg Val Val Ser Val Leu Thr Val Leu His Gln Asp
            420                 425                 430

Trp Leu Asn Gly Lys Glu Tyr Lys Cys Lys Val Ser Asn Lys Ala Leu
        435                 440                 445

Pro Ala Pro Ile Glu Lys Thr Ile Ser Lys Ala Lys Gly Gln Pro Arg
    450                 455                 460

Glu Pro Gln Val Tyr Thr Leu Pro Pro Ser Arg Asp Glu Leu Thr Lys
465                 470                 475                 480

Asn Gln Val Ser Leu Thr Cys Leu Val Lys Gly Phe Tyr Pro Ser Asp
                485                 490                 495

Ile Ala Val Glu Trp Glu Ser Asn Gly Gln Pro Glu Asn Asn Tyr Lys
            500                 505                 510

Thr Thr Pro Pro Val Leu Asp Ser Asp Gly Ser Phe Phe Leu Tyr Ser
        515                 520                 525

Lys Leu Thr Val Asp Lys Ser Arg Trp Gln Gln Gly Asn Val Phe Ser
    530                 535                 540

Cys Ser Val Met His Glu Ala Leu His Asn His Tyr Thr Gln Lys Ser
545                 550                 555                 560

Leu Ser Leu Ser Pro Gly Lys
                565

-continued

<210> SEQ ID NO 20
<211> LENGTH: 109
<212> TYPE: PRT
<213> ORGANISM: Artificial Sequence
<220> FEATURE:
<223> OTHER INFORMATION: Human myostatin.

<400> SEQUENCE: 20

Asp Phe Gly Leu Asp Cys Asp Glu His Ser Thr Glu Ser Arg Cys Cys
1               5                   10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Glu Cys Glu
        35                  40                  45

Phe Val Phe Leu Gln Lys Tyr Pro His Thr His Leu Val His Gln Ala
    50                  55                  60

Asn Pro Arg Gly Ser Ala Gly Pro Cys Cys Thr Pro Thr Lys Met Ser
65                  70                  75                  80

Pro Ile Asn Met Leu Tyr Phe Asn Gly Lys Glu Gln Ile Ile Tyr Gly
                85                  90                  95

Lys Ile Pro Ala Met Val Val Asp Arg Cys Gly Cys Ser
            100                 105

<210> SEQ ID NO 21
<211> LENGTH: 375
<212> TYPE: PRT
<213> ORGANISM: Artificial Sequence
<220> FEATURE:
<223> OTHER INFORMATION: Human pro-myostatin (with signal sequence).

<400> SEQUENCE: 21

Met Gln Lys Leu Gln Leu Cys Val Tyr Ile Tyr Leu Phe Met Leu Ile
1               5                   10                  15

Val Ala Gly Pro Val Asp Leu Asn Glu Asn Ser Glu Gln Lys Glu Asn
            20                  25                  30

Val Glu Lys Glu Gly Leu Cys Asn Ala Cys Thr Trp Arg Gln Asn Thr
        35                  40                  45

Lys Ser Ser Arg Ile Glu Ala Ile Lys Ile Gln Ile Leu Ser Lys Leu
    50                  55                  60

Arg Leu Glu Thr Ala Pro Asn Ile Ser Lys Asp Val Ile Arg Gln Leu
65                  70                  75                  80

Leu Pro Lys Ala Pro Pro Leu Arg Glu Leu Ile Asp Gln Tyr Asp Val
                85                  90                  95

Gln Arg Asp Asp Ser Ser Asp Gly Ser Leu Glu Asp Asp Asp Tyr His
            100                 105                 110

Ala Thr Thr Glu Thr Ile Ile Thr Met Pro Thr Glu Ser Asp Phe Leu
        115                 120                 125

Met Gln Val Asp Gly Lys Pro Lys Cys Cys Phe Phe Lys Phe Ser Ser
    130                 135                 140

Lys Ile Gln Tyr Asn Lys Val Val Lys Ala Gln Leu Trp Ile Tyr Leu
145                 150                 155                 160

Arg Pro Val Glu Thr Pro Thr Thr Val Phe Val Gln Ile Leu Arg Leu
                165                 170                 175

Ile Lys Pro Met Lys Asp Gly Thr Arg Tyr Thr Gly Ile Arg Ser Leu
            180                 185                 190

Lys Leu Asp Met Asn Pro Gly Thr Gly Ile Trp Gln Ser Ile Asp Val
        195                 200                 205

```
Lys Thr Val Leu Gln Asn Trp Leu Lys Gln Pro Glu Ser Asn Leu Gly
    210                 215                 220

Ile Glu Ile Lys Ala Leu Asp Glu Asn Gly His Asp Leu Ala Val Thr
225                 230                 235                 240

Phe Pro Gly Pro Gly Glu Asp Gly Leu Asn Pro Phe Leu Glu Val Lys
                    245                 250                 255

Val Thr Asp Thr Pro Lys Arg Ser Arg Arg Asp Phe Gly Leu Asp Cys
                260                 265                 270

Asp Glu His Ser Thr Glu Ser Arg Cys Cys Arg Tyr Pro Leu Thr Val
            275                 280                 285

Asp Phe Glu Ala Phe Gly Trp Asp Trp Ile Ile Ala Pro Lys Arg Tyr
        290                 295                 300

Lys Ala Asn Tyr Cys Ser Gly Glu Cys Glu Phe Val Phe Leu Gln Lys
305                 310                 315                 320

Tyr Pro His Thr His Leu Val His Gln Ala Asn Pro Arg Gly Ser Ala
                325                 330                 335

Gly Pro Cys Cys Thr Pro Thr Lys Met Ser Pro Ile Asn Met Leu Tyr
                340                 345                 350

Phe Asn Gly Lys Glu Gln Ile Ile Tyr Gly Lys Ile Pro Ala Met Val
            355                 360                 365

Val Asp Arg Cys Gly Cys Ser
            370                 375

<210> SEQ ID NO 22
<211> LENGTH: 352
<212> TYPE: PRT
<213> ORGANISM: Artificial Sequence
<220> FEATURE:
<223> OTHER INFORMATION: Human pro-myostatin (without signal sequence).

<400> SEQUENCE: 22

Asn Glu Asn Ser Glu Gln Lys Glu Asn Val Glu Lys Glu Gly Leu Cys
1               5                   10                  15

Asn Ala Cys Thr Trp Arg Gln Asn Thr Lys Ser Ser Arg Ile Glu Ala
            20                  25                  30

Ile Lys Ile Gln Ile Leu Ser Lys Leu Arg Leu Glu Thr Ala Pro Asn
        35                  40                  45

Ile Ser Lys Asp Val Ile Arg Gln Leu Leu Pro Lys Ala Pro Pro Leu
    50                  55                  60

Arg Glu Leu Ile Asp Gln Tyr Asp Val Gln Arg Asp Asp Ser Ser Asp
65                  70                  75                  80

Gly Ser Leu Glu Asp Asp Asp Tyr His Ala Thr Thr Glu Thr Ile Ile
                85                  90                  95

Thr Met Pro Thr Glu Ser Asp Phe Leu Met Gln Val Asp Gly Lys Pro
            100                 105                 110

Lys Cys Cys Phe Phe Lys Phe Ser Ser Lys Ile Gln Tyr Asn Lys Val
        115                 120                 125

Val Lys Ala Gln Leu Trp Ile Tyr Leu Arg Pro Val Glu Thr Pro Thr
    130                 135                 140

Thr Val Phe Val Gln Ile Leu Arg Leu Ile Lys Pro Met Lys Asp Gly
145                 150                 155                 160

Thr Arg Tyr Thr Gly Ile Arg Ser Leu Lys Leu Asp Met Asn Pro Gly
                165                 170                 175

Thr Gly Ile Trp Gln Ser Ile Asp Val Lys Thr Val Leu Gln Asn Trp
            180                 185                 190
```

```
Leu Lys Gln Pro Glu Ser Asn Leu Gly Ile Glu Ile Lys Ala Leu Asp
        195                 200                 205

Glu Asn Gly His Asp Leu Ala Val Thr Phe Pro Pro Gly Glu Asp
    210                 215                 220

Gly Leu Asn Pro Phe Leu Glu Val Lys Val Thr Asp Thr Pro Lys Arg
225                 230                 235                 240

Ser Arg Arg Asp Phe Gly Leu Asp Cys Asp Glu His Ser Thr Glu Ser
                245                 250                 255

Arg Cys Cys Arg Tyr Pro Leu Thr Val Asp Phe Glu Ala Phe Gly Trp
            260                 265                 270

Asp Trp Ile Ile Ala Pro Lys Arg Tyr Lys Ala Asn Tyr Cys Ser Gly
        275                 280                 285

Glu Cys Glu Phe Val Phe Leu Gln Lys Tyr Pro His Thr His Leu Val
    290                 295                 300

His Gln Ala Asn Pro Arg Gly Ser Ala Gly Pro Cys Cys Thr Pro Thr
305                 310                 315                 320

Lys Met Ser Pro Ile Asn Met Leu Tyr Phe Asn Gly Lys Glu Gln Ile
                325                 330                 335

Ile Tyr Gly Lys Ile Pro Ala Met Val Val Asp Arg Cys Gly Cys Ser
            340                 345                 350

<210> SEQ ID NO 23
<211> LENGTH: 109
<212> TYPE: PRT
<213> ORGANISM: Artificial Sequence
<220> FEATURE:
<223> OTHER INFORMATION: Mouse myostatin.

<400> SEQUENCE: 23

Asp Phe Gly Leu Asp Cys Asp Glu His Ser Thr Glu Ser Arg Cys Cys
1               5                   10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Glu Cys Glu
        35                  40                  45

Phe Val Phe Leu Gln Lys Tyr Pro His Thr His Leu Val His Gln Ala
    50                  55                  60

Asn Pro Arg Gly Ser Ala Gly Pro Cys Cys Thr Pro Thr Lys Met Ser
65                  70                  75                  80

Pro Ile Asn Met Leu Tyr Phe Asn Gly Lys Glu Gln Ile Ile Tyr Gly
                85                  90                  95

Lys Ile Pro Ala Met Val Val Asp Arg Cys Gly Cys Ser
            100                 105

<210> SEQ ID NO 24
<211> LENGTH: 376
<212> TYPE: PRT
<213> ORGANISM: Artificial Sequence
<220> FEATURE:
<223> OTHER INFORMATION: Mouse pro-myostatin (with signal sequence).

<400> SEQUENCE: 24

Met Met Gln Lys Leu Gln Met Tyr Val Tyr Ile Tyr Leu Phe Met Leu
1               5                   10                  15

Ile Ala Ala Gly Pro Val Asp Leu Asn Glu Gly Ser Glu Arg Glu Glu
            20                  25                  30

Asn Val Glu Lys Glu Gly Leu Cys Asn Ala Cys Ala Trp Arg Gln Asn
```

```
                  35                  40                  45
Thr Arg Tyr Ser Arg Ile Glu Ala Ile Lys Ile Gln Ile Leu Ser Lys
         50                  55                  60

Leu Arg Leu Glu Thr Ala Pro Asn Ile Ser Lys Asp Ala Ile Arg Gln
 65                  70                  75                  80

Leu Leu Pro Arg Ala Pro Pro Leu Arg Glu Leu Ile Asp Gln Tyr Asp
                 85                  90                  95

Val Gln Arg Asp Asp Ser Ser Asp Gly Ser Leu Glu Asp Asp Tyr
             100                 105                 110

His Ala Thr Thr Glu Thr Ile Ile Thr Met Pro Thr Glu Ser Asp Phe
             115                 120                 125

Leu Met Gln Ala Asp Gly Lys Pro Lys Cys Cys Phe Phe Lys Phe Ser
        130                 135                 140

Ser Lys Ile Gln Tyr Asn Lys Val Val Lys Ala Gln Leu Trp Ile Tyr
145                 150                 155                 160

Leu Arg Pro Val Lys Thr Pro Thr Thr Val Phe Val Gln Ile Leu Arg
                165                 170                 175

Leu Ile Lys Pro Met Lys Asp Gly Thr Arg Tyr Thr Gly Ile Arg Ser
            180                 185                 190

Leu Lys Leu Asp Met Ser Pro Gly Thr Gly Ile Trp Gln Ser Ile Asp
        195                 200                 205

Val Lys Thr Val Leu Gln Asn Trp Leu Lys Gln Pro Glu Ser Asn Leu
    210                 215                 220

Gly Ile Glu Ile Lys Ala Leu Asp Glu Asn Gly His Asp Leu Ala Val
225                 230                 235                 240

Thr Phe Pro Gly Pro Gly Glu Asp Gly Leu Asn Pro Phe Leu Glu Val
                245                 250                 255

Lys Val Thr Asp Thr Pro Lys Arg Ser Arg Arg Asp Phe Gly Leu Asp
            260                 265                 270

Cys Asp Glu His Ser Thr Glu Ser Arg Cys Cys Arg Tyr Pro Leu Thr
        275                 280                 285

Val Asp Phe Glu Ala Phe Gly Trp Asp Trp Ile Ile Ala Pro Lys Arg
    290                 295                 300

Tyr Lys Ala Asn Tyr Cys Ser Gly Glu Cys Glu Phe Val Phe Leu Gln
305                 310                 315                 320

Lys Tyr Pro His Thr His Leu Val His Gln Ala Asn Pro Arg Gly Ser
                325                 330                 335

Ala Gly Pro Cys Cys Thr Pro Thr Lys Met Ser Pro Ile Asn Met Leu
            340                 345                 350

Tyr Phe Asn Gly Lys Glu Gln Ile Ile Tyr Gly Lys Ile Pro Ala Met
        355                 360                 365

Val Val Asp Arg Cys Gly Cys Ser
    370                 375

<210> SEQ ID NO 25
<211> LENGTH: 351
<212> TYPE: PRT
<213> ORGANISM: Artificial Sequence
<220> FEATURE:
<223> OTHER INFORMATION: Mouse pro-myostatin (without signal sequence).

<400> SEQUENCE: 25

Glu Gly Ser Glu Arg Glu Glu Asn Val Glu Lys Glu Gly Leu Cys Asn
 1               5                  10                  15

Ala Cys Ala Trp Arg Gln Asn Thr Arg Tyr Ser Arg Ile Glu Ala Ile
```

```
                    20                  25                  30
Lys Ile Gln Ile Leu Ser Lys Leu Arg Leu Glu Thr Ala Pro Asn Ile
                35                  40                  45

Ser Lys Asp Ala Ile Arg Gln Leu Leu Pro Arg Ala Pro Pro Leu Arg
 50                  55                  60

Glu Leu Ile Asp Gln Tyr Asp Val Gln Arg Asp Ser Ser Asp Gly
 65                  70                  75                  80

Ser Leu Glu Asp Asp Tyr His Ala Thr Thr Glu Thr Ile Ile Thr
                85                  90                  95

Met Pro Thr Glu Ser Asp Phe Leu Met Gln Ala Asp Gly Lys Pro Lys
                100                 105                 110

Cys Cys Phe Phe Lys Phe Ser Ser Lys Ile Gln Tyr Asn Lys Val Val
                115                 120                 125

Lys Ala Gln Leu Trp Ile Tyr Leu Arg Pro Val Lys Thr Pro Thr Thr
                130                 135                 140

Val Phe Val Gln Ile Leu Arg Leu Ile Lys Pro Met Lys Asp Gly Thr
145                 150                 155                 160

Arg Tyr Thr Gly Ile Arg Ser Leu Lys Leu Asp Met Ser Pro Gly Thr
                165                 170                 175

Gly Ile Trp Gln Ser Ile Asp Val Lys Thr Val Leu Gln Asn Trp Leu
                180                 185                 190

Lys Gln Pro Glu Ser Asn Leu Gly Ile Glu Ile Lys Ala Leu Asp Glu
                195                 200                 205

Asn Gly His Asp Leu Ala Val Thr Phe Pro Gly Pro Gly Glu Asp Gly
                210                 215                 220

Leu Asn Pro Phe Leu Glu Val Lys Val Thr Asp Thr Pro Lys Arg Ser
225                 230                 235                 240

Arg Arg Asp Phe Gly Leu Asp Cys Asp Glu His Ser Thr Glu Ser Arg
                245                 250                 255

Cys Cys Arg Tyr Pro Leu Thr Val Asp Phe Glu Ala Phe Gly Trp Asp
                260                 265                 270

Trp Ile Ile Ala Pro Lys Arg Tyr Lys Ala Asn Tyr Cys Ser Gly Glu
                275                 280                 285

Cys Glu Phe Val Phe Leu Gln Lys Tyr Pro His Thr His Leu Val His
                290                 295                 300

Gln Ala Asn Pro Arg Gly Ser Ala Gly Pro Cys Cys Thr Pro Thr Lys
305                 310                 315                 320

Met Ser Pro Ile Asn Met Leu Tyr Phe Asn Gly Lys Glu Gln Ile Ile
                325                 330                 335

Tyr Gly Lys Ile Pro Ala Met Val Val Asp Arg Cys Gly Cys Ser
                340                 345                 350

<210> SEQ ID NO 26
<211> LENGTH: 232
<212> TYPE: PRT
<213> ORGANISM: Artificial Sequence
<220> FEATURE:
<223> OTHER INFORMATION: Fc C237S.

<400> SEQUENCE: 26

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
```

```
            35                  40                  45
Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 27
<211> LENGTH: 228
<212> TYPE: PRT
<213> ORGANISM: Artificial Sequence
<220> FEATURE:
<223> OTHER INFORMATION: Exemplary Fc #1.

<400> SEQUENCE: 27

Glu Arg Lys Cys Cys Val Glu Cys Pro Pro Cys Pro Ala Pro Pro Val
 1                   5                  10                  15

Ala Gly Pro Ser Val Phe Leu Phe Pro Pro Lys Pro Lys Asp Thr Leu
                 20                  25                  30

Met Ile Ser Arg Thr Pro Glu Val Thr Cys Val Val Val Asp Val Ser
             35                  40                  45

His Glu Asp Pro Glu Val Gln Phe Asn Trp Tyr Val Asp Gly Val Glu
 50                  55                  60

Val His Asn Ala Lys Thr Lys Pro Arg Glu Glu Gln Phe Asn Ser Thr
 65                  70                  75                  80

Phe Arg Val Val Ser Val Leu Thr Val Val His Gln Asp Trp Leu Asn
                 85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
        115                 120                 125

Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
```

```
                    165                 170                 175
Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225

<210> SEQ ID NO 28
<211> LENGTH: 229
<212> TYPE: PRT
<213> ORGANISM: Artificial Sequence
<220> FEATURE:
<223> OTHER INFORMATION: Exemplary Fc #2.

<400> SEQUENCE: 28

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225
```